(12) United States Patent
Chen et al.

(10) Patent No.: US 8,030,518 B2
(45) Date of Patent: Oct. 4, 2011

(54) 1,4 DIAMINO BICYCLIC RETIGABINE ANALOGUES AS POTASSIUM CHANNEL MODULATORS

(75) Inventors: Huanming Chen, Irvine, CA (US); Jianlan Song, Cerritos, CA (US); Jean-Michel Vernier, Laguna Niguel, CA (US); Jim Zhen Wu, Aliso Viejo, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 929 days.

(21) Appl. No.: 11/946,822

(22) Filed: Nov. 28, 2007

(65) Prior Publication Data
US 2008/0234334 A1 Sep. 25, 2008

Related U.S. Application Data

(60) Provisional application No. 60/867,482, filed on Nov. 28, 2006.

(51) Int. Cl.
*C07C 233/05* (2006.01)
*A61K 31/165* (2006.01)

(52) U.S. Cl. ........ 564/180; 514/352; 514/480; 514/619; 546/309; 560/28

(58) Field of Classification Search .................. 514/352, 514/480, 619; 564/180; 546/309; 560/28
See application file for complete search history.

(56) References Cited

U.S. PATENT DOCUMENTS

| | | | |
|---|---|---|---|
| 4,181,803 A | 1/1980 | Morita et al. |
| 4,554,281 A | 11/1985 | vonBebenburg et al. |
| 4,668,684 A | 5/1987 | Tibes et al. |
| 4,778,799 A | 10/1988 | Tibes et al. |
| 4,923,858 A | 5/1990 | Engel et al. |
| 4,923,974 A | 5/1990 | Ueda et al. |
| 5,032,591 A | 7/1991 | Evans et al. |
| 5,162,346 A | 11/1992 | Lobisch et al. |
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 7/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 6,117,900 A | 9/2000 | Rundfeldt et al. |
| 6,211,171 B1 | 4/2001 | Sawynok et al. |
| 6,218,411 B1 | 4/2001 | Koga |
| 6,265,417 B1 | 7/2001 | Carroll |
| 6,281,211 B1 | 8/2001 | Cai et al. |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |
| 6,538,004 B2 | 3/2003 | Drizin |
| 6,538,151 B1 | 3/2003 | Meisel et al. |
| RE38,115 E | 5/2003 | Smith et al. |
| 6,589,986 B2 | 7/2003 | Bowlby et al. |
| 6,593,335 B1 | 7/2003 | Carroll |
| 6,642,209 B1 | 11/2003 | Fukunuga |
| 6,645,521 B2 | 11/2003 | Cassel |
| 6,737,422 B2 | 5/2004 | McNaughton-Smith et al. |
| 7,045,551 B2 | 5/2006 | Wu et al. |
| 7,160,684 B2 | 1/2007 | Argentieri et al. |
| 7,250,511 B2 * | 7/2007 | Bavetsias ...................... 544/344 |

(Continued)

FOREIGN PATENT DOCUMENTS

CA 2542434 5/2005

(Continued)

OTHER PUBLICATIONS

West, Anthony R., Solid State Chemistry and its Applications, Wiley, New York, 1988, pp. 358 & 365.*
Beeby et al. "The synthesis and properties of 2:7-Disubstituted 1:2:3:4-tetrahydroisoquinolines," *J. Chem. Soc.* ¶ 385, 1799-1803 (1949).
Reich et al., "Design and synthesis of novel 6,7-imidazotetrahydroquinoline inhibitors of thymidylate synthase using iterative protein crystal structure analysis," *J. Med. Chem.* 35:847-858 (1992).
Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).

(Continued)

*Primary Examiner* — Shailendra Kumar
(74) *Attorney, Agent, or Firm* — Jones Day

(57) ABSTRACT

This invention is directed to compounds of formula I,

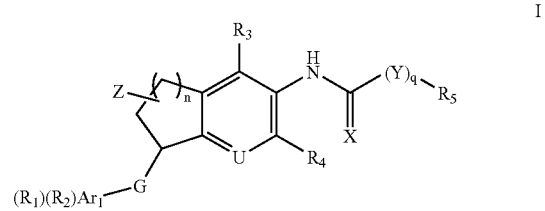

where G is —O—, —S—, —C($g_1$)($g_2$)-, or —NH—, and n=1, 2, or 3. Such compounds modulate potassium channels. The compounds are useful for the treatment and prevention of diseases and disorders which are affected by modulation of potassium ion channels. One such condition is seizure disorders.

38 Claims, No Drawings

U.S. PATENT DOCUMENTS

| | | | |
|---|---|---|---|
| 7,309,713 | B2 | 12/2007 | Rundfeldt et al. |
| 7,419,981 | B2 | 9/2008 | Field et al. |
| 2002/0013349 | A1 | 1/2002 | Wickenden |
| 2002/0015730 | A1 | 2/2002 | Hoffmann et al. |
| 2002/0183395 | A1 | 12/2002 | Argentieri |
| 2004/0198724 | A1 | 10/2004 | McNaughton-Smith et al. |
| 2005/0089473 | A1 | 4/2005 | Black et al. |
| 2005/0089559 | A1 | 4/2005 | Szelenyi |
| 2005/0090547 | A1 | 4/2005 | Szelenyi |
| 2005/0202394 | A1 | 9/2005 | Dobson |
| 2005/0277579 | A1 | 12/2005 | Krishnan et al. |
| 2007/0066612 | A1 | 3/2007 | Khanzhin et al. |

FOREIGN PATENT DOCUMENTS

| | | |
|---|---|---|
| DE | 3337593 | 10/1983 |
| DE | 3604575 A1 | 8/1986 |
| DE | 103 49 729.3 | 10/2003 |
| DE | 103 59 335 | 5/2005 |
| EP | 1 189 788 A1 | 8/1986 |
| EP | 0 343 429 | 5/1989 |
| EP | 1 334 972 | 8/2003 |
| EP | 1 407 768 | 4/2004 |
| EP | 1 813 285 A1 | 8/2007 |
| JP | 2000 14350 | 5/2000 |
| JP | 2000 143510 A | 5/2000 |
| RU | 2006117525 | 12/2005 |
| WO | WO/00/55137 | 9/2000 |
| WO | WO 00/59487 A2 | 10/2000 |
| WO | WO 00/59508 A1 | 10/2000 |
| WO | WO 01/001970 | 1/2001 |
| WO | WO 01/01972 A2 | 1/2001 |
| WO | WO 01/009612 | 2/2001 |
| WO | WO 01/22953 A2 | 4/2001 |
| WO | WO 02/080898 | 10/2002 |
| WO | WO/03/020706 | 3/2003 |
| WO | WO/03/097586 | 11/2003 |
| WO | WO 03/106424 A1 | 12/2003 |
| WO | WO 2004/082677 | 3/2004 |
| WO | WO 2004/058739 | 7/2004 |
| WO | WO 2004/080950 | 9/2004 |
| WO | WO 2004/096767 | 11/2004 |
| WO | WO 2004/096767 A1 | 11/2004 |
| WO | WO 2004/105795 | 12/2004 |
| WO | WO 2005/087754 | 3/2005 |
| WO | WO 2005/039576 A1 | 5/2005 |
| WO | WO 2005/048975 | 6/2005 |
| WO | WO 2005/100349 A2 | 10/2005 |
| WO | WO 2006/029623 | 3/2006 |
| WO | WO 2006/092143 | 9/2006 |
| WO | WO 2008/024398 A2 | 2/2008 |
| WO | WO 2008/066900 A1 | 6/2008 |

OTHER PUBLICATIONS

Armijo et al., "Ion channels and epilepsy," *Curr Pharm Des.* 11:1975-2003 (2005).
Barhanin, M., et al., "K$_v$LQT1 and ISK (minK) proteins associate to form the I$_{KS}$ cardiac potassium current," *Nature* 384(6604):78-80 (1996).
Bialer et al., "Progress report on new antiepileptic drugs: a summary of the fourth Eilat conference (EILAT IV)," *Epilepsy Res.* 34:1-41 (1999).
Bialer, "Progress report on new antiepileptic drugs: a summary of the Sixth Eilat Conference (EILAT VI)," *Epilepsy Res.* 51:31-71 (2002).
Bialer, "Progress report on new antiepileptic drugs: a summary of the Seventh Eilat Conference (EILAT VII)," *Epilepsy Res.* 61:1-48 (2004).
Biervert et al., "A potassium channel mutation in neonatal human epilepsy," *Science* 279:403-406 (1998).
Blackburn-Munro and Jensen, "The anticonvulsant retigabine attenuates nociceptive behaviours in rat models of persistent and neuropathic pain," *Eur J Pharmacol.* 460: 109-116 (2003).
Brown and Adams, "Muscarinic suppression of a novel voltage-sensitive K$^+$current in a vertebrate neurone," *Nature* 283:673-676 (1980).
Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 (1998).
Cooper et al., "Colocalization and coassembly of two human brain M-type potassium channel subunits that are mutated in epilepsy," *Proc Natl Acad Sci USA* 97:4914-4919 (2000).
Delmas and Brown, "Pathways modulating neural KCNQ/M (Kv7) potassium channels," *Nat Rev Neurosci.* 6:850-862 (2005).
Dickenson al., "Neurobiology of neuropathic pain: mode of action of anticonvulsants," *Eur. J. Pain* 6:51-60 (2002).
Dost et al., "The anticonvulsant retigabine potently suppresses epileptiform discharges in the low Ca ++ and low Mg++ model in the hippocampal slice preparation," *Epilepsy Res.* 38:53-56 (2000).
Friedel and Fitton, "Flupirtine: a review of its analgesic properties, and therapeutic efficacy in pain states," *Drugs* 45:548-569 (1993).
Hiller et al., "Retigabine N-glucuronidation and its potential role in enterohepatic circulation," *Drug Metab Dispos.* 27(5):605-612 (1999).
Hunt and Mantyh, "The molecular dynamics of pain control," *Nat Rev Neurosci.* 2:83-91 (2001).
Jentsch, "Neuronal KCNQ potassium channels; physiology and role in disease," *Nat. Rev Neurosci.*, 1:21-30 (2000).
Jiang et al., "X-ray structure of a voltage-dependent K+ channel," *Nature* 423:33-41. (2003).
Kharkovets et al., "Mice with altered KCNQ4 K$^+$ channels implicate sensory outer hair cells in human progressive deafness," *EMBO J* 25:642-652 (2006).
Kibbe *Handbook of Pharmaceutical Excipients* (Pharmaceutical Press, London) (2000).
Kubisch et al., "KCNQ4, a novel potassium channel expressed in sensory outer hair cells, is mutated in dominant deafness," *Cell* 96:437-446 (1999).
Lamas et al., "Effects of a cognition-enhancer, linopirdine (DuP 996), on M-type potassium currents (I$_{K(M)}$) and some other voltage- and ligand-gated membrane currents in rat sympathetic neurons," *Eur. J Neurosci.*, 9:605-616 (1997).
Lee et al., "Structure of the KvAP voltage-dependent K$^+$ channel and its dependence on the lipid membrane," *Proc Natl Acad Sci USA* 102:15441-15446 (2005).
Long et al., "Crystal Structure of a mammalian voltage-dependent *Shaker* family K$^+$ channel," *Science* 309:897-903 (2005).
Main et al., "Modulation of KCNQ2/3 potassium channels by the novel anticonvulsant retigabine," *Mol. Pharmacol.* 58:253-262 (2000).
Marrion, "Control of M-current," *Annu Rev Physiol.* 59:483-504 (1997).
Parcej and Eckhardt-Strelau, Structural characterization of neuronal voltage-sensitive K$^+$ channels heterologously expressed in *Pichia pastoris, J Mol Biol* 333:103-116 (2003).
Passmore et al., "KCNQ/M currents in sensory neurons: significance for pain therapy," *J. Neurosci.* 23:7227-7236 (2003).
Porter et al., "Retigabine," *Neurotherapeutics* 4:149-154 (2007).
Rogawski, MA, "KCNQ2/KCNQ3 K+ channels and the molecular pathogenesis of epilepsy: implications for therapy," *Trends Neurosci.* 23:393-398 (2000).
Rostock et al., "A new anticonvulsant with broad spectrum activity in animal models of epileptic seizures," *Epilepsy Res.*23:211-223 (1996).
Rundfeldt et al., "Multiple actions of the new anticonvulsant D-23129 on voltage-gated inward currents and GABA-induced currents in cultured neuronal cells (abstract)," *Naunyn-Schmiedeberg's Arch Pharmacol* 351 (Suppl):R160 (1995).
Rundfeldt, "Characterization of the K$^+$ channel opening effect of the anti-convulsant retigabine in PC12 cells," *Epilepsy Res.*35:99-107 (1999).
Rundfeldt, "The new anticonvulsant retigabine (D23129) acts as an opener of K$^+$ channels in neuronal cells," *Eur J Pharmacol.* 336:243-249 (1997).
Schroeder et al., "KCNQ5, a novel potassium channel broadly expressed in brain, mediates M-type currents," *J. Biol. Chem.* 275:24089-24095 (2000).

Schroeder, "Moderate loss of function of cyclic-AMP-modulated KNCQ2/KCNQ3 K+ channels causes epilepsy" *Nature* 396:687-690 (1998).

Singh et al., "A novel potassium channel gene, KCNQ2, is mutated in an inherited epilepsy of newborns," *Nat Genet.* 18:25-29 (1998).

Suzuki and Dickenson, "Neuropathic pain: nerves bursting with excitement," *NeuroReport* 11:R17-R21 (2000).

Tatulian and Brown, "Effect of the KCNQ potassium channel opener retigabine on single KCNQ2/3 channels express in CHO cells," *J Physiol.* 549:57-63 (2003).

Tatulian et al., "Activation of expressed KCNQ potassium currents and native neuronal M-type potassium currents by the anti-convulsant drug retigabine," *J. Neurosci.* 21:5535-5545 (2001).

Tober et al., "A potent anticonvulsant in the amygdala kindling model of complex partial seizures," *Eur J Pharmacol*, 303:163-169 (1996).

Wang et al., KCNQ2 and KCNQ3 potassium channel subunits: molecular correlates of the M-channel, *Science* 282:1890-1893 (1998).

Wang et al., "Positional cloning of a novel potassium channel gene: KVLQT1 mutations cause cardiac arrhythmias," *Nat Genet* 12:17-23 (1996).

Watanbe et al., "Disruption of the epilepsy KCNQ2 gene results in neural hyperexcitability," *J. Neurochem* 75:28-33 (2000).

Wickenden et al., "KCNQ potassium channels: drug targets for the treatment of epilepsy and pain," *Exp. Opin Thera Patents* 14(4): 457-469 (2004).

Wickenden et al., "Retigabine, a novel anti-convulsant, enhances activation of KCNQ2/Q3 potassium channels," *Mol. Pharmacol.* 58:591-600 (2000).

Wuttke, "The new anticonvulsant retigabine favors voltage-dependent opening of the Kv7.2 (KCNQ2) channel by binding to its activation gate," *Mol. Pharmacol.* 67:1009-1017 (2005).

Beck et al., "Kreuzschmerzen in der Gynaekologischen praxis," Ginaekologe, Springer Verlag, Berlin Germany 35(5):490-494 (2002).

Kuo et al., "Inhibition of $Na^+$ current by diphenhydramine and other diphenyl compounds: molecular determinants of selective binding to the inactivated channels," *Mol. Pharmacol.* 57(1):135-143(2000).

Patani, "Bioisosterism: A Rational Approach in Drug Design," *Chem. Rev.* 96:3147-3176 (1996).

Touboul et al. "A Comparative evaluation of the effects of Propafenone and Iidocaine on early ventricular arrhythmias after acute myocardial infarction," *Eur. Heart J.* 9:1188-1193 (1988). Abstract.

Vippagunta et al., "Crystalline solids," *Adv. Drug Deliv. Rev.* 48:3-26 (2001).

Von Bebenburg et al., "Substituierte Polyaminopyridine" *Chemiker-Zeitung* 103:387-399 (1979).

Wolf(ed.), Burger's Medicinal Chemistry and Drug Discovery, 5th Edition vol. 1: Principles and Practice, John Wiley & Sons, New York, pp. 975-977 (1995).

Wu et al., "Regulatory perspectives of Type II prodrug development and time-dependent toxicity management: nonclinical Pharm/Tox analysis and the role of comparative toxicology," *Toxicology* 236:1-6 (2007).

Zani et al., "Sodium channels are required during in vivo sodium chloride hyperosmolarity to stimulate increase in intestinal endothelial nitric oxide production" *Am. J. Physiol. Heart Circ. Physiol.* 288:H89-H95 (2005).

\* cited by examiner

1,4 DIAMINO BICYCLIC RETIGABINE ANALOGUES AS POTASSIUM CHANNEL MODULATORS

CROSS REFERENCE TO RELATED APPLICATIONS

This application claims the benefit of U.S. Provisional Application Ser. No. 60/867,482 filed Nov. 28, 2006.

FIELD OF THE INVENTION

This invention concerns compounds that modulate potassium channels. The compounds are useful for the treatment and prevention of diseases and disorders which are affected by modulation of potassium ion channels. One such condition is seizure disorders.

BACKGROUND OF THE INVENTION

Retigabine (N-[2-amino-4-(4-fluorobenzylamino)phenyl] carbamic acid, ethyl ester] (U.S. Pat. No. 5,384,330) has been found to be an effective treatment of seizure disorders. Bialer, M., et al., *Epilepsy Research* 1999, 34, 1-41. Retigabine has also been found to be useful in treating pain, including neuropathic and chronic pain. Blackburn-Munro and Jensen, Eur. J. Pharmacol. 2003, 460, 109-116. It also exhibits potent anxiolytic effect in various animal models. Blackburn-Munro, G. et al, CNS Drug Reviews 2005, 11, 1-20.

Benign familial neonatal convulsions, an inherited form of epilepsy, has been associated with mutations in the KCNQ2/3 channels. Biervert, C., et al., Science 1998, 27, 403-06; Singh, N. A., et al., Nat. Genet. 1998, 18, 25-29; Charlier, C., et al., Nat. Genet. 1998, 18, 53-55, Rogawski, Trends in Neurosciences 2000, 23, 393-398. Subsequent investigations have established that the site of action of retigabine is the KCNQ2/3 channel. Wickenden, A. D. et al., Mol. Pharmacol. 2000, 58, 591-600; Main, M. J., et al., Mol. Pharmcol. 2000, 58, 253-62. Retigabine has been shown to increase the conductance of the channels at the resting membrane potential and to bind the activation gate of the KCNQ2/3 channel. Wuttke, T. V., et al., *Mol. Pharmacol.* 2005, 67, 1009-1017.

The recognition of the site of action of retigabine has prompted a search for other KCNQ 2/3 activators among compounds related to retigabine. WO 2004/058739 describes several compounds in which a thienylmethylamino or benzothienyl methylamino group replaced the 4-fluorobenzylamino group of retigabine; these compounds were reported to be useful as KCNQ 2/3 activators. WO 2004/80950 and WO 2004/82677 describe such compounds where the 4-fluorobenzylamino group of retigabine is replaced by a phenylaminomethyl group. WO 2004/96767 reports compounds which are N-[1-benzyl-4-aminoindol-5-yl]carbamic acid esters. WO 2005/087754 describes a class of reputed KCNQ 2/3 activators that are N-phenyl carbamic acid esters or N-phenyl-amides (for example, N-phenyl acetamides), but in which the central phenyl group lacks an amino group at the 2-position. Typical compounds are N-(2,6-dimethyl-4-(morpholinyl-4-yl)-phenyl)-carbamic acid benzyl ester and 2-cyclopentyl-N-(2,6-dimethyl-4-[2-(4-trifluoromethyl phenyl]-morpholinyl-4-yl)-phenyl)-acetamide.

SUMMARY OF THE INVENTION

The present invention relates to compounds that modulate potassium channels. More particularly, the present invention relates to treatment and prevention of diseases and disorders, such as seizure disorders, which are affected by modulation of potassium ion channels.

The compounds of the present invention are bicyclic retigabine analogues which activate potassium channel activity, and are thereby useful for treatment for conditions such as seizure disorder, without producing significant systemic side effects when administered systemically.

In one embodiment, this invention is directed to compounds of formula I,

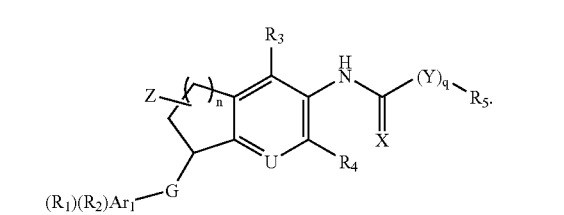

where G is —O—, —S—, —C($g_1$)($g_2$)-, or —NH—, where $g_1$ and $g_2$ are, independently, H, phenyl, halogen, methoxy, halomethyl, methoxymethyl, or $C_1$-$C_3$ alkyl; n=1, 2, or 3, $Ar_1$ is a 5- to 10-member mono- or bicyclic aromatic group, optionally containing 1-4 heteroatoms selected independently from N, O, and S; $R_1$ and $R_2$ are selected, independently, from H, CN, halogen, $CH_2CN$, OH, $NO_2$, $CH_2F$, $CHF_2$, $CF_3$, $CF_2CF_3$, $C_1$-$C_6$ alkyl, $OR_8$, C(=O)$R_9$, C(=O)$_OR_{10}$, OC(=O)$R_{11}$, $SR_{12}$, $NR_{13}$C(=O)$R_{14}$, $NR_{13}$C(=NH)$R_{14}$, C(=O)$NR_{15}R_{16}$, $CH_2$C(=O)$NR_{15}R_{16}$, $CH_3$NHC(=NH)—, $CH_3$C(=NH)NH—, $CH_2$C(=NH)$NH_2$, $NR_{17}R_{18}$, $SO_2R_{19}$, N($R_{20}$)$SO_2R_{21}$, $SO_2NR_{22}R_{23}$, $C_3$-$C_6$ cycloalkyl, $C_5$-$C_6$ cycloalkenyl, $C_2$-$C_6$ alkenyl, or $C_2$-$C_6$ alkynyl; U is N or CR'; R', $R_3$, and $R_4$ are, independently, H, halogen, $C_{1-6}$ alkyl, which $C_{1-6}$ alkyl group optionally substituted with 1 or 2 groups selected, independently, from OH, halogen, $C_1$-$C_3$ alkyl, $OC_1$-$C_3$ alkyl, or trifluoromethyl; X=O or S; Y is O or S; Z is H, halogen, OH, CN, $CH_2CN$, $C_1$-$C_6$ alkyl, $C_3$-$C_6$ cycloalkyl, O—$C_1$-$C_6$ alkyl, ($CH_2$), $C_3$-$C_6$ cycloalkyl, O— $C_3$-$C_6$ cycloalkyl, O—($CH_2$)$_w$$C_3$-$C_6$ cycloalkyl, q=1 or 0; R5 is $C_1$-$C_6$ alkyl, ($CHR_6$)$_w$$C_3$-$C_6$ cycloalkyl, ($CHR_6$)$_w$$CH_2C_3$-$C_6$ cycloalkyl, $CH_2$($CHR_6$)$_w$$C_3$-$C_6$ cycloalkyl, ($CHR_6$)$_w$$C_5$-$C_6$ cycloalkenyl, $CH_2$($CHR_6$), $C_5$-$C_6$ cycloalkenyl, $C_2$-$C_6$ alkenyl, $C_2$-$C_6$ alkynyl, $Ar_2$, ($CHR_6$), $Ar_2$, $CH_2$($CHR_6$)$_w$$Ar_2$, or ($CHR_6$)$_w$$CH_2Ar_2$, where w=0-3, $Ar_2$ is a 5- to 10-member mono- or bicyclic aromatic group, optionally containing 1-4 ring heteroatoms selected independently from N, O, and S; $R_6$ is H or $C_1$-$C_3$ alkyl; and R8-R23 are, independently, H, $C_1$-$C_6$ alkyl, $C_3$-$C_6$ cycloalkyl, ($CHR_6$)$_w$$C_3$-$C_6$ cycloalkyl, $C_2$-$C_6$ alkenyl, $C_2$-$C_6$ alkenyl, $C_2$-$C_6$ alkynyl, where all alkyl, cycloalkyl, alkenyl, alkynyl, aryl, groups are optionally substituted with one or two substituents selected independently from $C_1$-$C_3$ alkyl, halogen, OH, OMe, CN, CH2F, and trifluoromethyl; where, additionally, the alkenyl and alkynyl groups are optionally substituted with phenyl or $C_3$-$C_6$ cycloalkyl; and where all cycloalkyl groups optionally contain one or two ring heteroatoms selected independently from N, O, and S. Such compounds are potassium channel modulators.

DETAILED DESCRIPTION OF THE INVENTION

In general, the compounds of the invention can be prepared by processes known in the chemical arts, particularly in light of the description contained herein. Certain processes for the manufacture of the compounds of the invention are provided as further features of the invention and are illustrated in the reaction schemes provided below and in the experimental results section. The use of various protecting groups in these reactions are also well known and are exemplified in Protective Groups In Organic Synthesis, Second Edition, T. W. Greene and P. G. M. Wuts, John Wiley and Sons, Inc. 1991, pages 227-229, which is hereby incorporated by reference in its entirety for all purposes.

The utility of the compounds of the invention as medical agents for modulating potassium channels and accordingly to treat disorders which are affected by activation of such channels, is demonstrated by the activity of the compounds in conventional assays, such as those described in the experimental and biological results section provided below. Such assays also provide a means whereby the activities of the compounds can be compared to each other and with the activities of other known compounds. The results of these comparisons are useful for determining dosage levels in mammals, including humans, for the treatment of such diseases.

As used herein, the terms "comprising" and "including" are used in their open, non-limiting sense.

As used herein, the term "substituted," means that the specified group or moiety bears one or more substituents. The term "unsubstituted," means that the specified group bears no substituents.

As used herein, the term "optionally substituted" means that the specified group is unsubstituted or is substituted by one or more substituents.

As used herein, the term "alkyl" means a straight or branched chain saturated hydrocarbon. Exemplary alkyl groups include but are not limited to methyl, ethyl, propyl, isopropyl, n-butyl, sec-butyl, tert-butyl, pentyl, isopentyl, neopentyl, tert-pentyl, 1-methylbutyl, 2-methylbutyl, 3-methylbutyl, hexyl, isohexyl, heptyl, octyl and the like.

As used herein, the term "alkenyl" means a straight or branched chain hydrocarbon having at least one double bond, i.e., a C=C. Exemplary alkenyl groups include but are not limited to vinyl, propenyl, butenyl, pentenyl, hexenyl, heptenyl, octenyl and the like.

As used herein, the term "alkynyl" means a straight or branched chain hydrocarbon having at least one triple bond, i.e., a C≡C. Exemplary alkynyl groups include but are not limited to acetylenyl, propargyl, butynyl, pentynyl, hexynyl, heptynyl, octynyl and the like.

As used herein, the term "cycloalkyl" means a cyclic saturated hydrocarbon. Exemplary cycloalkyl groups include but are not limited to cyclopropyl, cyclobutyl, cyclopentyl, cyclohexyl, cycloheptyl, cyclooctyl and the like.

As used herein, the term "cycloalkenyl" means a cyclic hydrocarbon having at least one double bond, i.e., a C=C. Exemplary cycloalkenyl groups include but are not limited to cyclopropenyl, cyclobutenyl, cyclopentenyl, cyclohexenyl, cycloheptenyl, cyclooctenyl and the like.

As used herein, the term "cycloalkenyl" means a cyclic hydrocarbon having at least one triple bond, i.e., a C≡C. Exemplary cycloalkynyl groups include but are not limited to cyclohexanyl, cycloheptenyl, cyclooctynyl and the like.

As used herein, the term "alkoxy" means a straight or branched chain saturated alkyl group bonded through oxygen. Exemplary alkoxy groups include but are not limited to methoxy, ethoxy, propoxy, isopropoxy, butoxy, isobutoxy, tert-butoxy, pentoxy, isopentoxy, neopentoxy, tert-pentoxy, hexoxy, isohexoxy, heptoxy, octoxy and the like.

As used herein, the term "alkylene" means a straight chain or branched chain saturated hydrocarbon wherein a hydrogen atom is removed from each of the terminal carbons. Exemplary alkylene groups include but are not limited to methylene, ethylene, propylene, butylene, pentylene, hexylene, heptylene and the like.

As used herein, the term "cycloalkylaryl" and "$(CH_2)_t(C_3$-$C_{12})$cycloalkyl$(C_6$-$C_{10})$aryl" includes linear and/or fused ring systems such as 2,3-dihydro-1H-indene, 2-methyl-2,3-dihydro-1H-indene, 1,2,3,4-tetrahydronaphthalene, 2-methyl-1,2,3,4-tetrahydronaphthalene, 1-cyclopentylbenzene, 1-(2-methylcyclopentyl)benzene, 1-(3-methylcyclopentyl)benzene, 1-cyclohexylbenzene, 1-(2-methylcyclohexyl)benzene, 1-(3-methylcyclohexyl)benzene, 1-(4-methylcyclohexyl)benzene, and the like As used herein, the term "halo" or "halogen" means fluoro, chloro, bromo or iodo.

As used herein, the term "aryl" means an organic radical derived from an aromatic hydrocarbon by removal of hydrogen. Exemplary aryl groups include but are not limited to phenyl, biphenyl, naphthyl, and the like.

As used herein, the terms "heterocyclic" and "heterocyclyl" means an aromatic or non-aromatic cyclic group containing one to four heteroatoms each independently selected from O, S and N, wherein each group has from 3 to 10 atoms in its ring system. Non-aromatic heterocyclic groups include groups having only 3 atoms in their ring system, whereas aromatic heterocyclic groups have at least 5 atoms in their ring system. Heterocyclic groups include fused ring systems such as benzo-fused rings and the like. an exemplary 3 membered heterocyclic group is aziridine; 4 membered heterocyclic group is azetidinyl (derived from azetidine); 5 membered heterocyclic group is thiazolyl; 7 membered ring heterocyclic group is azepinyl; and a 10 membered heterocyclic group is quinolinyl.

Examples of non-aromatic heterocyclic groups include but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxetanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

Examples of aromatic heterocyclic (heteroaryl) groups include but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The foregoing groups can be C-attached or N-attached where such is possible. For instance, a group derived from pyrrole can be pyrrol-1-yl (N-attached) or pyrrol-3-yl (C-attached). Further, a group derived from imidazole can be imidazol-1-yl (N-attached) or imidazol-3-yl (C-attached). Heterocyclic groups can be optionally substituted on any ring carbon, sulfur or nitrogen atom(s) by one to two oxygens (oxo), per ring. An example of a heterocyclic group wherein 2 ring carbon atoms are substituted with oxo moieties is 1,1-dioxo-thiomorpholinyl.

Exemplary five to six membered heterocyclic aromatic rings having one or two heteroatoms selected independently from oxygen, nitrogen and sulfur include but are not limited to isothiazolyl, pyridinyl, pyridazinyl, pyrimidinyl, pyrazinyl and the like.

Exemplary partially saturated, fully saturated or fully unsaturated five to eight membered heterocyclic rings having one to four heteroatoms selected independently from oxygen, sulfur and nitrogen include but are not limited to 3H-1,2-oxathiolyl, 1,2,3-oxadiazolyl, 1,2,4-oxadiazolyl, 1,2,5-oxadiazolyl and the like. Further exemplary five membered rings are furyl, thienyl, 2H-pyrrolyl, 3H-pyrroyl, pyrrolyl, 2-pyrrolinyl, 3-pyrrolinyl, pyrrolidinyl, 1,3-dioxolanyl, oxazolyl, thiazolyl, thiazolyl, imidazolyl, 2H-imidazolyl, 2-imidazolinyl, imidazolidinyl, pyrazolyl, 2-pyrazolinyl, pyrazolinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl. Further exemplary six member rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl. Further exemplary seven membered rings are azepinyl, oxepinyl, thiepinyl and 1,2,4-diazepinyl. Further exemplary eight membered rings are cyclooctyl, cyclooctenyl and cyclooctadienyl.

Exemplary bicyclic rings are composed of two fused partially saturated, fully saturated or fully unsaturated five or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, 4H quinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

Exemplary 3-10 membered heterocyclyl groups include but are not limited to oxetane, azetidine, tetrahydrofuran, pyrrolidine, 2,5-dihydro-1H-pyrrole, 1,3-dioxolane, isoxazolidine, oxazolidine, pyrazolidine, imidazolidine, pyrrolidin-2-one, tetrahydrothiophene-1,1-dioxide, pyrrolidine-2,5-dione, tetrahydro-2H-pyran, piperidine, 1,2,3,6-tetrahydropyridine, 1,4-dioxane, morpholine, piperazine, thiomorpholine, piperidin-2-one, piperidin-4-one, thiomorpholine-1,1-dioxide, 1,3-oxazinan-2-one, morpholin-3-one, piperazine-2-one, azepane, 1,4-oxazepine, 1,4-diazepine, azepan-2-one, 1,4-diazepane-5-one, quinuclidine, 2-aza-bicyclo[2.2.1]heptane, 8-aza-bicyclo[3.2.1]octane, 5-oxa-2-aza-bicyclo[2.2.1]heptane, 2-oxa-5-aza-bicyclo[2.2.1]heptan-3-one, 2-oxa-5-aza-bicyclo[2.2.2]octan-3-one, 1-methyl-5,6-pyrrolyl-7-oxa-bicyclo[2.2.1]heptane, 6-aza-bicyclo[3.2.1]octane, 3,8-diaza-bicyclo[3.2.1]octan-2-one, 2,2-dimethyl-tetrahydro-3aH-[1,3]dioxolo[4,5-c]pyrrole, 3,3-cyclohexylpyrrolidone, 1,5-diaxo-9-azaspiro[5.5]undecane, octahydro-1H-isoindole, decahydroquinoline, decahydroisoquinoline, octahydropyrrolo[1,2a]pyrazine, octahydro'1H-pyrido[1,2a]pyrazine, octahydropyrrolo[3,4-c]pyridine-3-one, decahydropyrazino[1,2-a]azepine, furan, 1H-pyrrole, isoxazole, oxazole, 1H-pyrazole, 1H-imidazole, thiazole, 1,2,4-oxadiazole, 1,3,4-oxadiazole, 4H-1,2,4-triazole, 1H-tetrazole, pyridine, pyridazine, pyrimidine, pyrazine, pyridine-2(1H)-one, 1,4,5,6-tetrahydrocyclopenta[c]pyrazole, 6,7-dihydro-5H-pyrrolo[2,1-c][1,2,4]triazole, 2,3-dihydroimidazo[2,1-b]thiazole, imidazo[2,1-b][1,3,4-c]pyridine, 4,5,6,7-tetrahydro-3H-imidazo[4,5-c]pyridine, 5,6,7,8-tetrahydroimidazo[1,5-a]pyrazine, 4,5,6,7-tetrahydrothiazole[5,4-c]pyridine, 5,6,7,8-tetrahydro-[1,2,4]triazolo[4,3-a]pyrazine, quinoline, isoquinoline, 2,3-dihydrobenzofuran, 5,6,7,8-tetrahydroquinoline, 3,4-dihydro-1H-isochromene, 1,2,3,4-tetrahydroisoquinoline, 4H-benzo[d][1,3]dioxane, 5,6,7,8-tetrahydropyrido[3,4-d]pyrimidine, benzofuran, 1H-indole, benzo[d]oxazole, 1H-benzo[d]imidazole, H-imidazo[1,2-a]pyridine, imidazo[1,2-a]pyrimidine, 5,6,7,8-tetrahydroimidazo[1,5-a]pyrazine-3(2H)-one, 2,3,4,5-tetrahydro-1H-benzo[d]azepine, 2,3,4,5-tetrahydrobenzo[f][1,4]oxazepine, 5,6,7,8-tetrahydro-4H-isoxazolo[4,3-d]azepine and 6,7,8,9-tetrahydro-2H-[1,2,4]triazolo[4,3-g][1,4]diazepin-3(5H)-one.

It is to be understood that if a carbocyclic or heterocyclic moiety can be bonded or otherwise attached to a designated substrate, through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

As used herein, the terms "treat," "treating" or "treatment" includes preventative (e.g., prophylactic) and palliative treatment.

As used herein, the term "pharmaceutically acceptable" is intended to mean that a referenced component such as a salt, ester or solvate is physiologically tolerable at doses to be administered. Pharmaceutically acceptable salts, esters solvates, carriers, diluents, syrups and the like are well known to those skilled in the art.

For example, the term "pharmaceutically acceptable acid salts" refers to acid addition salts formed from acids which provide non-toxic anions. The pharmaceutically acceptable anions include, but are not limited to, acetate, aspartate, benzoate, bicarbonate, carbonate, bisulfate, sulfate, chloride, bromide, benzene sulfonate, methyl sulfonate, phosphate, acid phosphate, lactate, maleate, malate, malonate, fumarate, lactate, tartrate, borate, camsylate, citrate, edisylate, esylate, formate, fumarate, gluceptate, glucuronate, gluconate oxalate, palmitate, pamoate, saccharate, stearate, succinate, tartrate, tosylate and trifluoroacetate salts, among a great many other examples. Hemi-salts, including but not limited to hemi-sulfate salts, are likewise directed to the invention. For a review on suitable salts, see "Handbook of Pharmaceutical Salts Properties, Selection, and Use" by Stahl and Wermuth (Wiley-VCH, Weinheim, Germany, 2002).

Pharmaceutically acceptable salts of the compounds of the invention include the acid addition and base salts (including disalts) thereof. Pharmaceutically acceptable salts of compounds of formula I can be prepared by reaction of a compound of formula I with the desired acid; by removal of a protecting group from a suitable precursor of the compound of formula I or by ring-opening a suitable cyclic precursor, for example, a lactone or lactam, using the desired acid or base; and by conversion of one salt of the compound of formula I to another by reaction with an appropriate acid or base or by passage through an appropriate ion-exchange column.

For example, suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002).

As used herein, the term pharmaceutically acceptable carrier comprises such excipients, binders, lubricants, tabletting agents, disintegrants, preservatives, anti-oxidants, flavors and colorants as are typically used in the art of formulation of pharmaceuticals. Examples of such agents include—but are not limited to—starch, calcium carbonate, dibasic calcium phosphate, dicalcium phosphate, microcrystalline cellulose, hydroxypropylcellulose, hydroxypropylmethylcellulose lactose, polyethylene glycols, polysorbates, glycols, safflower oil, sesame oil, soybean oil, and Povidone. Additionally, disintegrants such as sodium starch glycolate; lubricants such as magnesium stearate, stearic acid, and $SiO_2$; and solubility enhancers such as cyclodextrins, among a great many other examples for each group, are directed to the invention. Such materials and the methods of using them are well known in the pharmaceutical art. Additional examples are provided in Kibbe, *Handbook of Pharmaceutical Excipients*, London, Pharmaceutical Press, 2000.

As used herein, the term "pharmaceutically acceptable solvate" refers to describe a molecular complex comprising the compound of the invention and a stoichiometric amount of one or more pharmaceutically acceptable solvent molecules, including but not limited to water and ethanol. Thus, the term solvate includes a hydrate as one example and an ethanolate as another example.

As used herein, the term "hyperexcitability" when used in reference to a disorder of the nervous system is intended to mean a neuromuscular condition characterized by excessive neuronal activity. Such excessive activity can include, for example, spontaneous neuronal activity or excessive activity in response to physiological stimuli. Diseases characterized by hyperexcitability of the nervous system are well known in the art and include, for example, epilepsy, bipolar disorder, migraine, other seizure disorders and neuropathic pain. The compounds of the invention are applicable for the treatment of disorders characterized by hyperexcitability of the nervous system through voltage modulation of KCNQ potassium ($K^+$) channels.

As used herein, the term "therapeutically effective amount" is intended to mean the amount or dose of a compound of the invention that can reduce or ameliorate at least one symptom of a disorder characterized by hyperexcitability of the nervous system. A therapeutically effective amount includes the amount of a compound of the invention required to modulate KCNQ2/3 ion channels following administering to a subject. Modulation includes activation or inhibition of KCNQ2/3 ion channels, which can be determined using methods well known in the art such as those exemplified below in the Examples.

The following non-limiting preparations and Examples illustrate the preparation of the compounds of the invention.

In one embodiment, the invention provides a composition comprising a pharmaceutically acceptable carrier or diluent and at least one of the following: a pharmaceutically effective amount of a compound of formula I, a pharmaceutically acceptable salt of a compound of formula I, a pharmaceutically acceptable solvate of a compound of formula I, and a pharmaceutically acceptable ester of a compound of formula I.

In another embodiment, the invention provides a pediatric pharmaceutical composition comprising a pharmaceutically acceptable carrier or diluent, a syrup for pediatric use, and at least one of the following: a pharmaceutically effective amount of a compound of formula I, a pharmaceutically acceptable salt of a compound of formula I, a pharmaceutically acceptable ester of a compound of formula I, and a pharmaceutically acceptable solvate of a compound of formula I.

In yet another embodiment, the invention provides to a chewable tablet, suitable for pediatric pharmaceutical use, comprising a pharmaceutically acceptable carrier or diluent, and at least one of the following: a pharmaceutically effective amount of a compound of formula I, a pharmaceutically acceptable salt of a compound of formula I, a pharmaceutically acceptable solvate of a compound of formula I, and a pharmaceutically acceptable ester of a compound of formula I.

This invention includes all tautomers and salts of compounds of this invention. This invention also includes all compounds of this invention where one or more atoms are replaced by a radioactive isotope thereof.

In one embodiment, the invention provides a compound of formula I, where NH—C(=X)—(Y)$_q$—R$_5$ is NHC(=O)R$_5$.

In another embodiment, the invention provides a compound of formula I, where NH—C(=X)—(Y)$_q$—R$_5$ is NHC(=O)OR$_5$.

In another embodiment, the invention provides a compound of formula I, where NH—C(=X)—(Y)$_q$—R$_5$ is NHC(=S)SR$_5$.

In another embodiment, the invention provides a compound of formula I, where NH—C(=X)—(Y)$_q$—R$_5$ is NHC(=S)R$_5$.

In another embodiment, the invention provides a compound of formula I, where NH—C(=X)—(Y)$_q$—R$_5$ is NHC(=S)OR$_5$.

In another embodiment, the invention provides a compound of formula I, where NH—C(=X)—(Y)$_q$—R$_5$ is NHC(=O)SR$_5$.

In a more specific embodiment, the invention provides a compound of formula I, where n is 1 and NH—C(=X)—(Y)$_q$—R$_5$ is NHC(=O)R$_5$.

In another more specific embodiment, the invention provides a compound of formula I, where n is 1 and NH—C(=X)—(Y)$_q$—R$_5$ is NHC(=O)OR$_5$.

In another more specific embodiment, the invention provides a compound of formula I, where n is 1 and NH—C(=X)—(Y)$_q$—R$_5$ is NHC(=S)SR$_5$.

In another more specific embodiment, the invention provides a compound of formula I, where n is 1 and NH—C(=X)—(Y)$_q$—R$_5$ is NHC(=S)R$_5$.

In another more specific embodiment, the invention provides a compound of formula I, where n is 1 and NH—C(=X)—(Y)$_q$—R$_5$ is NHC(=S)OR$_5$.

In another more specific embodiment, the invention provides a compound of formula I, where n is 1 and NH—C(=X)—(Y)$_q$—R$_5$ is NHC(=O)SR$_5$.

In another more specific embodiment, the invention provides a compound of formula I, where n is 2 and NH—C(=X)—(Y)$_q$—R$_5$ is NHC(=O)R$_5$.

In another more specific embodiment, the invention provides a compound of formula I, where n is 2 and NH—C(=X)—(Y)$_q$—R$_5$ is NHC(=O)OR$_5$.

In another more specific embodiment, the invention provides a compound of formula I, where n is 2 and NH—C(=X)—(Y)$_q$—R$_5$ is NHC(=S)SR$_5$.

In another more specific embodiment, the invention provides a compound of formula I, where n is 2 and NH—C(=X)—(Y)$_q$—R$_5$ is NHC(=S)R$_5$.

In another more specific embodiment, the invention provides a compound of formula I, where n is 2 and NH—C(=X)—(Y)$_q$—R$_5$ is NHC(=S)OR$_5$.

In another more specific embodiment, the invention provides a compound of formula I, where n is 2 and NH—C(=X)—(Y)$_q$—R$_5$ is NHC(=O)SR$_5$.

In another more specific embodiment, the invention provides a compound of formula I, where n is 3 and NH—C(=X)—(Y)$_q$—R$_5$ is NHC(=O)R$_5$.

In another more specific embodiment, the invention provides a compound of formula I, where n is 3 and NH—C(=X)—(Y)$_q$—R$_5$ is NHC(=O)OR$_5$.

In another more specific embodiment, the invention provides a compound of formula I, where n is 3 and NH—C(=X)—(Y)$_q$—R$_5$ is NHC(=S)SR$_5$.

In another more specific embodiment, the invention provides a compound of formula I, where n is 3 and NH—C(=X)—(Y)$_q$—R$_5$ is NHC(=S)R$_5$.

In another more specific embodiment, the invention provides a compound of formula I, where n is 3 and NH—C(=X)—(Y)$_q$—R$_5$ is NHC(=S)OR$_5$.

In another more specific embodiment, the invention provides a compound of formula I, where n is 3 and NH—C(=X)—(Y)$_q$—R$_5$ is NHC(=O)SR$_5$.

In another embodiment, the invention provides a compound of formula I, where U is CR' and R' is H, halogen, trifluoromethyl, or methyl.

In another embodiment, the invention provides a compound of formula I, where Z is H, halogen, trifluoromethyl, or methyl.

In another embodiment, the invention provides a compound of formula I, where Z is H, halogen, $C_1$-$C_6$ alkyl, O—$C_1$-$C_6$ alkyl, $CF_3$, $OCF_3$, or $C_3$-$C_6$ cycloalkyl.

In another embodiment, the invention provides a compound of formula I, where Z is H, OH, CN, $CH_2CN$, $OCH_3$, or $CH_2OCH_3$.

In a more specific embodiment, the invention provides a compound of formula I, where NH—C(=X)—(Y)$_q$—R$_5$ is NHC(=O)R$_5$ and Z is H, halogen, $C_1$-$C_6$ alkyl, O—$C_1$-$C_6$ alkyl, $CF_3$, $OCF_3$, or $C_3$-$C_6$ cycloalkyl.

In a still more specific embodiment, the invention provides a compound of formula I, where NH—C(=X)—(Y)$_q$—R$_5$ is NHC(=O)R$_5$; n is 1; $R_3$ and $R_4$ are, independently, H, methyl, ethyl, trifluoromethyl, Cl, Br, or F; and Z is H, halogen, $C_1$-$C_6$ alkyl, O—$C_1$-$C_6$ alkyl, $CF_3$, $OCF_3$, or $C_3$-$C_6$ cycloalkyl.

In a still more specific embodiment, the invention provides a compound of formula I, where NH—C(=X)—(Y)$_q$—R$_5$ is NHC(=O)R$_5$; n is 2; $R_3$ and $R_4$ are, independently, H, methyl, ethyl, trifluoromethyl, Cl, Br, or F; and Z is H, halogen, $C_1$-$C_6$ alkyl, O—$C_1$-$C_6$ alkyl, $CF_3$, $OCF_3$, or $C_3$-$C_6$ cycloalkyl.

In a still more specific embodiment, the invention provides a compound of formula I, where NH—C(=X)—(Y)$_q$—R$_5$ is NHC(=O)R$_5$; n is 3; $R_3$ and $R_4$ are, independently, H, methyl, ethyl, trifluoromethyl, Cl, Br, or F; and Z is H, halogen, $C_1$-$C_6$ alkyl, O—$C_1$-$C_6$ alkyl, $CF_3$, $OCF_3$, or $C_3$-$C_6$ cycloalkyl.

In a still more specific embodiment, the invention provides a compound of formula I, where NH—C(=X)—(Y)$_q$—R$_5$ is NHC(=O)OR$_5$; n is 1; $R_3$ and $R_4$ are, independently, H, methyl, ethyl, trifluoromethyl, Cl, Br, or F; and Z is H, halogen, $C_1$-$C_6$ alkyl, O—$C_1$-$C_6$ alkyl, $CF_3$, $OCF_3$, or $C_3$-$C_6$ cycloalkyl.

In a still more specific embodiment, the invention provides a compound of formula I, where NH—C(=X)—(Y)$_q$—R$_5$ is NHC(=O)OR$_5$; n is 2; $R_3$ and $R_4$ are, independently, H, methyl, ethyl, trifluoromethyl, Cl, Br, or F; and Z is H, halogen, $C_1$-$C_6$ alkyl, O—$C_1$-$C_6$ alkyl, $CF_3$, $OCF_3$, or $C_3$-$C_6$ cycloalkyl.

In a still more specific embodiment, the invention provides a compound of formula I, where NH—C(=X)—(Y)$_q$—R$_5$ is NHC(=O)OR$_5$; n is 3; $R_3$ and $R_4$ are, independently, H, methyl, ethyl, trifluoromethyl, Cl, Br, or F; and Z is H, halogen, $C_1$-$C_6$ alkyl, O—$C_1$-$C_6$ alkyl, $CF_3$, $OCF_3$, or $C_3$-$C_6$ cycloalkyl.

In another still more specific embodiment, the invention provides a compound of formula I, where X is O, q is zero, R5 is tert-butyl or neopentyl, and Z is H, halogen, methyl, or trifluoromethyl.

In another still more specific embodiment, the invention provides a compound of formula I, where X is O, q is 1, Y is O, $R_5$ is tert-butyl or neopentyl, and Z is H, halogen, methyl, or trifluoromethyl.

In a still more specific embodiment, the invention provides a compound of formula I, where X is O, q is zero, $R_5$ is $(CHR_6)_wC_3$-$C_6$ cycloalkyl, $(CHR_6)_wCH_2C_3$-$C_6$ cycloalkyl, $CH_2(CHR_6)_wC_3$-$C_6$ cycloalkyl, $(CHR_6)_wC_5$-$C_6$ cycloalkenyl, or $CH_2(CHR_6)_wC_5$-$C_6$ cycloalkenyl; and Z is H, halogen, methyl, or trifluoromethyl.

In another still more specific embodiment, the invention provides a compound of formula I, where X is O, q is 1, Y is O, $R_5$ is $(CHR_6)_wC_3$-$C_6$ cycloalkyl, $(CHR_6)_wCH_2C_3$-$C_6$ cycloalkyl, $CH_2(CHR_6)$, $C_3$-$C_6$ cycloalkyl, $(CHR_6)_wC_5$-$C_6$ cycloalkenyl, or $CH_2(CHR_6)_wC_5$-$C_6$ cycloalkenyl; and Z is H, halogen, methyl, or trifluoromethyl.

In a still more specific embodiment, the invention provides a compound of formula I, where X is O, q is zero, $R_5$ is $C_2$-$C_6$ alkenyl, $C_2$-$C_6$ alkynyl, or $Ar_2$; and Z is H, halogen, methyl, or trifluoromethyl.

In another still more specific embodiment, the invention provides a compound of formula I, where X is O, q is 1, Y is O, $R_5$ is $C_2$-$C_6$ alkenyl, $C_2$-$C_6$ alkynyl, or $Ar_2$; and Z is H, halogen, methyl, or trifluoromethyl.

In a still more specific embodiment, the invention provides a compound of formula I, where X is O, q is zero, $R_5$ is $(CHR_6)_wAr_2$, $CHACHR_6)_wAr_2$, or $(CHR_6)_wCH_2Ar_2$, and Z is H, halogen, methyl, or trifluoromethyl.

In another still more specific embodiment, the invention provides a compound of formula I, where X is O, q is 1, Y is O, $R_5$ is $(CHR_6)_wAr_2$, $CH_2(CHR_6)_wAr_2$, or $(CHR_6)_wCH_2Ar_2$, and Z is H, halogen, methyl, or trifluoromethyl.

In another still more specific embodiment, the invention provides a compound of formula I, where X is O, q is zero, $R_5$ is tert-butyl or neopentyl; $R_1$ is halogen, methyl, trifluoromethyl, methoxy, or trifluoromethoxy; and Z is H, halogen, methyl, or trifluoromethyl.

In another still more specific embodiment, the invention provides a compound of formula I, where X is O, q is 1, Y is O, $R_5$ is tert-butyl or neopentyl; $R_1$ is halogen, methyl, trifluoromethyl, methoxy, or trifluoromethoxy; and Z is H, halogen, methyl, or trifluoromethyl.

In an embodiment, the invention provides compounds of formula I-N,

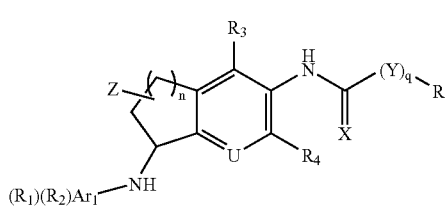

I-N

In another embodiment, the invention provides compounds of formula I-O,

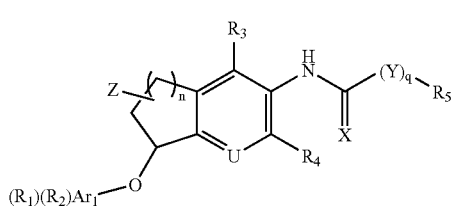

I-O

In another embodiment, the invention provides compounds of formula I-S,

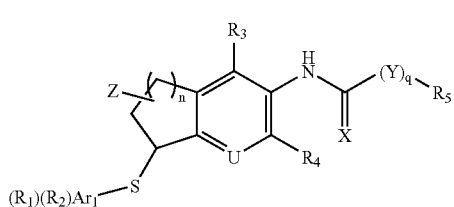

I-S

In another embodiment, the invention provides compounds of formula I-Cgg,

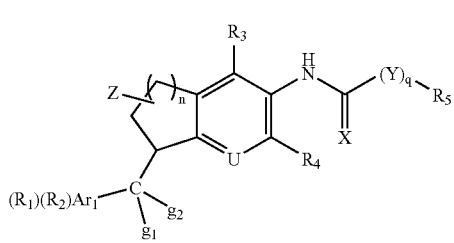

I-Cgg

In one embodiment, the invention provides a compound of formula I-N, where NH—C(=X)—(Y)$_q$—R$_5$ is NHC(=O)R$_5$.

In another embodiment, the invention provides compound of formula I-N, where NH—C(=X)—(Y)$_q$—R$_5$ is NHC(=O)OR$_5$.

In another embodiment, the invention provides a compound of formula I-N, where NH—C(=X)—(Y)$_q$—R$_5$ is NHC(=S)SR$_5$.

In another embodiment, the invention provides a compound of formula I-N, where NH—C(=X)—(Y)$_q$—R$_5$ is NHC(=S)R$_5$.

In another embodiment, the invention provides a compound of formula I-N, where NH—C(=X)—(Y)$_q$—R$_5$ is NHC(=S)OR$_5$.

In another embodiment, the invention provides a compound of formula I-N, where NH—C(=X)—(Y)$_q$—R$_5$ is NHC(=O)SR$_5$.

In one embodiment, the invention provides a compound of formula I-O, where NH—C(=X)—(Y)$_q$—R$_5$ is NHC(=O)R$_5$.

In another embodiment, the invention provides a compound of formula I-O, where NH—C(=X)—(Y)$_q$—R$_5$ is NHC(=O)OR$_5$.

In another embodiment, the invention provides a compound of formula I-O, where NH—C(=X)—(Y)$_q$—R$_5$ is NHC(=S)SR$_5$.

In another embodiment, the invention provides compound of formula I-O, where NH—C(=X)—(Y)$_q$—R$_5$ is NHC(=S)R$_5$.

In another embodiment, the invention provides a compound of formula I-O, where NH—C(=X)—(Y)$_q$—R$_5$ is NHC(=S)OR$_5$.

In another embodiment, the invention provides a compound of formula I-O, where NH—C(=X)—(Y)$_q$—R$_5$ is NHC(=O)SR$_5$.

In one embodiment, the invention provides a compound of formula I-S, where NH—C(=X)—(Y)$_q$—R$_5$ is NHC(=O)R$_5$.

In another embodiment, the invention provides a compound of formula I-S, where NH—C(=X)—(Y)$_q$—R$_5$ is NHC(=O)OR$_5$.

In another embodiment, the invention provides a compound of formula I-S, where NH—C(=X)—(Y)$_q$—R$_5$ is NHC(=S)SR$_5$.

In another embodiment, the invention provides a compound of formula I-S, where NH—C(=X)—(Y)$_q$—R$_5$ is NHC(=S)R$_5$.

In another embodiment, the invention provides a compound of formula I-S, where NH—C(=X)—(Y)$_q$—R$_5$ is NHC(=S)OR$_5$.

In another embodiment, the invention provides a compound of formula I-S, where NH—C(=X)—(Y)$_q$—R$_5$ is NHC(=O)SR$_5$.

In one embodiment, the invention provides a compound of formula I-Cgg, where NH—C(=X)—(Y)$_q$—R$_5$ is NHC(=O)R$_5$.

In another embodiment, the invention provides a compound of formula I-Cgg, where NH—C(=X)—(Y)$_q$—R$_5$ is NHC(=O)OR$_5$.

In another embodiment, the invention provides a compound of formula I-Cgg, where NH—C(=X)—(Y)$_q$—R$_5$ is NHC(=S)SR$_5$.

In another embodiment, the invention provides a compound of formula I-Cgg, where NH—C(=X)—(Y)$_q$—R$_5$ is NHC(=S)R$_5$.

In another embodiment, the invention provides a compound of formula I-Cgg, where NH—C(=X)—(Y)$_q$—R$_5$ is NHC(=S)OR$_5$.

In another embodiment, the invention provides a compound of formula I-Cgg, where NH—C(=X)—(Y)$_q$—R$_5$ is NHC(=O)SR$_5$.

In another embodiment, the invention provides a compound of formula I-A

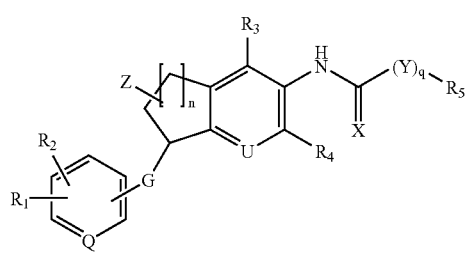

I-A where Q=CR7 or N, where R7 is H or $C_1$-$C_6$ alkyl.

In another embodiment, the invention provides compounds of formula I-N-A,

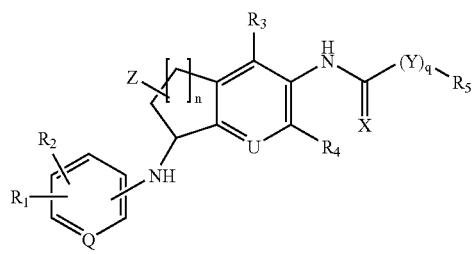

I-N-A

In another embodiment, the invention provides a compound of formula IB,

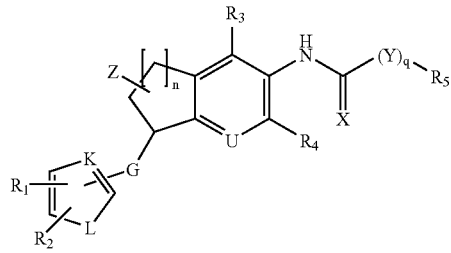

IB where L is O, S, or NH, and K is N or CH.

In another embodiment, the invention provides a compound of formula I-O-B,

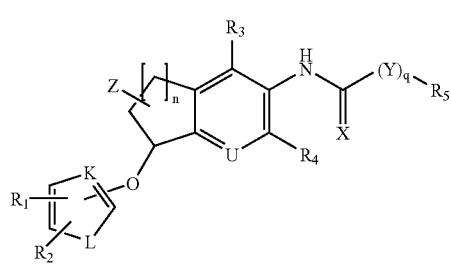

I-O-B

In another embodiment, the invention provides a compound of formula I-S-B,

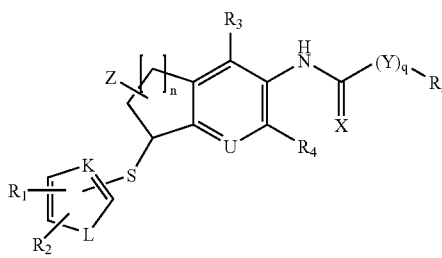

I-S-B

In another embodiment, the invention provides a compound of formula I-Cgg-B,

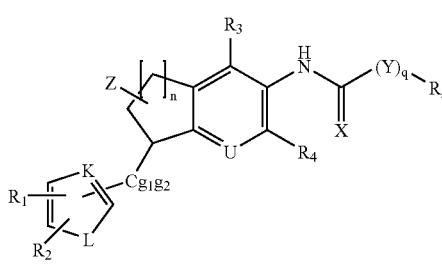

I-Cgg-B

In another embodiment, the invention provides a compound of formula I-N-B.

I-N-B

In more specific embodiments, the invention provides compounds of formulas I-N-B-1 and I-N-B-2.

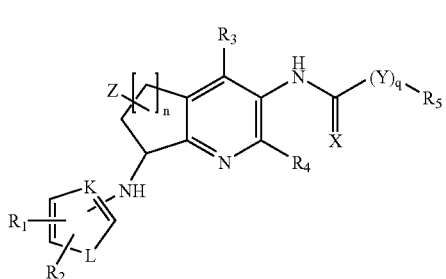

I-N-B-1

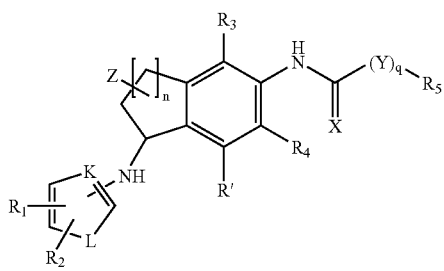
I-N-B-2

In additional embodiments, the invention provides a compound of formula IC-1 or IC-2

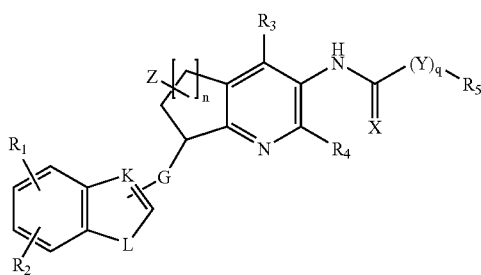
IC-1

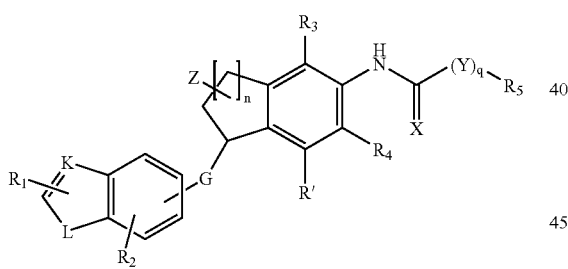
IC-2 where L is O, S, or NH, and K is N or CH.

In additional embodiments, the invention provides a compound of formula I-N-C-1 or I-N-C-2,

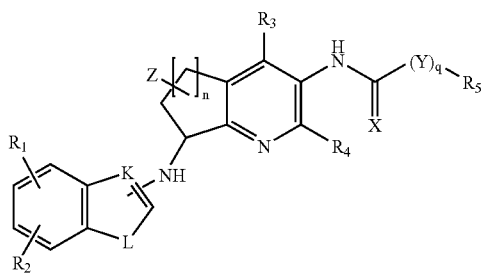
I-N-C-1

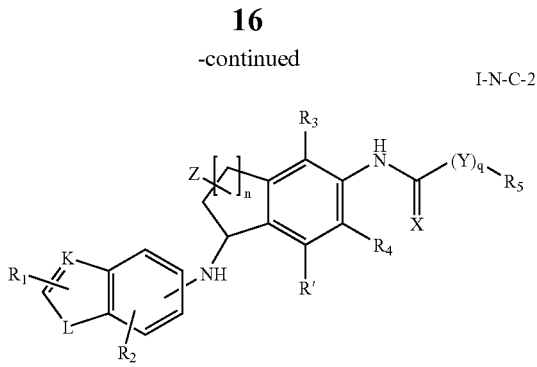
I-N-C-2 where L is O, S, or NH, and K is N or CH.

In other embodiments, this invention provides compounds of formulas I-O-C-1 and 1-O-C-2, which are compounds of formula IC-1 and IC-2 where G is O.

In other embodiments, this invention provides compounds of formulas I-S-C-1 and I-S-C-2, which are compounds of formula IC-1 and IC-2 where G is S.

In other embodiments, this invention provides compounds of formulas I-Cgg-C-1 and 1-Cgg-C-2, which are compounds of formula IC-1 and IC-2 where G is C(gi)(g2).

In another embodiment, the invention provides a compound of formula ID-1 or ID-2,

ID-1

ID-2 where K and L are, independently, N or CH.

In a more specific embodiment, the invention provides a compound of formula I-N-D-1 or I-N-D-2,

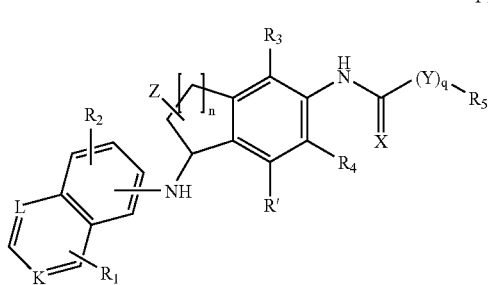
I-N-D-1

-continued

I-N-D-2 where K and L are, independently, N or CH.

In additional embodiments, this invention provides compounds of formulas I-O-D-1 and I-O-D-2, which are compounds of formulas ID-1 and ID-2, where G is O.

In additional embodiments, this invention provides compounds of formulas I-S-D-1 and I-S-D-2, which are compounds of formulas ID-1 and ID-2, where G is S.

In additional embodiments, this invention provides compounds of formulas I-Cgg-D-1 and I-Cgg-D-2, which are compounds of formulas ID-1 and ID-2, where G is $C(g_1)(g_2)$.

In a more specific embodiment, the invention provides compounds of formula IA, where NH—C(=X)—$(Y)_q$—$R_5$ is NHC(=O)$R_5$ or NHC(=O)O$R_5$.

In a still more specific embodiment, the invention provides compounds of formula I-N-A, where NH—C(=X)—$(Y)_q$—$R_5$ is NHC(=O)$R_5$ or NHC(=O)O$R_5$.

In another still more specific embodiment, the invention provides compounds of formula I-O-A, where NH—C(=X)—$(Y)_q$—$R_5$ is NHC(=O)$R_5$ or NHC(=O)O$R_5$.

In another still more specific embodiment, the invention provides compounds of formula I-S-A, where NH—C(=X)—$(Y)_q$—$R_5$ is NHC(=O)$R_5$ or NHC(=O)O$R_5$.

In another still more specific embodiment, the invention provides compounds of formula I-Cgg-A, where NH—C(=X)—$(Y)_q$—$R_5$ is NHC(=O)$R_5$ or NHC(=O)O$R_5$.

In a still more specific embodiment, the invention provides a compound of formula IA, where X is O, q is zero, R5 is tert-butyl or neopentyl; $R_1$ is halogen, methyl, trifluoromethyl, methoxy, or trifluoromethoxy; and Z is H, halogen, methyl, or trifluoromethyl.

In another still more specific embodiment, the invention provides a compound of formula IA, where X is O, q is 1, Y is O, $R_5$ is tert-butyl or neopentyl; $R_1$ is halogen, methyl, trifluoromethyl, methoxy, or trifluoromethoxy; and Z is H, halogen, methyl, or trifluoromethyl.

In another still more specific embodiment, the invention provides a compound of formula IA, where X is O, q is zero, R5 is tert-butyl or neopentyl; U is CR'; R' is H, halogen, trifluoromethyl, or methyl; $R_1$ is halogen, methyl, trifluoromethyl, methoxy, or trifluoromethoxy; and Z is H, halogen, methyl, or trifluoromethyl.

In another still more specific embodiment, the invention provides a compound of formula IA, where X is O, q is 1, Y is O, $R_5$ is tert-butyl or neopentyl; U is CR; R' is H, halogen, trifluoromethyl, or methyl; $R_1$ is halogen, methyl, trifluoromethyl, methoxy, or trifluoromethoxy; and Z is H, halogen, methyl, or trifluoromethyl.

In another more specific embodiment, the invention provides compounds of formula IA, where NH—C(=X)—$(Y)_q$—$R_5$ is NHC(=S)$R_5$ or NHC(=S)S$R_5$.

In another more specific embodiment, the invention provides compounds of formula IA, where NH—C(=X)—$(Y)_q$—$R_5$ is NHC(=S)O$R_5$. or NHC(=O)S$R_5$.

In another more specific embodiment, the invention provides compounds of formula IA, where NH—C(=X)—$(Y)_q$—$R_5$ is NHC(=O)$R_5$ or NHC(=O)O$R_5$.

In another more specific embodiment, the invention provides compounds of formula IA, where NH—C(=X)—$(Y)_q$—$R_5$ is NHC(=S)$R_5$ or NHC(=S)S$R_5$.

In another more specific embodiment, the invention provides compounds of formula IA, where NH—C(=X)—$(Y)_q$—$R_5$ is NHC(=S)O$R_5$ or NHC(=O)S$R_5$.

In more specific embodiments, the invention provides compounds of formula IA according to the structures below

IA-1

IA-2

IA-3

IA-4

-continued

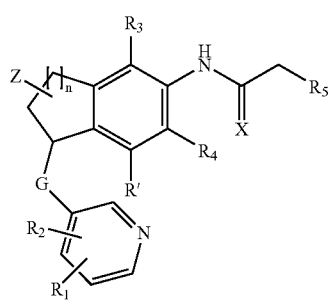

In still more specific embodiments, the invention provides compounds of formulas IA-1, IA-2, IA-3, IA-4, IA-5, IA-6, IA-7, and IA-8, where X is S.

In additional still more specific embodiments, the invention provides compounds of formulas IA-1, IA-2, IA-3, IA-4, IA-5, IA-6, IA-7, and IA-8, where X is O.

In still more specific embodiments, the invention provides compounds of formulas IA-3, IA-4, IA-7, and IA-8, in which X is S and Y is S.

In still more specific embodiments, the invention provides compounds of formulas IA-3, IA-4, IA-7, and IA-8, in which X is O and Y is S.

In still more specific embodiments, the invention provides compounds of formulas IA-3, IA-4, IA-7, and IA-8, in which X is S and Y is O.

In still more specific embodiments, the invention provides compounds of formulas IA-3, IA-4, IA-7, and IA-8, in which X is O and Y is O.

In even more specific embodiments, the invention provides compounds of formula IA according to the structures below

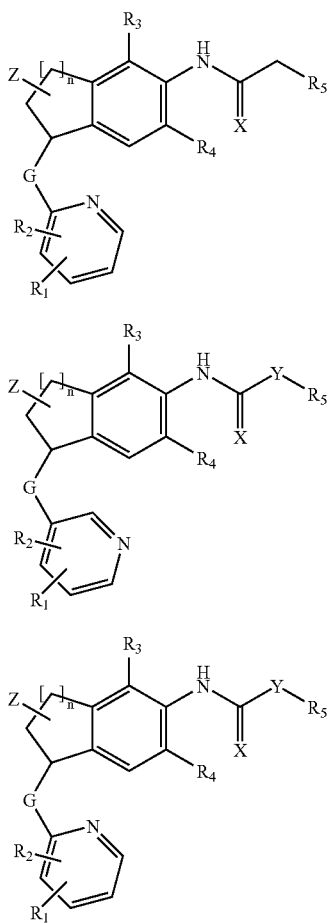

IA-6a

IA-7a

IA-8a

In another still more specific embodiment, the invention provides a compound of formula IB, where X is O, q is 1, Y is O, $R_5$ is tert-butyl or neopentyl; U is CR'; R' is H, halogen, trifluoromethyl, or methyl; $R_1$ is halogen, methyl, trifluoromethyl, methoxy, or trifluoromethoxy; and Z is H, halogen, methyl, or trifluoromethyl.

In another more specific embodiment, the invention provides compounds of formula IB, where NH—C(=X)—$(Y)_q$—$R_5$ is NHC(=S)$R_5$ or NHC(=S)S$R_5$.

In another more specific embodiment, the invention provides compounds of formula IB, where NH—C(=X)—$(Y)_q$—$R_5$ is NHC(=S)O$R_5$ or NHC(=O)S$R_5$.

In another more specific embodiment, the invention provides compounds of formula IB, where NH—C(=X)—$(Y)_q$—$R_5$ is NHC(=O)$R_5$ or NHC(=O)O$R_5$.

In another more specific embodiment, the invention provides compounds of formula IB, where NH—C(=X)—$(Y)_q$—$R_5$ is NHC(=S)$R_5$ or NHC(=S)S$R_5$.

In another more specific embodiment, the invention provides compounds of formula IB, where NH—C(=X)—$(Y)_q$—$R_5$ is NHC(=S)O$R_5$. or NHC(=O)S$R_5$.

In another more specific embodiment, the invention provides compounds of formula IC-1 or IC-2, where NH—C(=X)—$(Y)_q$—$R_5$ is NHC(=O)$R_5$ or NHC(=O)O$R_5$.

In another more specific embodiment, the invention provides compounds of formula IC-1 or IC-2, where NH—C(=X)—$(Y)_q$—$R_5$ is NHC(=S)$R_5$ or NHC(=S)S$R_5$.

In another more specific embodiment, the invention provides compounds of formula IC-1 or IC-2, where NH—C(=X)—$(Y)_q$—$R_5$ is NHC(=S)O$R_5$. or NHC(=O)S$R_5$.

In another more specific embodiment, the invention provides compounds of formula ID-1 or ID-2, where NH—C(=X)—$(Y)_q$—$R_5$ is NHC(=O)$R_5$ or NHC(=O)O$R_5$.

In another more specific embodiment, the invention provides compounds of formula ID-1 or ID-2, where NH—C(=X)—$(Y)_q$—$R_5$ is NHC(=S)$R_5$ or NHC(=S)S$R_5$.

In another more specific embodiment, the invention provides compounds of formula ID-1 or ID-2, where NH—C(=X)—$(Y)_q$—$R_5$ is NHC(=S)O$R_5$. or NHC(=O)S$R_5$.

In a more specific embodiment, the invention provides compounds of formula IA,
where NH—C(=X)—$(Y)_q$—$R_5$ is NHC(=O)—$C_1$-$C_6$ alkyl, NHC(=O)—O$C_3$-$C_6$ alkyl, NHC(=O)—$(CH_2)_2C_5$-$C_6$ cycloalkyl, or NHC(=O)O—$(CH_2)_2C_5$-$C_6$ cycloalkyl.

In another embodiment, the invention provides compounds of formula I-N-A according to the structure below

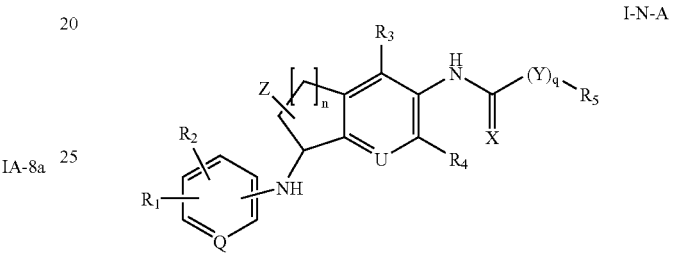

I-N-A

In another embodiment, the invention provides compounds of formula I-N-A, where U is N and Q is CH.

In a more specific embodiment, the invention provides compounds of formula I-N-A, where n is 1; X is O; U is N; and Q is CH.

In another embodiment, the invention provides compounds of formula I-N-A, where n is 1; X is O; U is N; and Q is N.

In another embodiment, the invention provides compounds of formula I-N-A, where n is 2; X is O; U is N; and Q is CH.

In another embodiment, the invention provides compounds of formula I-N-A, where n is 2; X is O; U is N; and Q is N.

In another embodiment, the invention provides compounds of formula I-N-A, where n is 3; X is O; U is N; and Q is CH.

In another embodiment, the invention provides compounds of formula I-N-A, where n is 3; X is O; U is N; and Q is N.

In another embodiment, the invention provides compounds of formula I-O-A, where U is N and Q is CH.

In another embodiment, the invention provides compounds of formula I-O-A, where n is 1; X is O; U is N; and Q is CH.

In another embodiment, the invention provides compounds of formula I-O-A, where n is 1; X is O; U is N; and Q is N.

In another embodiment, the invention provides compounds of formula I-O-A, where n is 2; X is O; U is N; and Q is CH.

In another embodiment, the invention provides compounds of formula I-O-A, where n is 2; X is O; U is N; and Q is N.

In another embodiment, the invention provides compounds of formula I-O-A, where n is 3; X is O; U is N; and Q is CH.

In another embodiment, the invention provides compounds of formula I-O-A, where n is 3; X is O; U is N; and Q is N.

In another embodiment, the invention provides compounds of formula I-S-A, where U is N and Q is CH.

In another embodiment, the invention provides compounds of formula I-S-A, where n is 1; X is O; U is N; and Q is CH.

In another embodiment, the invention provides compounds of formula I-S-A, where n is 1; X is O; U is N; and Q is N.

In another embodiment, the invention provides compounds of formula I-S-A, where n is 2; X is O; U is N; and Q is CH.

In another embodiment, the invention provides compounds of formula I-S-A, where n is 2; X is O; U is N; and Q is N.

In another embodiment, the invention provides compounds of formula I-S-A, where n is 3; U is N; and Q is CH.

In another embodiment, the invention provides compounds of formula I-S-A, where n is 3; X is O; U is N; and Q is CH.

In another embodiment, the invention provides compounds of formula I-Cgg-A, where U is N and Q is CH.

In another embodiment, the invention provides compounds of formula I-Cgg-A, where n is 1; X is O; U is N; and Q is CH.

In another embodiment, the invention provides compounds of formula I-Cgg-A, where n is 1; X is O; U is N; and Q is N.

In another embodiment, the invention provides compounds of formula I-Cgg-A, where n is 2; X is O; U is N; and Q is CH.

In another embodiment, the invention provides compounds of formula I-Cgg-A, where n is 2; X is O; U is N; and Q is N.

In another embodiment, the invention provides compounds of formula I-Cgg-A, where n is 3; X is O; U is N; and Q is CH.

In another embodiment, the invention provides compounds of formula I-Cgg-A, where n is 3; X is O; U is N; and Q is N.

In more specific embodiments, the invention provides compounds of formula I-N-A according to the structures below

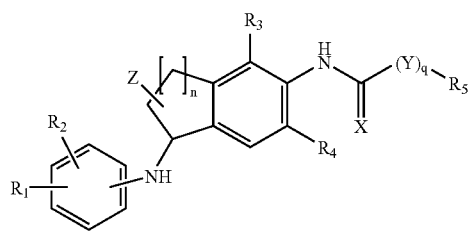

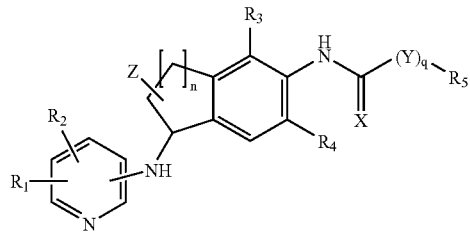

In additional more specific embodiments, the invention provides compounds of formula I-N-A according to the structures below

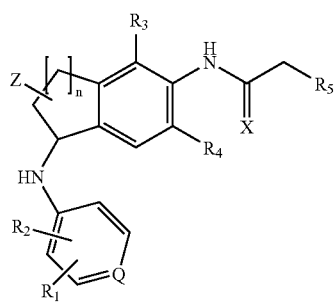

-continued

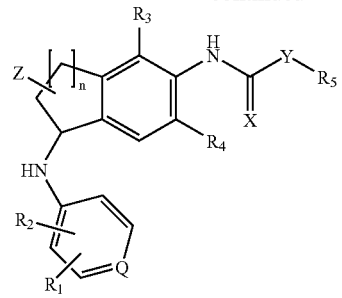

In even more specific embodiments, the invention provides compounds of formula I-N-A according to the structures below

I-N-A-1

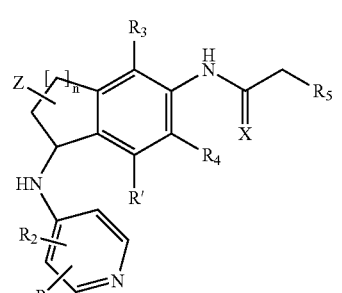

I-N-A-2

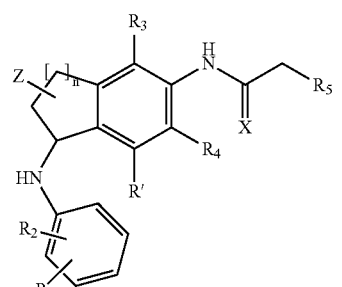

I-N-A-3

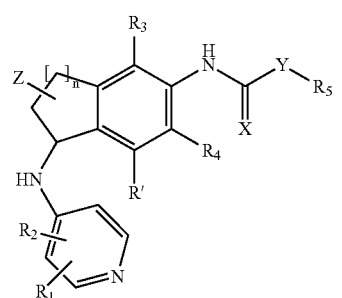

I-N-A-4

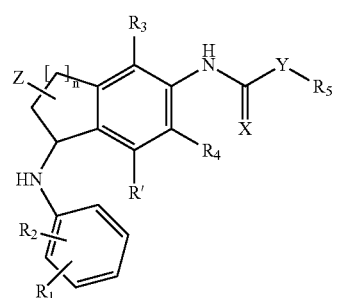

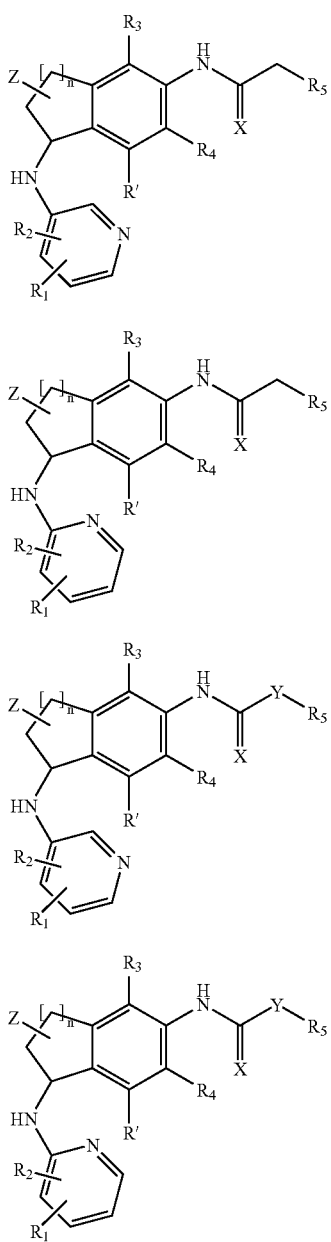

In still more specific embodiments, the invention provides compounds of formulas I-N-A-1, I-N-A-2, I-N-A-3, I-N-A-4, I-N-A-5, I-N-A-6, I-N-A-7, and I-N-A-8, where X is S.

In additional still more specific embodiments, the invention provides compounds of formulas I-N-A-1, I-N-A-2, I-N-A-3, I-N-A-4, I-N-A-5, I-N-A-6, I-N-A-7, and I-N-A-8, where X is O.

In still more specific embodiments, the invention provides compounds of formulas I-N-A-3, I-N-A-4, I-N-A-7, and I-N-A-8, in which X is S and Y is S.

In still more specific embodiments, the invention provides compounds of formulas I-N-A-3, I-N-A-4, I-N-A-7, and I-N-A-8, in which X is O and Y is S.

In still more specific embodiments, the invention provides compounds of formulas I-N-A-3, I-N-A-4, I-N-A-7, and I-N-A-8, in which X is S and Y is O.

In still more specific embodiments, the invention provides compounds of formulas I-N-A-3, I-N-A-4, I-N-A-7, and I-N-A-8, in which X is O and Y is O.

In even more specific embodiments, the invention provides compounds of formula I-N-A according to the structures below

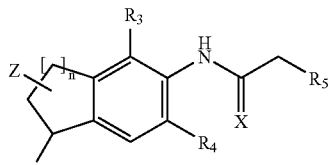

I-A-1a

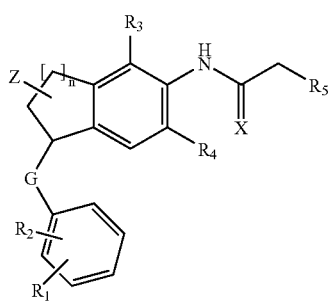

I-A-2a

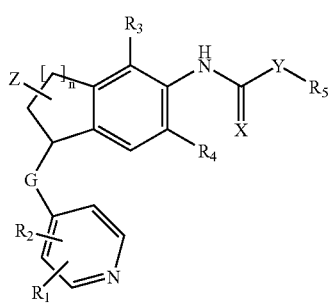

I-A-3a

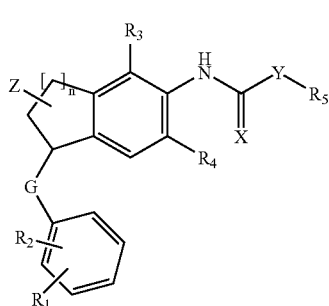

I-A-4a

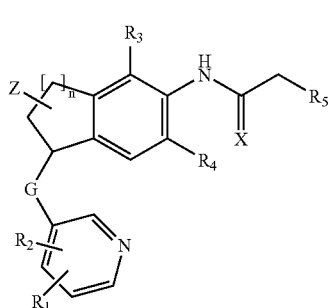

I-A-5a

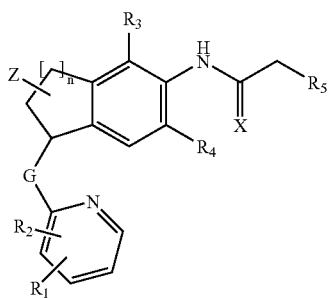

I-A-6a

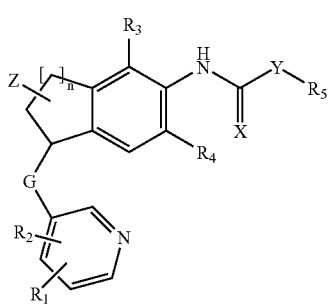

I-A-7a

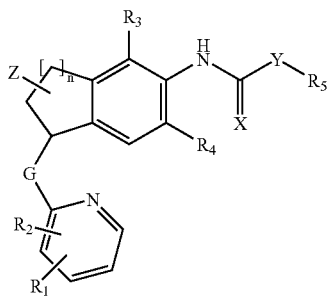

I-A-8a

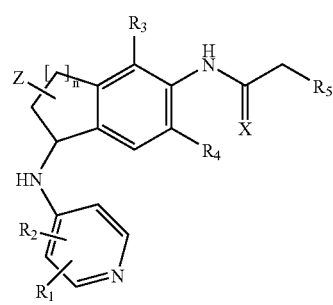

I-N-A-1a

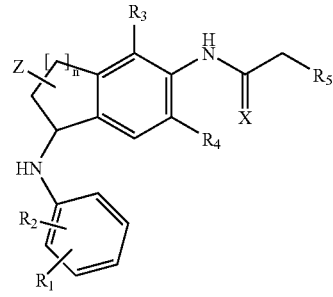

I-N-A-2a

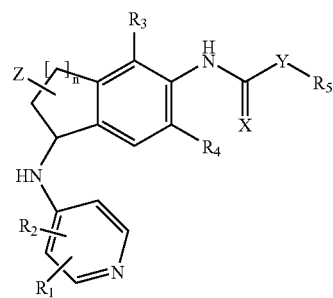

I-N-A-3a

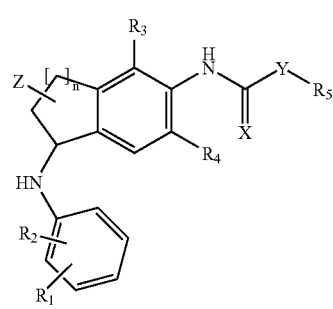

I-N-A-4a

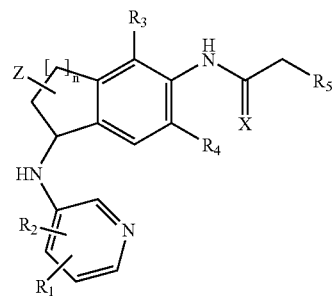

I-N-A-5a

In additional still more specific embodiments, the invention provides compounds of formulas I-A-1a, I-A-2a, I-A-3a, I-A-4a, I-A-5a, I-A-6a, I-A-7a, and I-A-8a, where G is O.

In additional still more specific embodiments, the invention provides compounds of formulas I-A-Ia, 1-A-2a, I-A-3a, I-A-4a, I-A-5a, I-A-6a, I-A-7a, and I-A-8a, where G is S.

In additional still more specific embodiments, the invention provides compounds of formulas I-A-Ia, 1-A-2a, I-A-3a, I-A-4a, I-A-5a, I-A-6a, I-A-7a, and I-A-8a, where G is $C(g_1)(g_2)$.

In additional still more specific embodiments, the invention provides compounds of formulas I-A-Ia, I-A-2a, I-A-3a, I-A-4a, I-A-5a, I-A-6a, I-A-7a, and I-A-8a, where G is CH2.

In additional still more specific embodiments, the invention provides compounds of formulas I-A-Ia, I-A-2a, I-A-3a, I-A-4a, I-A-5a, I-A-6a, I-A-7a, and I-A-8a, where G is $CH(CH_3)$.

In additional still more specific embodiments, the invention provides compounds of formulas I-A-Ia, I-A-2a, I-A-3a, I-A-4a, I-A-5a, I-A-6a, I-A-7a, and I-A-8a, where G is NH, according to the structures below -continued

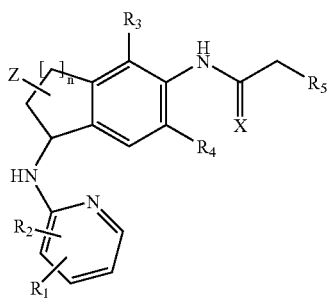
I-N-A-6a

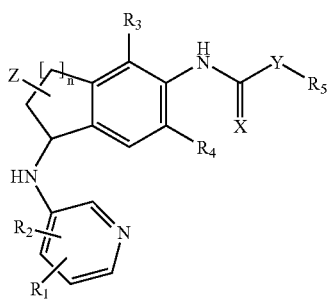
I-N-A-7a

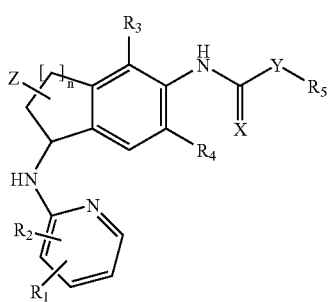
I-N-A-8a

In still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where X is S and Z is H, halogen, or unsubstituted or monosubstituted $C_1$-$C_6$ alkyl.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where X is O and Z is H, halogen, or unsubstituted or monosubstituted C1-C6 alkyl.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where n is 1; X is O; and Z is H.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where n is 2; X is O; and Z is H.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where n is 3; X is O; and Z is H.

In still more specific embodiments, the invention provides compounds of formulas I-N-A-3a, I-N-A-4a, I-N-A-7a, and I-N-A-8a, in which X is S; Y is S; and Z is H, halogen, or unsubstituted or mono substituted $C_1$-$C_6$ alkyl.

In still more specific embodiments, the invention provides compounds of formulas I-N-A-3a, I-N-A-4a, I-N-A-7a, and I-N-A-8a, in which X is O, Y is S, and Z is H, halogen, or unsubstituted or mono substituted C1-C6 alkyl.

In still more specific embodiments, the invention provides compounds of formulas I-N-A-3a, I-N-A-4a, I-N-A-7a, and I-N-A-8a, in which X is S, Y is O, and Z is H, halogen, or unsubstituted or mono substituted $C_1$-$C_6$ alkyl.

In still more specific embodiments, the invention provides compounds of formulas I-N-A-3a, I-N-A-4a, I-N-A-7a, and I-N-A-8a, in which X is O, Y is O, and Z is H, halogen, or unsubstituted or mono substituted C1-C6 alkyl.

In still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where Z is unsubstituted or monosubstituted $(CH_2)_n C_3$-$C_6$ cycloalkyl.

In still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where X is S; Z is H, halogen, or unsubstituted or monosubstituted $C_1$-$C_6$ alkyl; and $R_1$ is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where X is O; Z is H, halogen, or unsubstituted or monosubstituted $C_1$-$C_6$ alkyl; and $R_1$ is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In still more specific embodiments, the invention provides compounds of formulas I-N-A-3, I-N-A-4, I-N-A-7, and I-N-A-8, in which X is S; Y is S; Z is H, halogen, or unsubstituted or monosubstituted $C_1$-$C_6$ alkyl; and $R_1$ is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In still more specific embodiments, the invention provides compounds of formulas I-N-A-3, I-N-A-4, I-N-A-7, and I-N-A-8, in which X is O, Y is S, Z is H, halogen, or unsubstituted or monosubstituted $C_1$-$C_6$ alkyl; and $R_1$ is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In still more specific embodiments, the invention provides compounds of formulas I-N-A-3, I-N-A-4, I-N-A-7, and I-N-A-8, in which X is S, Y is O, Z is H, halogen, or unsubstituted or monosubstituted $C_1$-$C_6$ alkyl; and $R_1$ is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In still more specific embodiments, the invention provides compounds of formulas I-N-A-3, I-N-A-4, I-N-A-7, I-N-A-8, I-N-A-3a, I-N-A-4a, I-N-A-7a, and I-N-A-8a, in which X is O, Y is O, Z is H, halogen, or unsubstituted or monosubstituted $C_1$-$C_6$ alkyl; and Ili is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In still more specific embodiments, the invention provides compounds of formulas I-N-A-1, I-N-A-2, I-N-A-3, I-N-A-4, I-N-A-5, I-N-A-6, I-N-A-7, and I-N-A-8, where Z is unsubstituted or monosubstituted $C_3$-$C_6$ cycloalkyl; and $R_1$ is halogen, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O—$, $CH_3C(=O)$, $CH_3C(=O)NH—$, $CH_3NHC(=O)$, or $CH_3C(=NH)NH—$.

In additional still more specific embodiments, the invention provides compounds of formulas I-N-A-1, I-N-A-2, I-N-A-3, I-N-A-4, I-N-A-5, I-N-A-6, I-N-A-7, and I-N-A-8, where n is 1; X is O; R₁ is halogen, methyl, methoxy, trifluoromethyl, or trifluoromethoxy; and Z is H, halogen, methyl, or trifluoromethyl.

In additional still more specific embodiments, the invention provides compounds of formulas I-N-A-1, I-N-A-2, I-N-A-3, I-N-A-4, I-N-A-5, I-N-A-6, I-N-A-7, and I-N-A-8, where n is 2; X is O; R₁ is halogen, methyl, trifluoromethyl, methoxy, or trifluoromethoxy; and Z is H, halogen, methyl, or trifluoromethyl.

In additional still more specific embodiments, the invention provides compounds of formulas I-N-A-1, I-N-A-2, I-N-A-3, I-N-A-4, I-N-A-5, I-N-A-6, I-N-A-7, and I-N-A-8, where n is 3; X is O; R₁ is halogen, methyl, trifluoromethyl, methoxy, or trifluoromethoxy; and Z is H, halogen, methyl, or trifluoromethyl.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where n is 1; X is O; R₁ is halogen, methyl, trifluoromethyl, methoxy, or trifluoromethoxy; and Z is H, halogen, methyl, or trifluoromethyl.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where n is 2; X is O; R₁ is halogen, methyl, trifluoromethyl, methoxy, or trifluoromethoxy; and Z is H, halogen, methyl, or trifluoromethyl.

In additional still more specific embodiments, the invention provides compounds of formulas I-N-A-1a, I-N-A-2a, I-N-A-3a, I-N-A-4a, I-N-A-5a, I-N-A-6a, I-N-A-7a, and I-N-A-8a, where n is 3; X is O; R₁ is halogen, methyl, trifluoromethyl, methoxy, or trifluoromethoxy; and Z is H, halogen, methyl, or trifluoromethyl.

In additional embodiments, the invention provides compounds of formulas IE-1, IE-2, IE-3, and IE-4, according to the structures below

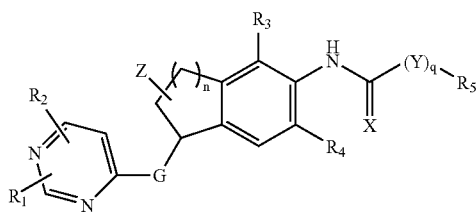

IE-1

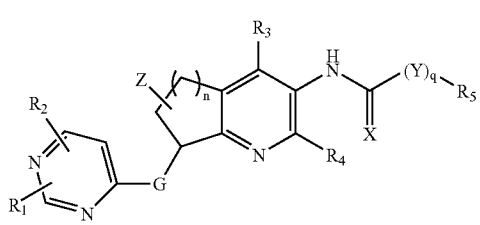

IE-2

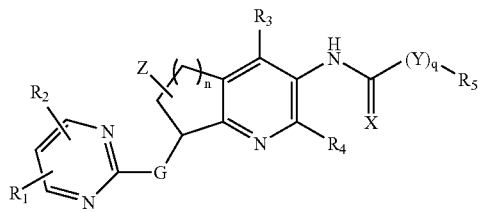

IE-3

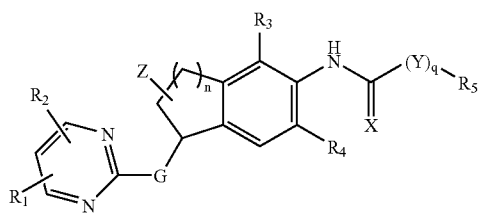

IE-4

In additional embodiments, the invention provides compounds of formulas I-N-E-1, I-N-E-2, I-N-E-3, and I-N-E-4, according to the structures below

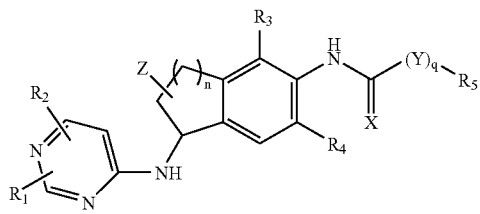

I-N-E-1

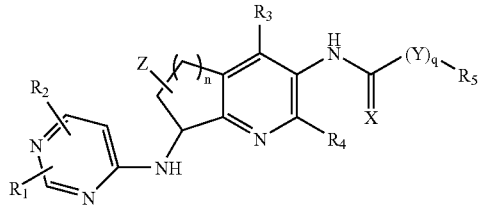

I-N-E-2

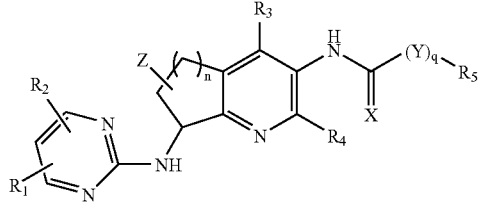

I-N-E-3

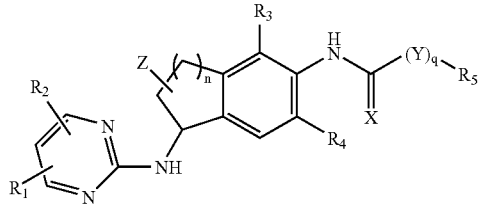

I-N-E-4

In additional more specific embodiments, the invention provides compounds of formula IE-1, IE-2, IE-3, and IE-4, where X is S; n is 1; q is 1 and Y is S; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is S; n is 2; q is 1 and Y is S; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is O; n is 1; q is 1 and Y is O; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is O; n is 2; q is 1 and Y is S; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is O; n is 3; q is 1 and Y is S; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is O; n is 1; q is zero; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is O; n is 2; q is zero; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In additional more specific embodiments, the invention provides compounds of formula IE-1, IE-2, IE-3, and IE-4, where X is O; n is 3; q is zero; Z is H, halogen, or $C_1$-$C_6$ alkyl; R3 is methyl, ethyl, trifluoromethyl, F, or Cl; and $R_4$ is H, methyl, ethyl, trifluoromethyl, F, or Cl.

In still more specific embodiments, the invention provides compounds of formulas IA-1, IA-2, IA-3, IA-4, IA-5, IA-6, IA-7, and IA-8, where n is 1; X is S; Z is H, halogen, or unsubstituted or mono substituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In additional still more specific embodiments, the invention provides compounds of formulas IA-1, IA-2, IA-3, IA-4, IA-5, IA-6, IA-7, and IA-8, where n is 1; X is O; Z is H, halogen, or unsubstituted or mono substituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In additional still more specific embodiments, the invention provides compounds of formulas IA-1a, IA-2a, IA-3a, IA-4a, IA-5a, IA-6a, IA-7a, and IA-8a, where n is 1; X is O; Z is H, halogen, or unsubstituted or monosubstituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In still more specific embodiments, the invention provides compounds of formulas IA-1, IA-2, IA-3, IA-4, IA-5, IA-6, IA-7, and IA-8, where n is 2; X is S; Z is H, halogen, or unsubstituted or mono substituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In additional still more specific embodiments, the invention provides compounds of formulas IA-1, IA-2, IA-3, IA-4, IA-5, IA-6, IA-7, and IA-8, where n is 2; X is O; Z is H, halogen, or unsubstituted or mono substituted $C_1$-$C_6$ alkyl; and $R_5$ is $C_3$-$C_6$ alkyl, $(CHR_6), C_3$-$C_6$ cycloalkyl, or $(CHR_6), CH_2C_3$-$C_6$ cycloalkyl.

In additional still more specific embodiments, the invention provides compounds of formulas IA-1a, IA-2a, IA-3a, IA-4a, IA-5a, IA-6a, IA-7a, and IA-8a, where n is 2; X is O; Z is H, halogen, or unsubstituted or monosubstituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In additional still more specific embodiments, the invention provides compounds of formulas IA-1, IA-2, IA-3, IA-4, IA-5, IA-6, IA-7, and IA-8, where n is 1; X is O; Z is H, halogen, or unsubstituted or mono substituted $C_1$-$C_4$ alkyl; $R_5$ is $C_3$-$C_6$ alkyl, $(CHR_6)C_3$-$C_6$ cycloalkyl, or $CH_2C_3$-$C_6$ cycloalkyl; and $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$.

In additional still more specific embodiments, the invention provides compounds of formulas IA-1a, IA-2a, IA-3a, IA-4a, IA-5a, IA-6a, IA-7a, and IA-8a, where n is 1; X is O; Z is H, halogen, or unsubstituted or mono substituted $C_1$-$C_4$ alkyl; $R_5$ is $C_3$-$C_6$ alkyl, $(CHR_6)C_3$-$C_6$ cycloalkyl, or $CH_2C_3$-$C_6$ cycloalkyl; and $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$.

In additional still more specific embodiments, the invention provides compounds of formulas IA-1, IA-2, IA-3, IA-4, IA-5, IA-6, IA-7, and IA-8, where n is 1; X is S; Z is H, halogen, or unsubstituted or mono substituted $C_1$-$C_4$ alkyl; $R_5$ is $C_3$-$C_6$ alkyl, $(CHR_6)C_3$-$C_6$ cycloalkyl, or $CH_2C_3$-$C_6$ cycloalkyl; and $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$.

In additional still more specific embodiments, the invention provides compounds of formulas IA-1, IA-2, IA-3, IA-4, IA-5, IA-6, IA-7, and IA-8, where n is 2; X is O; Z is H, halogen, or unsubstituted or mono substituted Cl-C4 alkyl; $R_5$ is $C_3$-$C_6$ alkyl, $(CHR_6)C_3$-$C_6$ cycloalkyl, or $CH_2C_3$-$C_6$ cycloalkyl; and $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$.

In additional still more specific embodiments, the invention provides compounds of formulas IA-1 a, IA-2a, IA-3a, IA-4a, IA-5a, IA-6a, IA-7a, and IA-8a, where n is 2; X is O; Z is H, halogen, or unsubstituted or mono substituted Cl-C4 alkyl; $R_5$ is $C_3$-$C_6$ alkyl, $(CHR_6)C_3$-$C_6$ cycloalkyl, or $CH_2C_3$-$C_6$ cycloalkyl; and $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$.

In additional still more specific embodiments, the invention provides compounds of formulas IA-1, IA-2, IA-3, IA-4, IA-5, IA-6, IA-7, and IA-8, where n is 2; X is S; Z is H, halogen, or unsubstituted or mono substituted $C_1$-$C_4$ alkyl; $R_5$ is $C_3$-$C_6$ alkyl, $(CHR_6)C_3$-$C_6$ cycloalkyl, or $CH_2C_3$-$C_6$ cycloalkyl; and $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$.

In additional still more specific embodiments, the invention provides compounds of formulas IA-1 a, IA-2a, IA-3a, IA-4a, IA-5a, IA-6a, IA-7a, and IA-8a, where X is O; q is zero; Z is H; n is 1; $R_5$ is $C_5$-$C_6$ alkyl or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C$ (=O), $CH_3C(=O)NH-$, $CH_3NHC(=O)$, $CH_3NHC(=NH)-$, or $CH_3C(=NH)NH-$; and R2 is H, methyl, or halogen.

In additional still more specific embodiments, the invention provides compounds of formulas IA-1a, IA-2a, IA-3a, IA-4a, IA-5a, IA-6a, IA-7a, and IA-8a, where X is O; q is zero; Z is H; n is 2; $R_5$ is $C_5$-$C_6$ alkyl or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and R2 is H, methyl, or halogen.

In additional still more specific embodiments, the invention provides compounds of formulas IA-1, IA-2, IA-3, IA-4, IA-5, IA-6, IA-7, and IA-8, where X is S; q is zero; n is 1; Z is H; $R_5$ is $C_3$-$C_6$ alkyl, $(CHR_6)C_3$-$C_6$ cycloalkyl, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H, methyl, or halogen.

In additional still more specific embodiments, the invention provides compounds of formulas IA-1, IA-2, IA-3, IA-4, IA-5, IA-6, IA-7, and IA-8, where X is S; q is zero; n is 2; Z is H; $R_5$ is $C_3$-$C_6$ alkyl, $(CHR_6)C_3$-$C_6$ cycloalkyl, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H, methyl, or halogen.

In additional still more specific embodiments, the invention provides compounds of formulas IA-1, IA-2, IA-3, IA-4, IA-5, IA-6, IA-7, IA-8, IA-1a, IA-2a, IA-3a, IA-4a, IA-5a, IA-6a, IA-7a, and IA-8a, where X is O; q is 1; Y is O; Z is H; n is 1; $R_5$ is $C_5$-$C_6$ alkyl, optionally monosubstituted, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IA-1, IA-2, IA-3, IA-4, IA-5, IA-6, IA-7, IA-8, IA-1a, IA-2a, IA-3a, IA-4a, IA-5a, IA-6a, IA-7a, and IA-8a, where X is O; q is 1; Y is O; Z is H; n is 2; $R_5$ is $C_5$-$C_6$ alkyl, optionally monosubstituted, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IA-1, IA-2, IA-3, IA-4, IA-5, IA-6, IA-7, and IA-8, where X is S; q is 1; Y is S; n is 1; Z is H; $R_5$ is $C_3$-$C_6$ alkyl, $(CHR_6)C_3$-$C_6$ cycloalkyl, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IA-1, IA-2, IA-3, IA-4, IA-5, IA-6, IA-7, and IA-8, where X is S; q is 1; Y is S; n is 2; Z is H; $R_5$ is $C_3$-$C_6$ alkyl, $(CHR_6)C_3$-$C_6$ cycloalkyl, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IA-1, IA-2, IA-3, IA-4, IA-5, IA-6, IA-7, and IA-8, where X is O; q is 1; Y is O; Z is H; n is 1; $R_5$ is tert-butyl or neopentyl; $R_1$ is F, Cl, Br, $CH_3$, $CH_2CH_3$, $OCH_3$, $OCH_2CH_3$, $CF_3$, $OCF_3$, or cyclopropyl; and $R_2$ is H or halogen.

In additional still more specific embodiments, the invention provides compounds of formulas IA-1, IA-2, IA-3, IA-4, IA-5, IA-6, IA-7, and IA-8, where X is O; q is 1; Y is O; Z is H; n is 2; $R_5$ is $C_5$-$C_6$ alkyl, optionally mono substituted, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3OC(-O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IA-1a, IA-2a, IA-3a, IA-4a, IA-5a, IA-6a, IA-7a, and IA-8a, where X is O; q is 1; Y is O; Z is H; n is 2; $R_5$ is $C_5$-$C_6$ alkyl, optionally monosubstituted, or $CH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, CH3C(=O), CH3C(=O)O-, CH30q=O), CH3C(=O)NH-, CH3NHC(=O), CH3NHC(=NH)-, or CH3C(=NH)NH-; and $R_2$ is H or halogen.

In additional still more specific embodiments, the invention provides compounds of formulas IB-1, IB-2, IC-1, IC-2, ID-1, ID-2, IE-1, IE-2, IE-3, and IE-4, where X is O; Z is H, halogen, or unsubstituted or mono substituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In additional still more specific embodiments, the invention provides compounds of formulas IB-1, IB-2, IC-1, IC-2, ID-1, ID-2, IE-1, IE-2, IE-3, and IE-4, where X is S; Z is H, halogen, or unsubstituted or mono substituted $C_1$-$C_6$ alkyl; and $R_5$ is $C_3$-$C_6$ alkyl, $(CHR_6)_wC_3$-$C_6$ cycloalkyl, or $(CHR_6)_wCH_2C_3$-$C_6$ cycloalkyl.

In additional still more specific embodiments, the invention provides compounds of formulas IB-1, IB-2, IC-1, IC-2, ID-1, ID-2, IE-1, IE-2, IE-3, and IE-4, where X is O; n is 1; Z is H, halogen, or unsubstituted or mono substituted $C_1$-$C_6$ alkyl; $R_5$ is $C_3$-$C_6$ alkyl, $(CHR_6)_wC_3$-$C_6$ cycloalkyl, or $(CHR_6)_wCH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IB-1, IB-2, IC-1, IC-2, ID-1, ID-2, IE-1, IE-2, IE-3, and IE-4, where X is O; n is 2; Z is H, halogen, or unsubstituted or mono substituted $C_1$-$C_6$ alkyl; $R_5$ is $C_3$-$C_6$ alkyl, $(CHR_6)_wC_3$-$C_6$ cycloalkyl, or $(CHR_6)_wCH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, $CH_3C(=O)O-$, $CH_3C(=O)$, $CH_3C(=O)NH-$, $CH_3NHC(=O)$, $CH_3NHC(=NH)-$, or $CH_3C(=NH)NH-$; and $R_2$ is H or halogen.

In additional still more specific embodiments, the invention provides compounds of formulas IB-1, IB-2, IC-1, IC-2, ID-1, ID-2, IE-1, IE-2, IE-3, and IE-4, where X is S; Z is H, halogen, or unsubstituted or mono substituted $C_1$-$C_6$ alkyl; $R_5$ is $C_3$-$C_6$ alkyl, $(CHR_6)_wC_3$-$C_6$ cycloalkyl, or $(CHR_6)_wCH_2C_3$-$C_6$ cycloalkyl; $R_1$ is F, Cl, Br, $CH_3$, $CH_2CH_3$, $OCH_3$, $OCH_2CH_3$, $CF_3$, $OCF_3$, cyclopropyl, vinyl, $CH_3C(=O)$, CH₃C(=O)O—, CH₃C(=O), CH₃C(=O)NH—, CH₃NHC(=O), CH₃NHC(=NH)—, or CH₃C(=NH)NH—; and R₂ is H or halogen.
In additional embodiments, the invention provides compounds as shown below. These are to be considered as specific examples of the compounds described above and should not be considered to limit the invention.
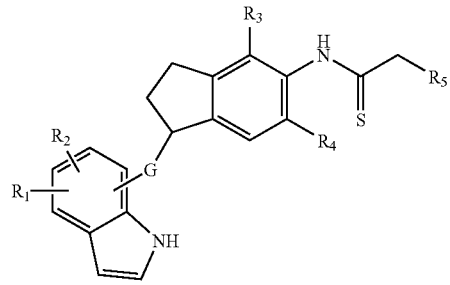
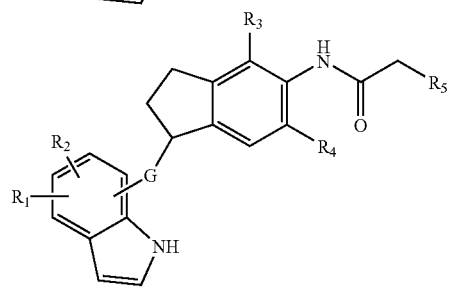
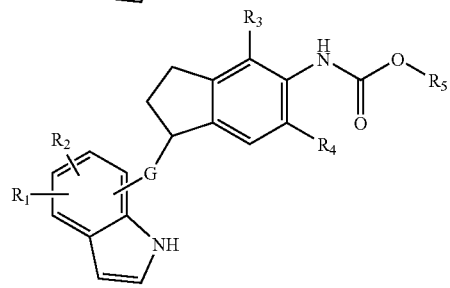
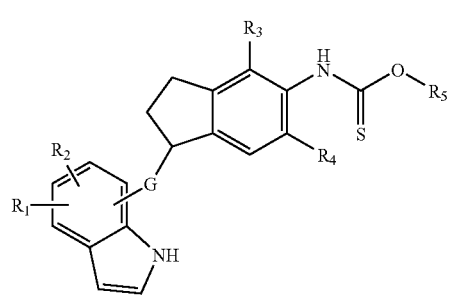
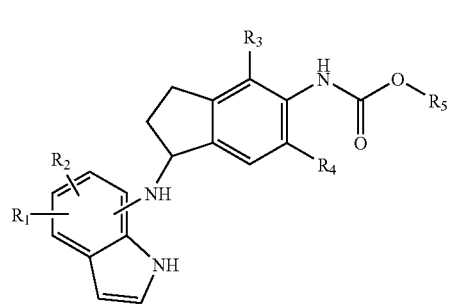
-continued
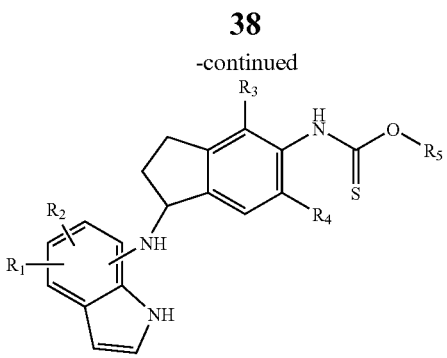
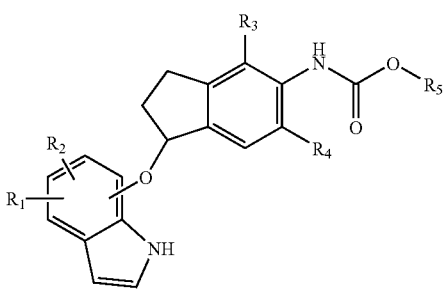
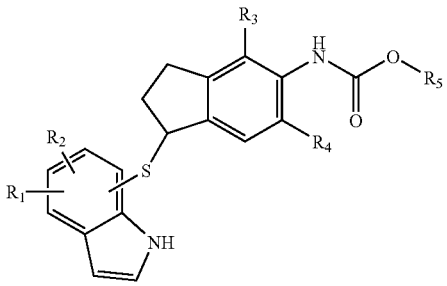
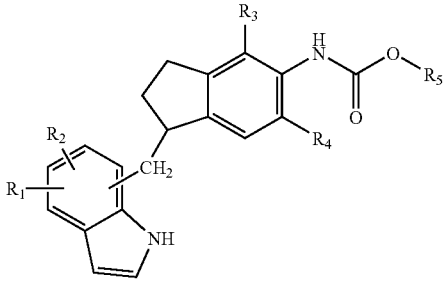
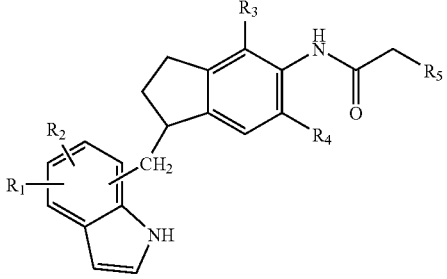
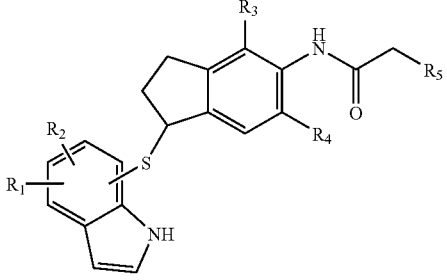

-continued
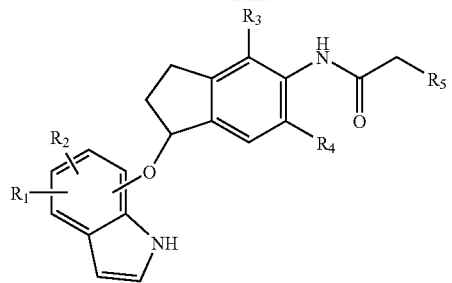
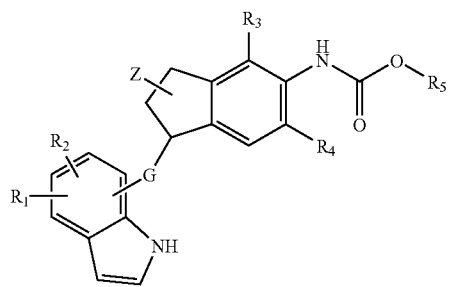
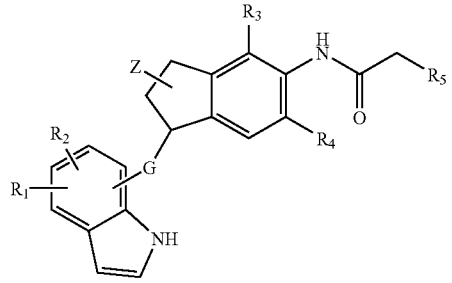
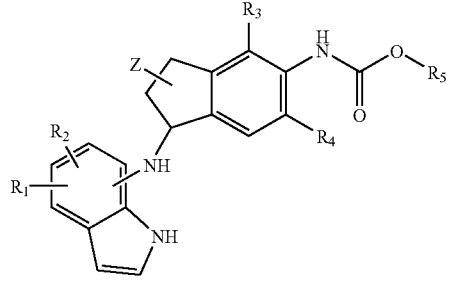
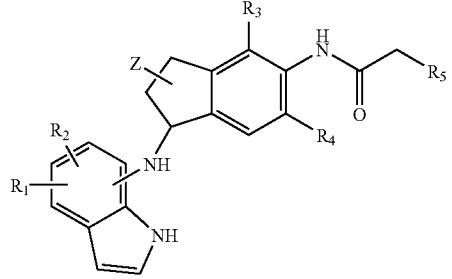
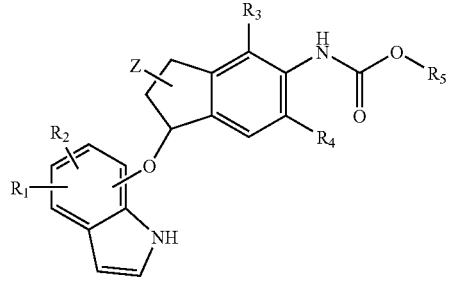
-continued
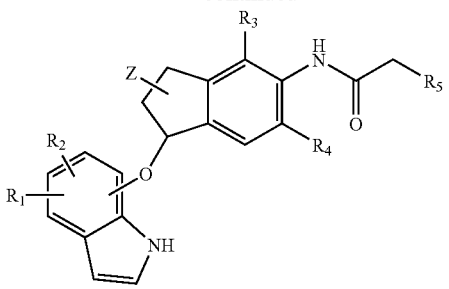
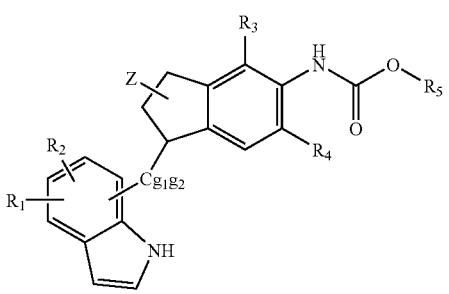
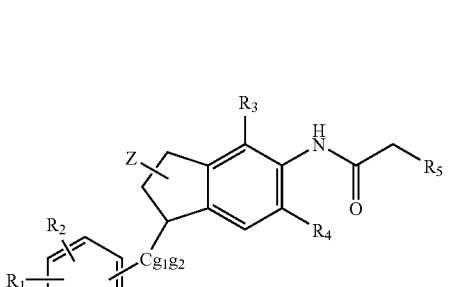
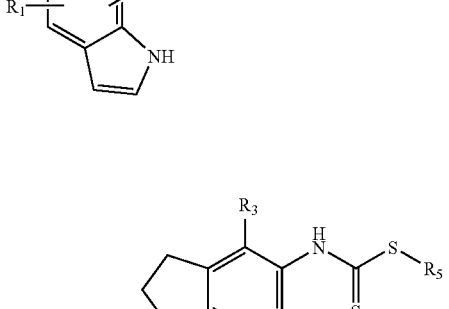
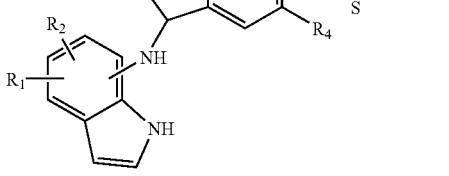
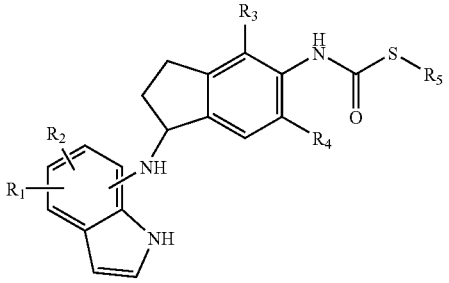

In additional embodiments, the invention provides compounds as shown below
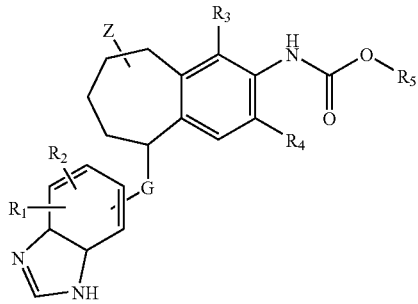
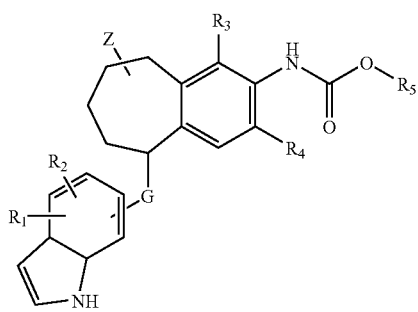
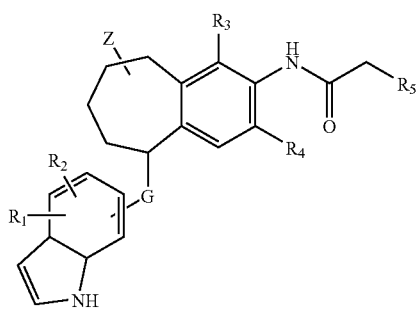
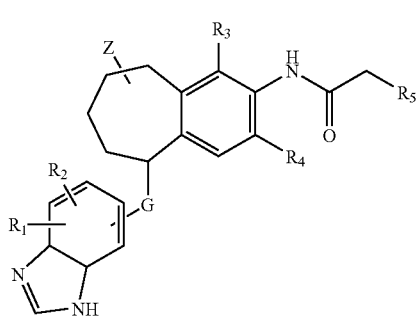
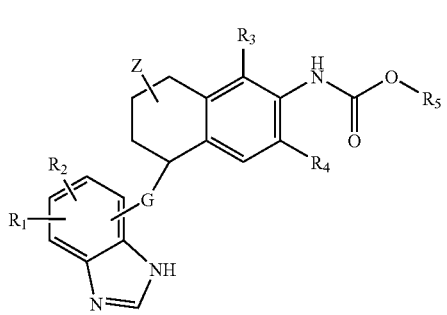
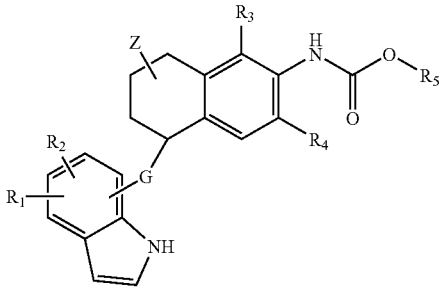
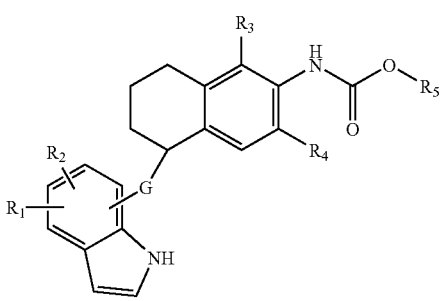
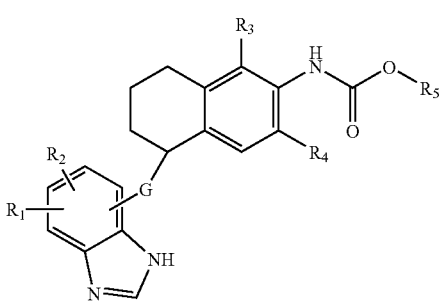
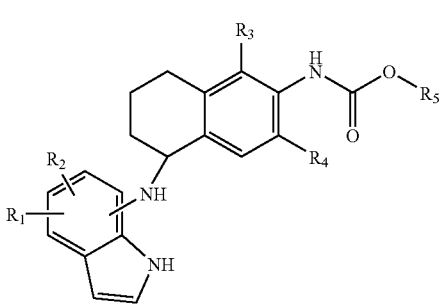
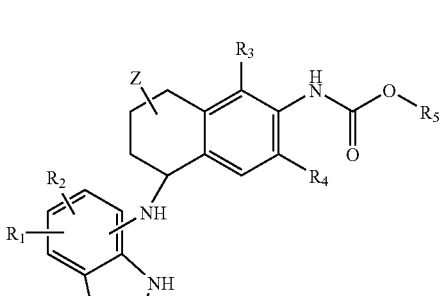

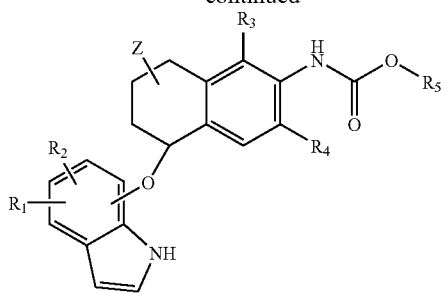
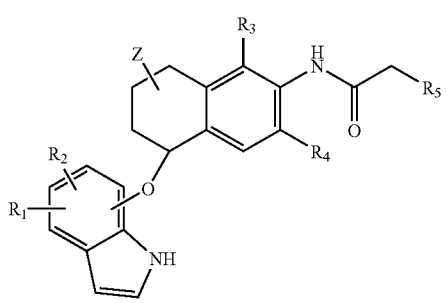
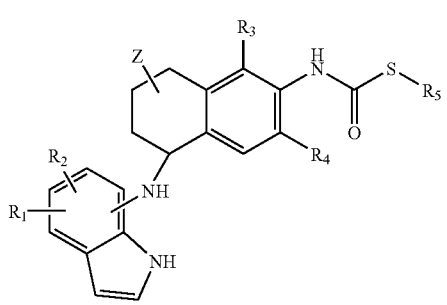
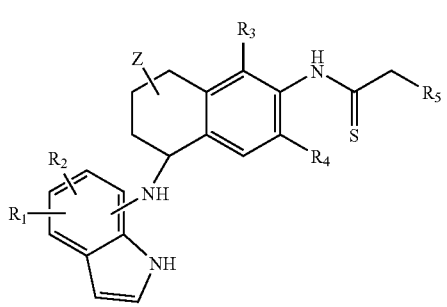
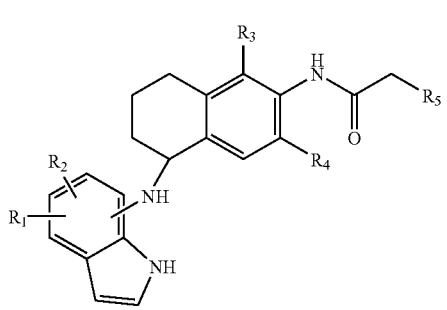
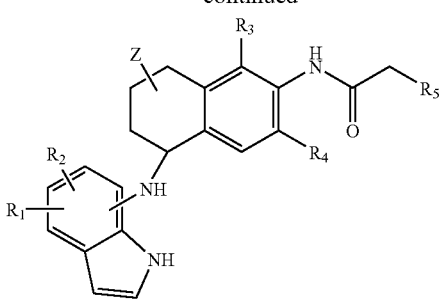
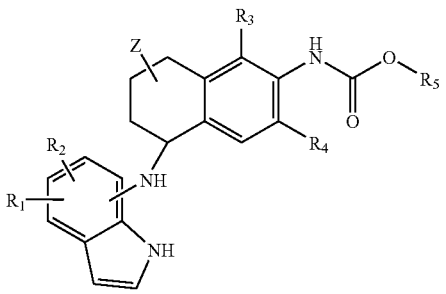
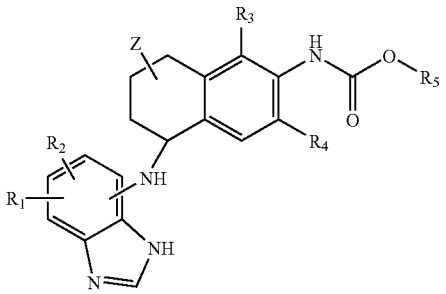
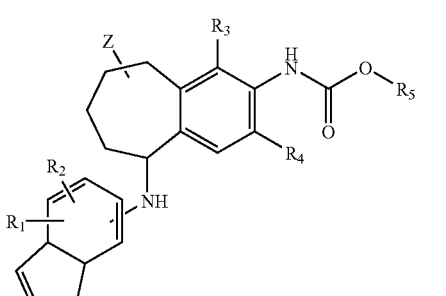
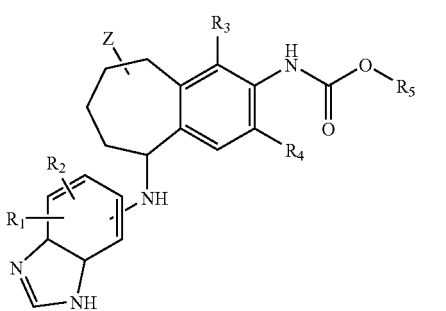

In other embodiments, the invention provides compounds as shown below

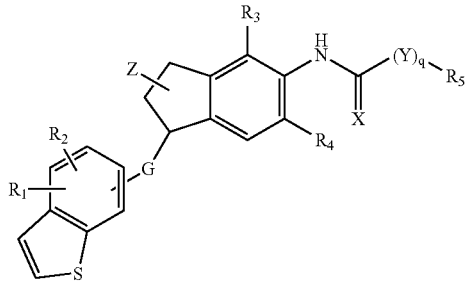

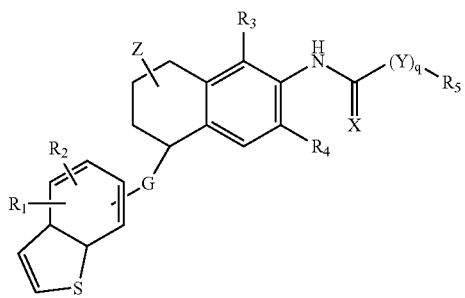

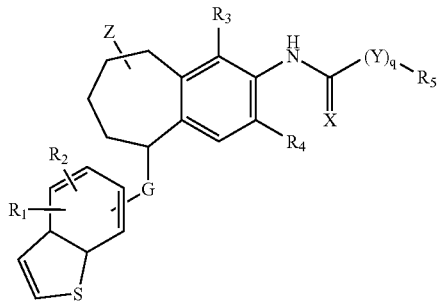

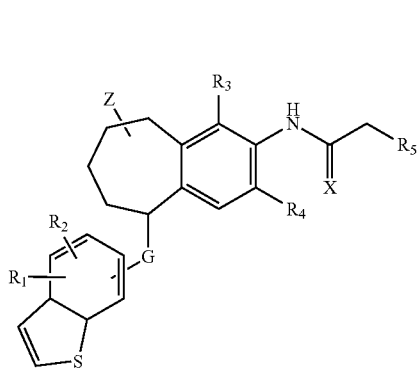

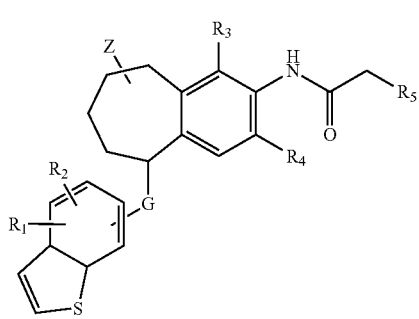

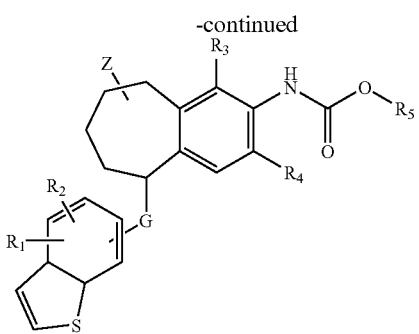

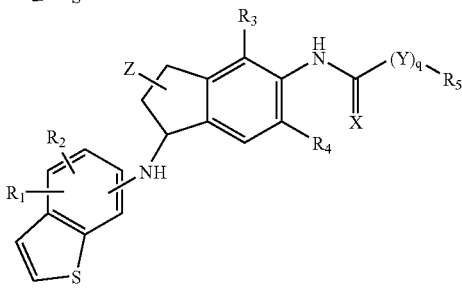

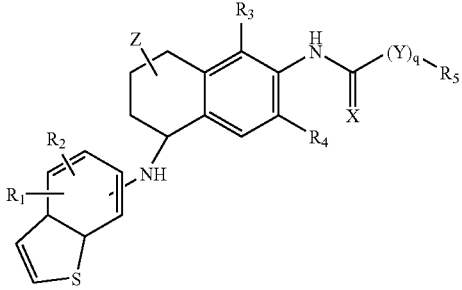

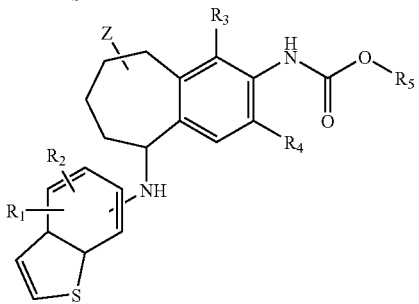

In additional still more specific embodiments, the invention provides compounds where $Ar_1$ is quinolyl, 2- or 3-thienyl, furanyl, benzothienyl, pyrrole, or indole.

In another more specific embodiment, this invention provides a compound of formula IA, formula IB, formula IC-1, or formula IC-2, where n is 1, $R_1$ is F, $CH_2F$, $CHF_2$, $CF_3$, or $CF_2CF_3$, q is 1, and X and Y are both O.

In another more specific embodiment, this invention provides a compound of formula IA, or formula IB, or formula IC-1 or IC-2, where n is 1, $R_1$ is $NHC_1$-$C_6$ alkyl or $NHC(=O)$ $C_1$-$C_6$ alkyl, q is 1, and X and Y are both O.

In a more specific embodiment, this invention provides a compound of formula IA, or formula IB, or formula IC-1 or IC-2, where n is 1, $R_1$ is $C(=O)$—NH—$C_1$-$C_6$ alkyl, $SO_2C_1$-$C_6$ alkyl, $SO_2NH$ $C_1$-$C_6$ alkyl, q is 1, and X and Y are both O.

In a more specific embodiment, this invention provides a compound of formula IA, or formula IB, or formula IC-1 or IC-2, where n is 1, $R_1$ is OH, OMe, OEt, SMe, or SEt, q is 1, and X and Y are both O.

In another more specific embodiment, this invention provides a compound of formula IA, or formula IB, or formula IC-1 or IC-2, where n is 1, $R_1$ is vinyl, allyl, methylethynyl, or phenylethynyl.

In another more specific embodiment, this invention provides a compound of formula IA, or formula IB, or formula IC-1 or IC-2, where n is 1, R1 is $C(=O)OC_1$-$C_6$ alkyl or $OC(=O)C_1$-$C_6$ alkyl, q is 1, and X and Y are both O.

In a still more specific embodiment, this invention provides a compound of formula I, where $Ar_1$ is phenyl or pyridyl, n is 1, $R_1$ is $C(=O)$—NH—$C_1$-$C_4$ alkyl, $SO_2C_1$-$C_4$ alkyl, $SO_2NHC_1$—C4 alkyl, q is 1, and X and Y are both O.

In a more specific embodiment, this invention provides a compound of formula I, where $Ar_1$ is phenyl or pyridyl, n is 1, $R_1$ is OH, OMe, OEt, SMe, or SEt, q is 1, and X and Y are both O.

In another more specific embodiment, this invention provides a compound of formula I, where $Ar_1$ is phenyl or pyridyl; n is 1; $R_1$ is vinyl, allyl, methylethynyl, or phenylethynyl; q is 1; and X and Y are both O.

In another more specific embodiment, this invention provides a compound of formula I, where $Ar_1$ is phenyl or pyridyl, n is 1, $R_1$ is $C(=O)OC_1$-$C_4$ alkyl or $OC(=O)C_1$-$C_4$ alkyl, q is 1, and X and Y are both O.

In another more specific embodiment, this invention provides a compound of formula I, where $Ar_1$ is phenyl or pyridyl, $R_1$ is $C_2$-$C_6$ alkenyl or $C_2$-$C_6$ alkynyl, n is 1, q is 1, and X and Y are both O.

In another more specific embodiment, this invention provides a compound of formula I, where $Ar_1$ is phenyl or pyridyl, $R_1$ is $C_1$-$C_4$ alkyl, n is 1, q is 1, and X and Y are both O.

In another more specific embodiment, this invention provides a compound of formula I, where $Ar_1$ is phenyl or pyridyl, $R_1$ is $SC_1$-$C_6$ alkyl, n is 1, q is 1, and X and Y are both O.

In another more specific embodiment, this invention provides a compound of formula IA, formula IB, formula IC-1, or formula IC-2, where n is 2, R1 is F, $CH_2F$, $CHF_2$, $CF_3$, or $CF_2CF_3$, q is 1, and X and Y are both O.

In another more specific embodiment, this invention provides a compound of formula IA, or formula IB, or formula IC-1 or IC-2, where n is 2, $R_1$ is $NHC_1$-$C_6$ alkyl or $NHC(=O)C_1$-$C_6$ alkyl, q is 1, and X and Y are both O.

In a more specific embodiment, this invention provides a compound of formula IA, or formula IB, or formula IC-1 or IC-2, where n is 2, $R_1$ is $C(=O)$—NH—$C_1$-$C_6$ alkyl, $SO_2C_1$-$C_6$ alkyl, $SO_2NHC_1$-$C_6$ alkyl, q is 1, and X and Y are both O.

In a more specific embodiment, this invention provides a compound of formula IA, or formula IB, or formula IC-1 or IC-2, where n is 2, $R_1$ is OH, OMe, OEt, SMe, or SEt, q is 1, and X and Y are both O.

In another more specific embodiment, this invention provides a compound of formula IA, or formula IB, or formula IC-1 or IC-2, where n is 2, R1 is vinyl, allyl, methylethynyl, or phenylethynyl.

In another more specific embodiment, this invention provides a compound of formula IA, or formula IB, or formula IC-1 or IC-2, where n is 2, $R_1$ is $C(=O)OC_1$-$C_6$ alkyl or $OC(=O)C_1$-$C_6$ alkyl, q is 1, and X and Y are both O.

In a still more specific embodiment, this invention provides a compound of formula I, where $Ar_1$ is phenyl or pyridyl, n is 2, ft] is $C(=O)$—NH—$C_1$-$C_4$ alkyl, $SO_2C_1$-$C_4$ alkyl, $SO_2NH C_1$-$C_4$ alkyl, q is 1, and X and Y are both O.

In a more specific embodiment, this invention provides a compound of formula I, where $Ar_1$ is phenyl or pyridyl, n is 2, $R_1$ is OH, OMe, OEt, SMe, or SEt, q is 1, and X and Y are both O.

In another more specific embodiment, this invention provides a compound of formula I, where $Ar_1$ is phenyl or pyridyl; n is 2; R1 is vinyl, allyl, methylethynyl, or phenylethynyl; q is 1, and X and Y are both O.

In another more specific embodiment, this invention provides a compound of formula I, where $Ar_1$ is phenyl or pyridyl, n is 2, $R_1$ is $C(=O)OC_1$-$C_4$ alkyl or $OC(=O)C_1$-$C_4$ alkyl, q is 1, and X and Y are both O.

In another more specific embodiment, this invention provides a compound of formula I, where $Ar_1$ is phenyl or pyridyl, $R_1$ is $C_2$-$C_6$ alkenyl or $C_2$-$C_6$ alkynyl, n is 2, q is 1, and X and Y are both O.

In another more specific embodiment, this invention provides a compound of formula I, where $Ar_1$ is phenyl or pyridyl, $R_1$ is Ci-C4 alkyl, n is 2, q is 1, and X and Y are both O.

In another more specific embodiment, this invention provides a compound of formula I, where $Ar_1$ is phenyl or pyridyl, $R_1$ is $SC_1$-$C_6$ alkyl, n is 2, q is 1, and X and Y are both O.

In another more specific embodiment, this invention provides a compound of formula IA, formula IB, formula IC-1, or formula IC-2, where n is 3, $R_1$ is F, $CH_2F$, $CHF_2$, $CF_3$, or $CF_2CF_3$, q is 1, and X and Y are both O.

In another more specific embodiment, this invention provides a compound of formula IA, or formula IB, or formula IC-1 or IC-2, where n is 3, $R_1$ is $NHC_1$-$C_6$ alkyl or $NHC(=O)C_1$-$C_6$ alkyl, q is 1, and X and Y are both O.

In a more specific embodiment, this invention provides a compound of formula IA, or formula IB, or formula IC-1 or IC-2, where n is 3, $R_1$ is $C(=O)$—NH—$C_1$-$C_6$ alkyl, $SO_2C_1$-$C_6$ alkyl, $SO_2NHC_1$-$C_6$ alkyl, q is 1, and X and Y are both O.

In a more specific embodiment, this invention provides a compound of formula IA, or formula IB, or formula IC-1 or IC-2, where n is 3, $R_1$ is OH, OMe, OEt, SMe, or SEt, q is 1, and X and Y are both O.

In another more specific embodiment, this invention provides a compound of formula IA, or formula IB, or formula IC-1 or IC-2, where n is 3, R1 is vinyl, allyl, methylethynyl, or phenylethynyl.

In another more specific embodiment, this invention provides a compound of formula IA, or formula IB, or formula IC-1 or IC-2, where n is 3, $R_1$ is $C(=O)OC_1$-$C_6$ alkyl or $OC(=O)C_1$-$C_6$ alkyl, q is 1, and X and Y are both O.

In a still more specific embodiment, this invention provides a compound of formula I, where $Ar_1$ is phenyl or pyridyl, n is 3, $R_1$ is $C(=O)$—NH—$C_1$-$C_4$ alkyl, $SO_2C_1$-$C_4$ alkyl, $SO_2NHCI$—C4 alkyl, q is 1, and X and Y are both O.

In a more specific embodiment, this invention provides a compound of formula I, where $Ar_1$ is phenyl or pyridyl, n is 3, $R_1$ is OH, OMe, OEt, SMe, or SEt, q is 1, and X and Y are both O.

In another more specific embodiment, this invention provides a compound of formula I, where $Ar_1$ is phenyl or pyridyl; n is 3; R1 is vinyl, allyl, methylethynyl, or phenylethynyl; q is 1; and X and Y are both O.

In another more specific embodiment, this invention provides a compound of formula I, where Art is phenyl or pyridyl, n is 3, $R_1$ is $C(=O)OC_1$-$C_4$ alkyl or $OC(=O)C_1$-$C_4$ alkyl, q is 1, and X and Y are both O.

In another more specific embodiment, this invention provides a compound of formula I, where $Ar_1$ is phenyl or pyridyl, R1 is $C_2$-$C_6$ alkenyl or $C_2$-$C_6$ alkynyl, n is 3, q is 1, and X and Y are both O.

In another more specific embodiment, this invention provides a compound of formula I, where $Ar_1$ is phenyl or pyridyl, R1 is $C_1$-$C_4$ alkyl, n is zero or 1, q is 1, and X and Y are both O.

In another more specific embodiment, this invention provides a compound of formula I, where $Ar_1$ is phenyl or pyridyl, R1 is $SC_1$-$C_6$ alkyl, n is zero or 1, q is 1, and X and Y are both O.

In another more specific embodiment, this invention provides a compound of formula I, where $Ar_1$ is monosubstituted phenyl, X is O, q is 1, and Y is S.

In another more specific embodiment, this invention provides a compound of formula I, where $Ar_1$ is monosubstituted phenyl, X is O, q is 1, and Y is O.

In another more specific embodiment, the invention provides a compound of formula I, where $Ar_1$ is monosubstituted phenyl, X is O, and q is zero.

In another more specific embodiment, this invention provides a compound of formula I, where $Ar_1$ is monosubstituted phenyl, X is S, q is 1, and Y is S.

In another more specific embodiment, this invention provides a compound of formula I, where $Ar_1$ is monosubstituted phenyl, X is S, q is 1, and Y is O.

In another more specific embodiment, the invention provides a compound of formula I, where $Ar_1$ is monosubstituted phenyl, X is S, and q is zero.

In a still more specific embodiment, this invention provides a compound of formula I, where $Ar_1$ is monosubstituted phenyl, $R_1$ is alkyl, monofluoroalkyl, difluoroalkyl, trifluoroalkyl, F, or Cl; $R_3$ and $R_4$ are, independently, H, methyl, ethyl, trifluoromethyl, F, or Cl; X is O; and q is zero.

In a still more specific embodiment, this invention provides a compound of formula I, where $Ar_1$ is monosubstituted phenyl, $R_1$ is alkyl, fluoroalkyl, or halo, $R_3$ and $R_4$ are H or methyl, X is O, q is 1, and Y is O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is $C_1$-$C_6$ alkyl, q is 1, and X and Y are both O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is CN, CH2CN, or halogen, q is 1, and X and Y are both O.

In a more specific embodiment, this invention provides a compound of formula I, where $Ar_1$ is phenyl or pyridyl, n is 1, $R_1$ is $CH_2F$, $CHF_2$, $CF_3$, or $CF_2CF_3$, q is 1, and X and Y are both O.

In a more specific embodiment, this invention provides a compound of formula I, where $Ar_1$ is phenyl or pyridyl, n is 1, $R_1$ is $OC_1$-$C_6$ alkyl or $C(=O)C_1$-$C_6$ alkyl, q is 1, and X and Y are both O.

In a more specific embodiment, this invention provides a compound of formula I, where $Ar_1$ is phenyl or pyridyl, n is 1, $R_1$ is $C(=O)OC_1$—C6 alkyl or $OC(=O)C_1$-$C_6$ alkyl, q is 1, and X and Y are both O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 1, q is 1, and X and Y are both O.

In a more specific embodiment, this invention provides a compound of formula I, where $Ar_1$ is phenyl or pyridyl, $R_1$ is $SC_1$-$C_6$ alkyl, n is 1, q is 1, and X and Y are both O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is $C_1$-$C_6$ alkyl, q is zero, and X is O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is CN, CH2CN, or halogen, q is zero, and X is O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is zero, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is 1, $R_1$ is $OC_1$-$C_6$ alkyl or $C(=O)C_1$-$C_6$ alkyl, q is 1, and X is O.

In a more specific embodiment, this invention provides a compound of formula I, where $Ar_1$ is phenyl or pyridyl, n is 1, R1 is $C(=O)OC_1$-$C_6$ alkyl or $OC(=O)C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 1, q is 1, and X is O.

In a more specific embodiment, this invention provides a compound of formula I, where $Ar_1$ is phenyl or pyridyl, $R_1$ is $SC_1$-$C_6$ alkyl, n is 1, q is 1, and X is O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is $C_1$-$C_6$ alkyl, q is 1, and X is O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is CN, CH2CN, or halogen, q is 1, and X is O.

In a more specific embodiment, this invention provides a compound of formula I, where $Ar_1$ is phenyl or pyridyl, $R_3$ and $R_4$ are, independently, H, methyl, ethyl, trifluoromethyl, F, or Cl, n is 1, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is 1, $R_1$ is $OC_1$-$C_6$ alkyl or $C(=O)C_1$-$C_6$ alkyl, q is 1, and X is O.

In a more specific embodiment, this invention provides a compound of formula I, where $Ar_1$ is phenyl or pyridyl, n is 1, $R_1$ is $C(=O)OC_1$-$C_6$ alkyl or $OC(=O)C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 1, q is 1, and X is O.

In a more specific embodiment, this invention provides a compound of formula I, where $Ar_1$ is phenyl or pyridyl, $R_1$ is $SC_1$-$C_6$ alkyl, n is 1, q is 1, and X is O.

In a more specific embodiment, this invention provides a compound of formula I, where $Ar_1$ is phenyl or pyridyl, $R_3$ and $R_4$ are independently H, methyl, ethyl, trifluoromethyl, F, or Cl, n is 2, $R_1$ is $C_1$-$C_6$ alkyl, q is 1, and X and Y are both O.

In a more specific embodiment, this invention provides a compound of formula I, where $Ar_1$ is phenyl or pyridyl, $R_3$ and $R_4$ are independently H, methyl, ethyl, trifluoromethyl, F, or Cl, n is 2, $R_1$ is CN, CH2CN, or halogen, q is 1, and X and Y are both O.

In a more specific embodiment, this invention provides a compound of formula I, where $Ar_1$ is phenyl or pyridyl, n is 2, R1 is $CH_2F$, $CHF_2$, $CF_3$, or $CF_2CF_3$, q is 1, and X and Y are both O.

In a more specific embodiment, this invention provides a compound of formula I, where $Ar_1$ is phenyl or pyridyl, n is 2, $R_1$ is $OC_1$-$C_6$ alkyl or C(=O)$C_1$-$C_6$ alkyl, q is 1, and X and Y are both O.

In a more specific embodiment, this invention provides a compound of formula I, where $Ar_1$ is phenyl or pyridyl, n is 2, $R_1$ is C(=O)$OC_1$-$C_6$ alkyl or OC(=O)$C_1$-$C_6$ alkyl, q is 1, and X and Y are both O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 2, q is 1, and X and Y are both O.

In a more specific embodiment, this invention provides a compound of formula I, where $Ar_1$ is phenyl or pyridyl, $R_1$ is $SC_1$-$C_6$ alkyl, n is 2, q is 1, and X and Y are both O.

In a more specific embodiment, this invention provides a compound of formula I, where $Ar_1$ is phenyl or pyridyl, $R_3$ and $R_4$ are independently H, methyl, ethyl, trifluoromethyl, F, or Cl, n is 2, R1 is $C_1$-$C_6$ alkyl, q is zero, and X is O.

In a more specific embodiment, this invention provides a compound of formula I, where $Ar_1$ is phenyl or pyridyl, $R_3$ and $R_4$ are independently H, methyl, ethyl, trifluoromethyl, F, or Cl, n is 2, $R_1$ is CN, CH2CN, or halogen, q is zero, and X is O.

In a more specific embodiment, this invention provides a compound of formula I, where $Ar_1$ is phenyl or pyridyl, $R_3$ and $R_4$ are independently H, methyl, ethyl, trifluoromethyl, F, or Cl, n is 2, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is 2, $R_1$ is $OC_1$-$C_6$ alkyl or C(=O)$C_1$-$C_6$ alkyl, q is 1, and X is O.

In a more specific embodiment, this invention provides a compound of formula I, where $Ar_1$ is phenyl or pyridyl, n is 2, $R_1$ is C(=O)$OC_1$-$C_6$ alkyl or OC(=O)$C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 2, q is 1, and X is O.

In a more specific embodiment, this invention provides a compound of formula I, where $Ar_1$ is phenyl or pyridyl, $R_1$ is $SC_1$-$C_6$ alkyl, n is 2, q is 1, and X is O.

In a more specific embodiment, this invention provides a compound of formula I, where $Ar_1$ is phenyl or pyridyl, $R_3$ and $R_4$ are H or methyl, n is 2, $R_1$ is $C_1$-$C_6$ alkyl, q is 1, and X is O.

In a more specific embodiment, this invention provides a compound of formula I, where $Ar_1$ is phenyl or pyridyl, $R_3$ and $R_4$ are H or methyl, n is 2, $R_1$ is CN, CH2CN, or halogen, q is 1, and X is O.

In a more specific embodiment, this invention provides a compound of formula I, where An is phenyl or pyridyl, $R_3$ and $R_4$ are H or methyl, n is 2, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is 2, $R_1$ is $OC_1$-$C_6$ alkyl or C(=O)$C_1$-$C_6$ alkyl, q is 1, and X is O.

In a more specific embodiment, this invention provides a compound of formula I, where $Ar_1$ is phenyl or pyridyl, n is 2, R1 is C(=O)$OC_1$-$C_6$ alkyl or OC(=O)$C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 2, q is 1, and X is O.

In a more specific embodiment, this invention provides a compound of formula I, where $Ar_1$ is phenyl or pyridyl, $R_1$ is $SC_1$-$C_6$ alkyl, n is 2, q is 1, and X is O.

In a more specific embodiment, this invention provides a compound of formula I, where $Ar_1$ is phenyl or pyridyl, $R_3$ and $R_4$ are H or methyl, n is 3, $R_1$ is $C_1$-$C_6$ alkyl, q is 1, and X and Y are both O.

In a more specific embodiment, this invention provides a compound of formula I, where $Ar_1$ is phenyl or pyridyl, $R_3$ and $R_4$ are H or methyl, n is 3, $R_1$ is CN, CH2CN, or halogen, q is 1, and X and Y are both O.

In a more specific embodiment, this invention provides a compound of formula I, where $Ar_1$ is phenyl or pyridyl, n is 3, $R_1$ is $CH_2F$, $CHF_2$, $CF_3$, or $CF_2CF_3$, q is 1, and X and Y are both O.

In a more specific embodiment, this invention provides a compound of formula I, where $Ar_1$ is phenyl or pyridyl, n is 3, $R_1$ is $OC_1$-$C_6$ alkyl or C(=O)$C_1$-$C_6$ alkyl, q is 1, and X and Y are both O.

In a more specific embodiment, this invention provides a compound of formula I, where Art is phenyl or pyridyl, n is 3, $R_1$ is C(=O)$OC_1$-$C_6$ alkyl or OC(=O)$C_1$-$C_6$ alkyl, q is 1, and X and Y are both O.

In a more specific embodiment, this invention provides a compound of formula I, where An is phenyl or pyridyl, $R_1$ is $C_2$-$C_6$ alkenyl or $C_2$-$C_6$ alkynyl, n is 3, q is 1, and X and Y are both O.

In a more specific embodiment, this invention provides a compound of formula I, where $Ar_1$ is phenyl or pyridyl, $R_1$ is $SC_1$-$C_6$ alkyl, n is 3, q is 1, and X and Y are both O.

In a more specific embodiment, this invention provides a compound of formula I, where $Ar_1$ is phenyl or pyridyl, $R_3$ and $R_4$ are H or methyl, n is 3, $R_1$ is $C_1$-$C_6$ alkyl, q is zero, and X is O.

In a more specific embodiment, this invention provides a compound of formula I, where $Ar_1$ is phenyl or pyridyl, $R_3$ and $R_4$ are H or methyl, n is 3, $R_1$ is CN, CH2CN, or halogen, q is zero, and X is O.

In a more specific embodiment, this invention provides a compound of formula I, where $Ar_1$ is phenyl or pyridyl, $R_3$ and $R_4$ are H or methyl, n is 3, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is 3, $R_1$ is $OC_1$-$C_6$ alkyl or C(=O)$C_1$-$C_6$ alkyl, q is 1, and X is O.

In a more specific embodiment, this invention provides a compound of formula I, where $Ar_1$ is phenyl or pyridyl, n is 3, $R_1$ is C(=O)$OC_1$-$C_6$ alkyl or OC(=O)$C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 3, q is 1, and X is O.

In a more specific embodiment, this invention provides a compound of formula I, where $Ar_1$ is phenyl or pyridyl, $R_1$ is $SC_1$-$C_6$ alkyl, n is 3, q is 1, and X is O.

In a more specific embodiment, this invention provides a compound of formula I, where $Ar_1$ is phenyl or pyridyl, $R_3$ and $R_4$ are H or methyl, n is 3, $R_1$ is $C_1$-$C_6$ alkyl, q is 1, and X is O.

In a more specific embodiment, this invention provides a compound of formula I, where $Ar_1$ is phenyl or pyridyl, $R_3$ and $R_4$ are H or methyl, n is 3, $R_1$ is CN, CH2CN, or halogen, q is 1, and X is O.

In a more specific embodiment, this invention provides a compound of formula I, where $Ar_1$ is phenyl or pyridyl, $R_3$ and $R_4$ are H or methyl, n is 1, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is 3, $R_1$ is $OC_1$-$C_6$ alkyl or $C(=O)C_1$-$C_6$ alkyl, q is 1, and X is O.

In a more specific embodiment, this invention provides a compound of formula I, where $Ar_1$ is phenyl or pyridyl, n is 3, $R_1$ is $C(=O)OC_1$-$C_6$ alkyl or $OC(=O)C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is 3, q is 1, and X is O.

In a more specific embodiment, this invention provides a compound of formula I, where $Ar_1$ is phenyl or pyridyl, $R_1$ is $SC_1$-$C_6$ alkyl, n is 3, q is 1, and X is O.

In another embodiment, this invention provides a compound of formula I, in which $R_5$ is $C_1$-$C_6$ alkyl.

In another embodiment, this invention provides a compound of formula I, in which $R_5$ is $(CHR_6)_w C_3$-$C_6$ cycloalkyl, where w is 1 or 2 and $R_6$ is H or methyl.

In another embodiment, this invention provides a compound of formula I, in which $R_5$ is $(CHR_6)_w CH_2 C_3$-$C_6$ cycloalkyl, where w is 1 or 2 and $R_6$ is H or methyl.

In another embodiment, this invention provides a compound of formula I, in which $R_5$ is $CH_2(CHR_6)_w C_3$-$C_6$ cycloalkyl, where w is 1 or 2 and $R_6$ is H or methyl.

In another embodiment, this invention provides a compound of formula I, in which R5 is $(CHR_6)_w C_5$-$C_6$ oxacycloalkyl, where w is 1 or 2 and $R_6$ is H or methyl.

In another embodiment, this invention provides a compound of formula I, in which R5 is $(CHR_6)_w C_5$-$C_6$ azacycloalkyl, where w is 1 or 2 and $R_6$ is H or methyl.

In another embodiment, this invention provides a compound of formula I, in which R5 is $(CHR_6)_w C_5$-$C_6$ thiocycloalkyl, where w is 1 or 2 and $R_6$ is H or methyl.

In another embodiment, this invention provides a compound of formula I, in which R5 is $(CHR_6)_w CH_2 C_5$-$C_6$ azacycloalkyl, where w is 1 or 2 and $R_6$ is H or methyl.

In another embodiment, this invention provides a compound of formula I, in which R5 is $(CHR_6)_w CH_2 C_5$-$C_6$ azacycloalkyl, where w is 1 or 2 and $R_6$ is H or methyl.

In a more specific embodiment, this invention provides a compound of formula I, in which $R_5$ is $(CHR_6)_w Z$, where w is 1 or 2, $R_6$ is H or methyl, and Z is piperidinyl.

In another more specific embodiment, this invention provides a compound of formula I, in which $R_5$ is $(CHR_6)_w Z$, where w is 1 or 2, $R_6$ is H or methyl, and Z is 1-pyrrolidinyl or 1-piperidinyl.

In another more specific embodiment, this invention provides a compound of formula I, in which $R_5$ is $(CHR_6)_w Z$, where w is 1 or 2, $R_6$ is H or methyl, and Z is 2-pyrrolidinyl or 3-pyrrolidinyl.

In another embodiment, this invention provides a compound of formula I, in which $R_5$ is $(CHR_6)_w Z$, where w is 1 or 2, $R_6$ is H or methyl, and Z is morpholyl, thiazolidinyl, oxazolidinyl, isothiazolidinyl, or isoxazolidinyl.

In another embodiment, this invention provides a compound of formula I, in which R5 is $(CHR_6)_w CH_2 C_3$-$C_6$ cycloalkyl, where w is 1 or 2 and $R_6$ is H or methyl.

In another embodiment, this invention provides a compound of formula I, in which $R_5$ is $(CH_2)_w (CHR_6)_w C_3$-$C_6$ cycloalkyl, where w is 1 or 2 and $R_6$ is H or methyl.

In another embodiment, this invention provides a compound of formula I, in which R5 is $(CHR_6)_w C_3$-$C_6$ cycloalkyl, where w is 1 or 2 and $R_6$ is H or methyl.

In a more specific embodiment, this invention provides a compound of formula IA, in which $R_5$ is $(CH_2)_w$—$C_5$-$C_6$ cycloalkyl.

In another embodiment, this invention provides a compound of formula I, in which $R_5$ is $CH=CH$—$C_3$-$C_6$ cycloalkyl, where the carbon-carbon double bond has the E configuration.

In another embodiment, this invention provides a compound of formula I, in which $R_5$ is $CH=CH$—$C_3$-$C_6$ cycloalkyl, where the carbon-carbon double bond has the Z configuration.

In another embodiment, this invention provides a compound of formula I, in which $R_5$ is $CH_2$—$CH=CH$—$C_3$-$C_6$ cycloalkyl, where the carbon-carbon double bond has the E configuration.

In another embodiment, this invention provides a compound of formula I, in which $R_5$ is $CH_2 CH=CH$—$C_3$-$C_6$ cycloalkyl, where the carbon-carbon double bond has the Z configuration.

In another embodiment, this invention provides a compound of formula I, in which R5 is $CH=CH$—$CH_2$—$C_3$-$C_6$ cycloalkyl, where the carbon-carbon double bond has the E configuration.

In another embodiment, this invention provides a compound of formula I, in which $R_5$ is $CH=CH$—$CH_2$—$C_3$-$C_6$ cycloalkyl, where the carbon-carbon double bond has the Z configuration.

In another, more specific embodiment, this invention provides a compound of formula I, in which $R_5$ is $(CHR_6)_w C_3$-$C_6$ cycloalkyl, where the cycloalkyl group is mono substituted.

In another embodiment, this invention provides a compound of formula I, in which $R_5$ is $CH=CH$—$CH_2$—$C_3$-$C_6$ cycloalkyl or $CH=CH$—$C_3$-$C_6$ cycloalkyl, where the cycloalkyl group is monosubstituted.

In another embodiment, this invention provides a compound of formula IA, in which $R_3$ and $R_4$ are H or methyl, n is 1, q is 1, X is O and $R_5$ is $C_5$-$C_6$ alkyl.

In another aspect according to the invention, there is provided a compound selected from the group consisting of:

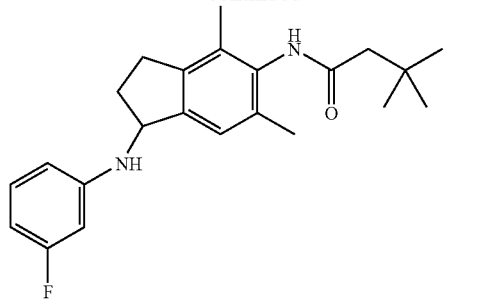
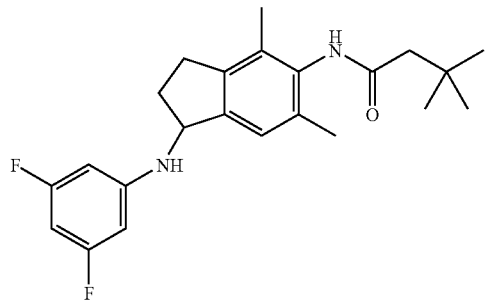
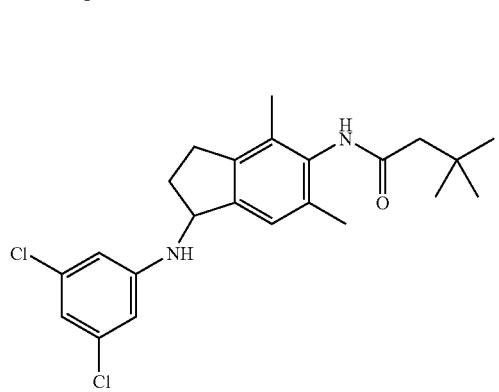
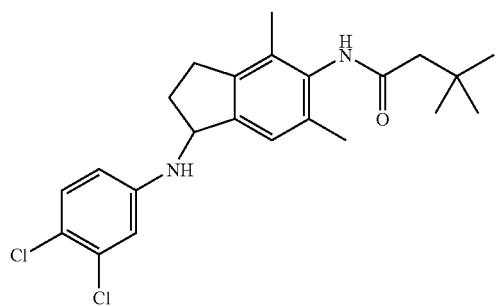
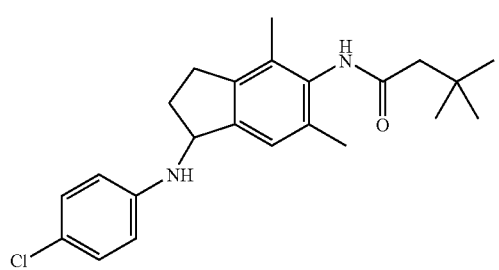
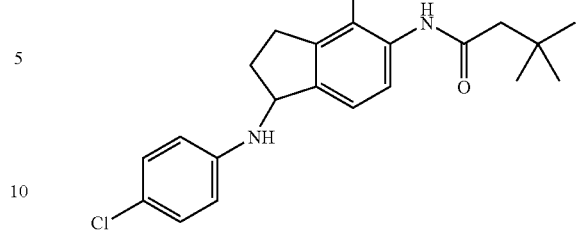
or a pharmaceutically acceptable salt or solvate thereof.
In still another aspect according to the invention, there is provided a compound selected from the group consisting of:
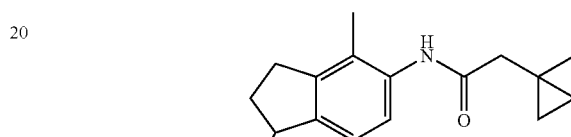
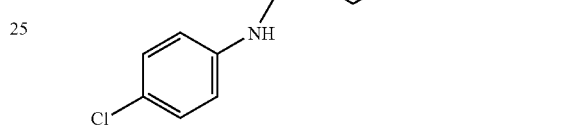
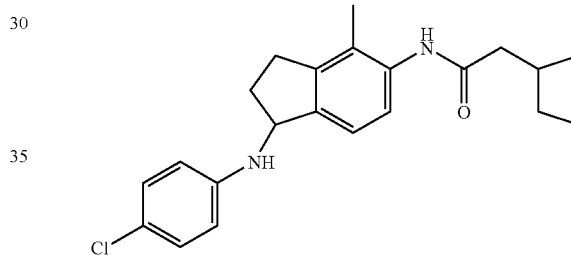
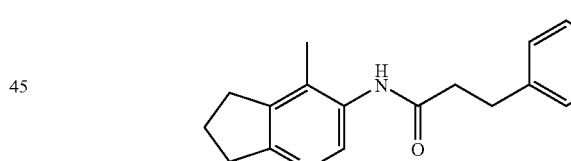
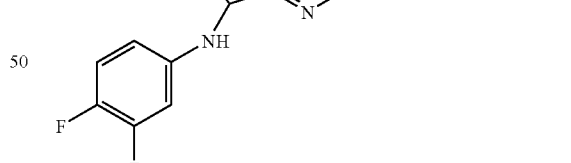
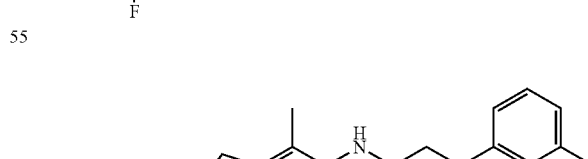
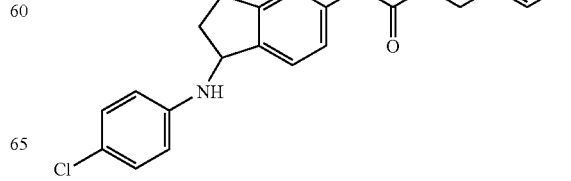

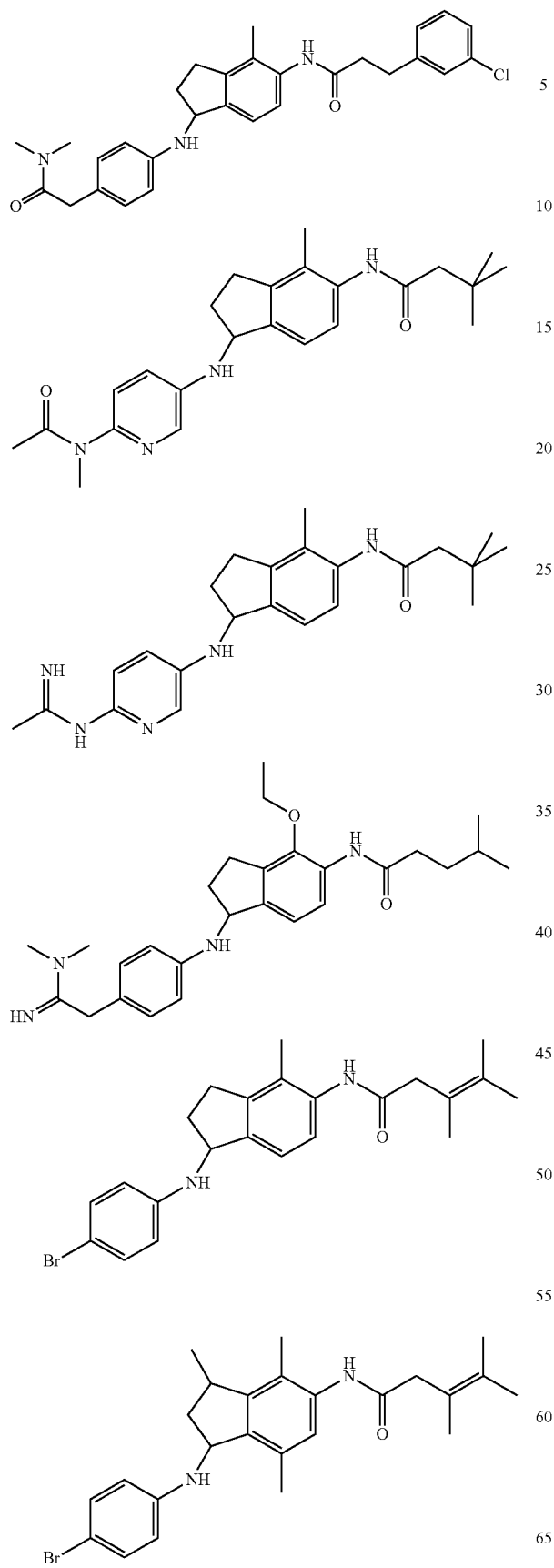
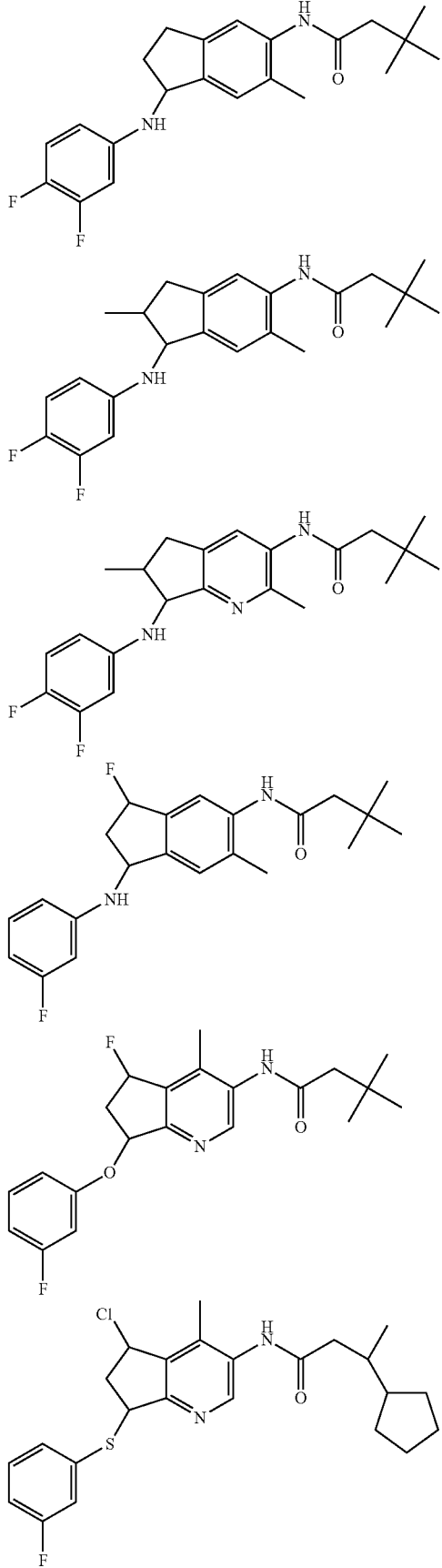

-continued
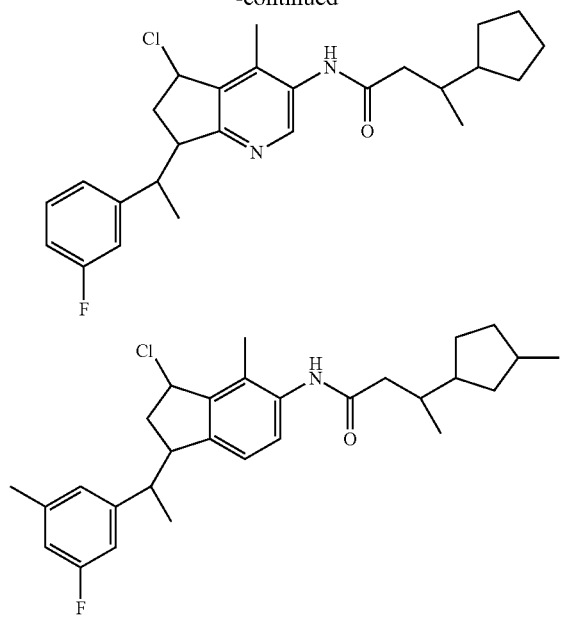
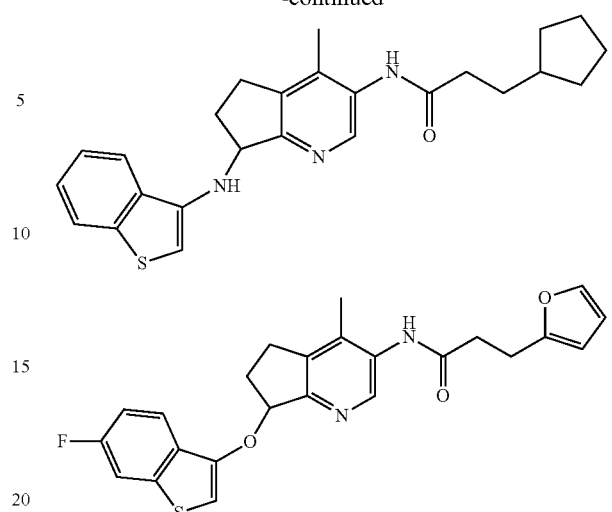
or a pharmaceutically acceptable salt or solvate thereof.
In still another aspect according to the invention, there is provided a compound selected from the group consisting of:
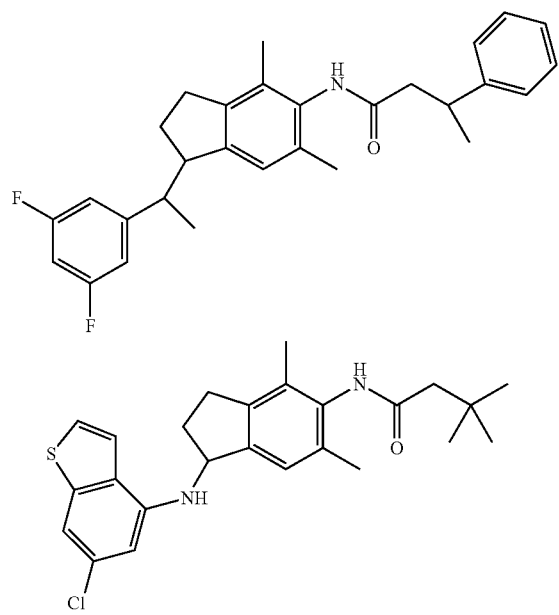
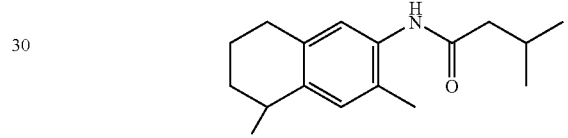
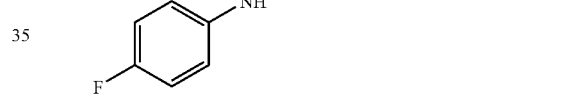
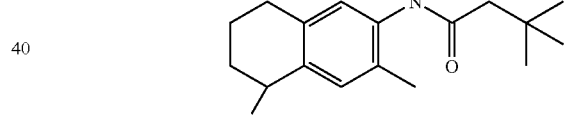
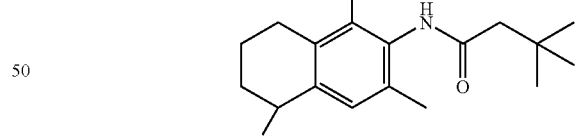
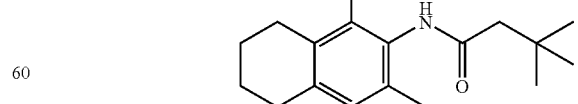
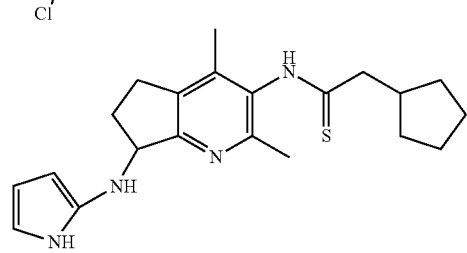

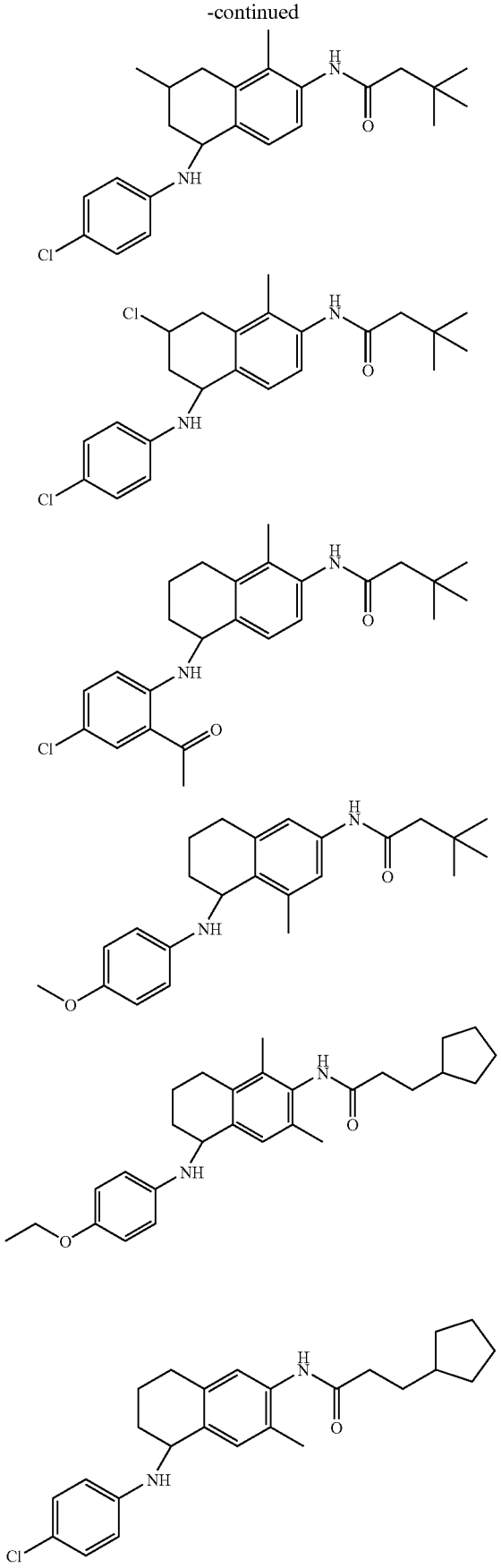
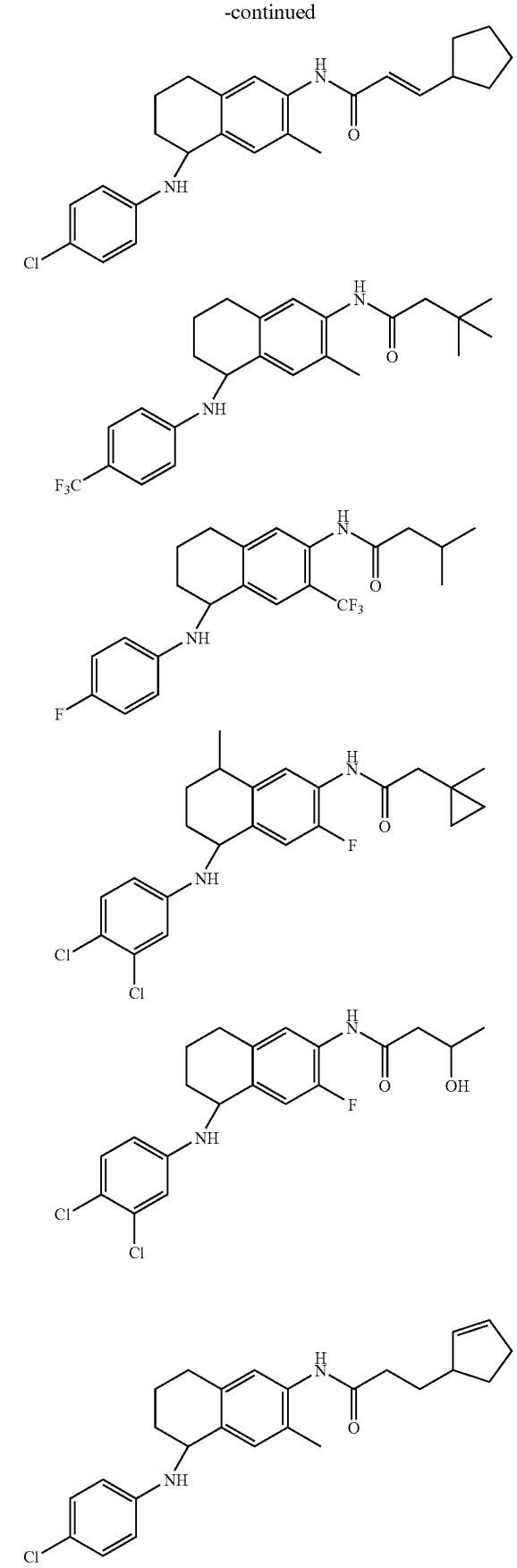

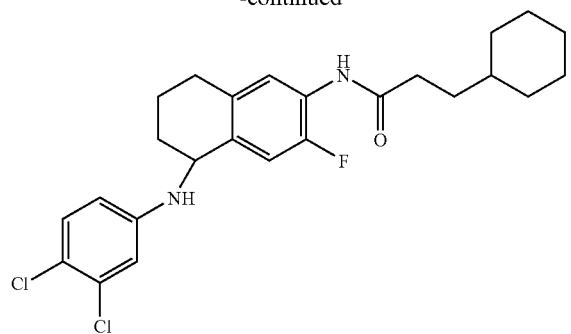
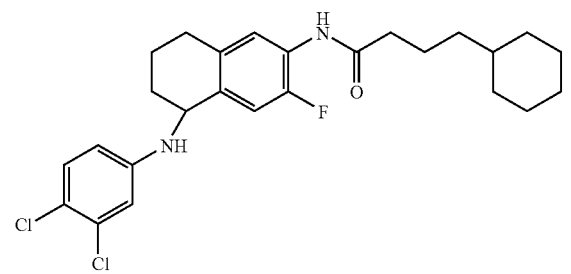
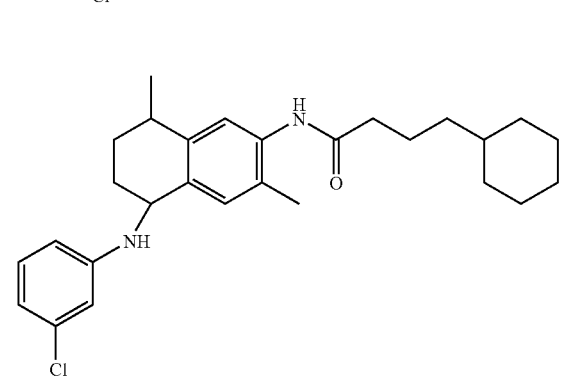
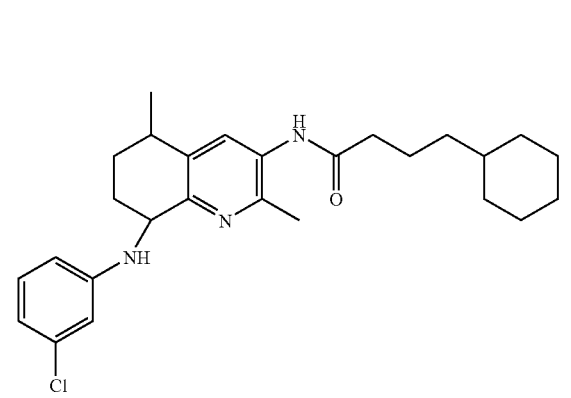
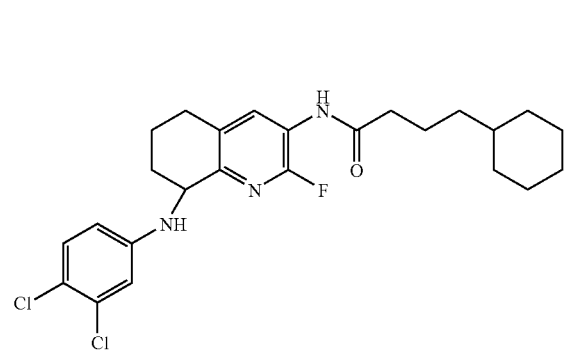
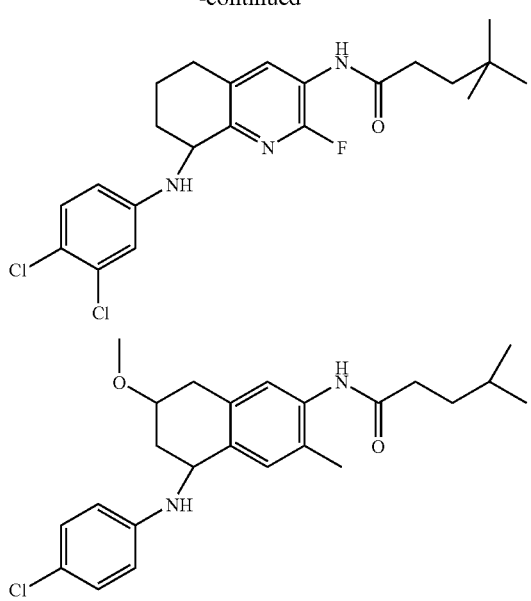
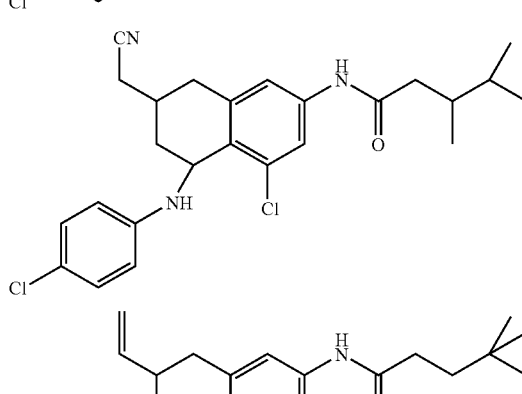
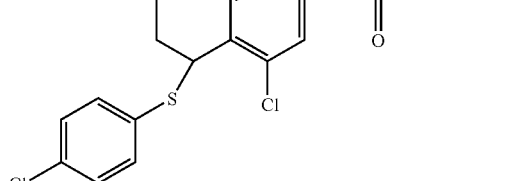
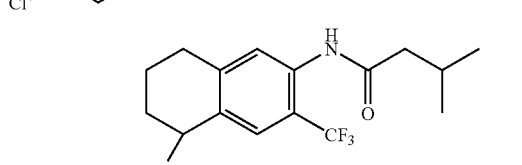
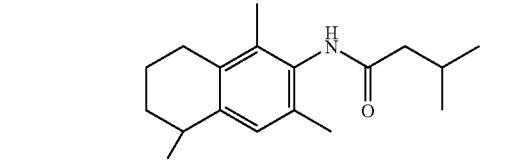

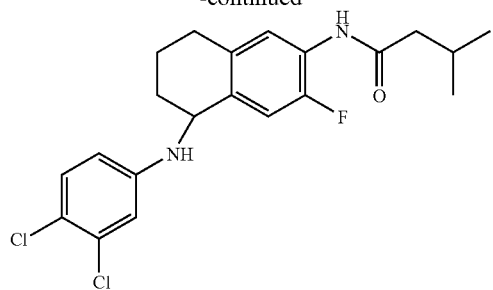
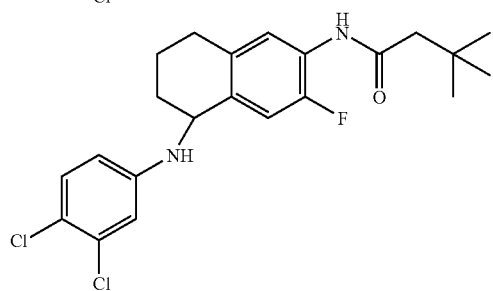
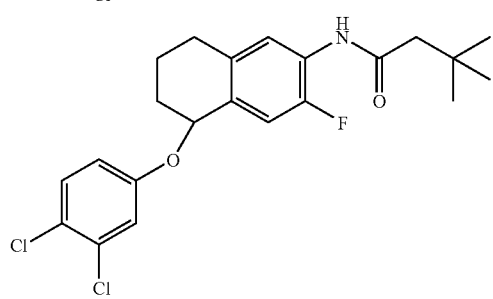
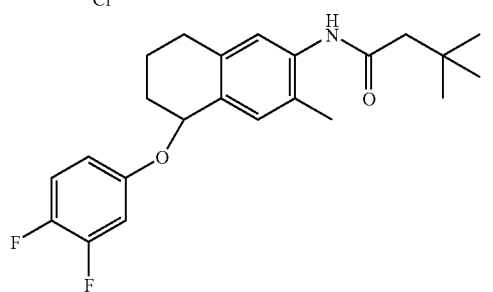
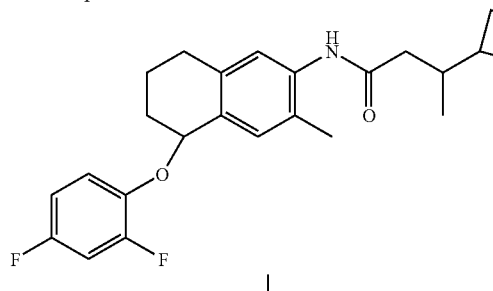
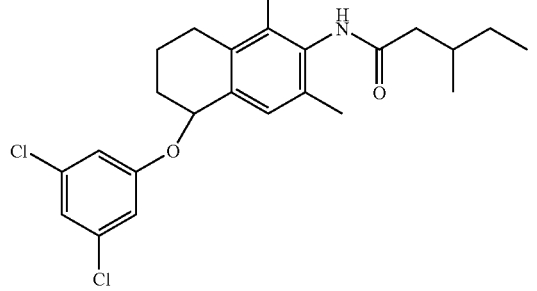
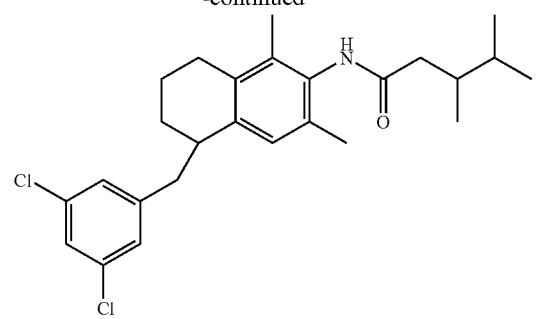
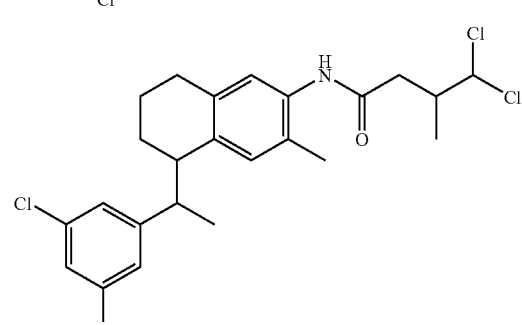
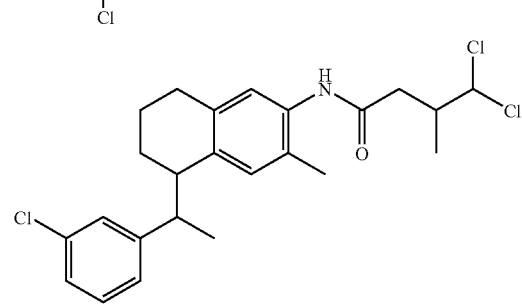
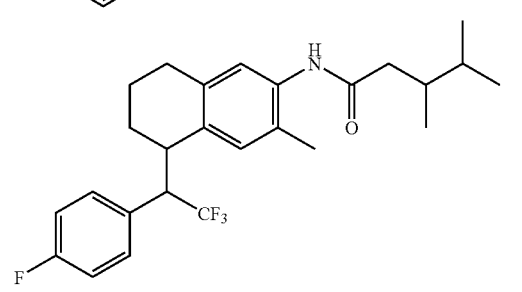
or a pharmaceutically acceptable salt or solvate thereof.
In yet another aspect according to the invention, there is provided a compound selected from the group consisting of:
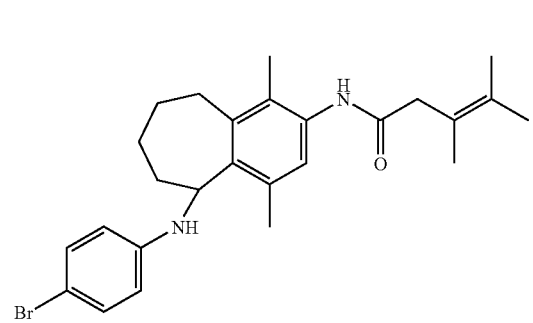

67
-continued
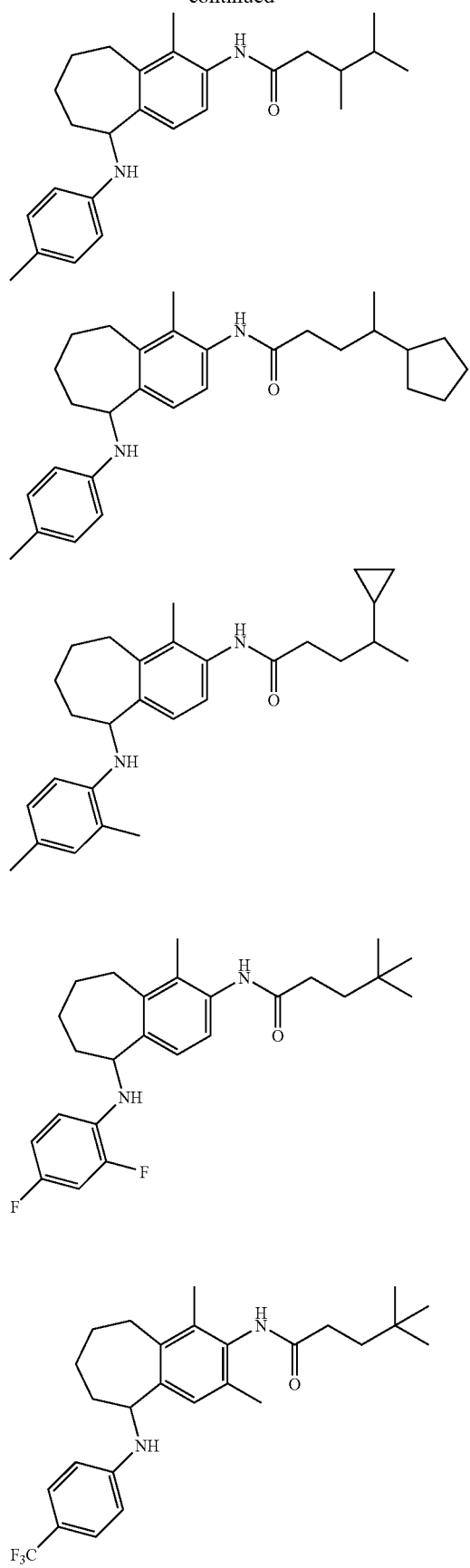
68
-continued
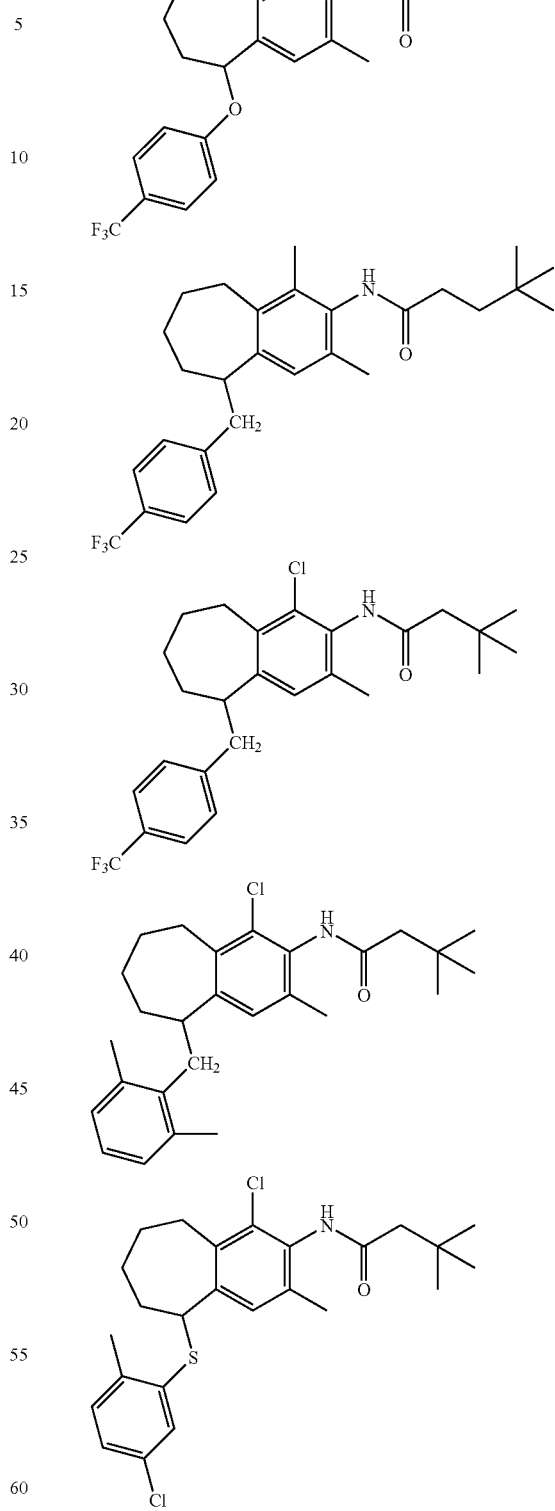
or a pharmaceutically acceptable salt or solvate thereof.
A pharmaceutically acceptable salt of a compound of the invention can be readily prepared by mixing together solutions of a compound of the invention and the desired acid or base, as appropriate. The salt can precipitate from solution and be collected by filtration or can be recovered by evaporation of the solvent. The degree of ionization in the salt can vary from completely ionized to almost non-ionized.

The compounds of the invention can exist in both unsolvated and solvated forms. The term 'solvate' is used herein to describe a molecular complex comprising a compound of the invention and one or more pharmaceutically acceptable solvent molecules, for example, ethanol, water and the like. The term 'hydrate' is included within the meaning of the term "solvate" and is frequently used when the solvent is water. Pharmaceutically acceptable solvates in accordance with the invention include solvates (hydrates) wherein the solvent of crystallization can be isotopically substituted, e.g. $D_2O$, $d_6$-acetone, $d_6$-DMSO.

The compounds of the invention which are complexes, such as clathrates and drug-host inclusion complexes are within the scope of the invention. In contrast to the aforementioned solvates, the drug and host are present in stoichiometric or non-stoichiometric amounts. also included are complexes containing two or more organic and/or inorganic components which can be in stoichiometric or non-stoichiometric amounts. The resulting complexes can be ionized, partially ionized, or non-ionized. For a review of such complexes, see J Pharm Sci, 64 (8), 1269-1288 by Haleblian (August 1975).

The compounds of the invention include all compounds of the invention, polymorphs and isomers thereof, including optical, geometric and tautomeric isomers as hereinafter defined and isotopically-labeled compounds.

The compounds of the invention containing one or more asymmetric carbon atoms can exist as two or more stereoisomers. Where a compound contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound can exhibit more than one type of isomerism.

All stereoisomers, geometric isomers and tautomeric forms of the compounds of the invention are included within the scope of the invention, including compounds exhibiting more than one type of isomerism, and mixtures of one or more thereof. also included are acid addition or base salts wherein the counterion is optically active, for example, D-lactate or L-lysine, or racemic, for example, DL-tartrate or DL-arginine.

Cis/trans isomers can be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) can be reacted with a suitable optically active compound, for example, an alcohol, or, in the case where the compound of the invention contains an acidic or basic moiety, an acid or base such as tartaric acid or 1-phenylethylamine. The resulting diastereomeric mixture can be separated by chromatography and/or fractional crystallization and one or both of the diastereoisomers converted to the corresponding pure enantiomer(s) by means well known to a skilled person.

Chiral compounds of the invention (and chiral precursors thereof) can be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers can be separated by conventional techniques known to those skilled in the art [see, for example, "Stereochemistry of Organic Compounds" by E. L. Eliel (Wiley, New York, 1994)].

The invention includes all pharmaceutically acceptable isotopically-labeled compounds of the invention, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, can afford certain therapeutic advantages resulting from greater metabolic stability, for example, increased in vivo half-life or reduced dosage requirements, and hence can be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

As used herein, the expressions "reaction-inert solvent" and "inert solvent" refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

One of ordinary skill will recognize that certain compounds of the invention can contain one or more atoms which can be in a particular stereochemical or geometric configuration, giving rise to stereoisomers and configurational isomers. all such isomers and mixtures thereof are included in the invention. Solvates (hydrates) of the compounds of the invention are also included.

Other features and advantages will be apparent from the specification and claims which describe the invention.

Illustrative examples of compounds of this invention have been provided above and are exemplified further below in the Examples. These illustrative examples are provided in order to indicate that a wide range of compounds and substitution patterns is included within the scope of the invention as described herein. This group of examples should not be construed as limiting the scope of this invention.

The invention further provides a method of treating or preventing a disorder characterized by hyperexcitability of the nervous system. The method includes administering to a subject in need thereof a therapeutically effective amount of a compound of formula I or a salt or solvate thereof. In one specific embodiment, the invention is directed to a method of preventing or treating a disease or disorder which is affected by activation voltage-gated potassium channels. The method includes administering to a patient in need thereof a therapeutically effective amount of a compound of formula I or a salt or ester or solvate thereof.

The compounds of the invention can be used to treat a wide variety of disorders characterized by hyperexcitability of the nervous system through modulation of $K^+$ channel activity. Modulation of ion channels refers to activating the ion channels, to affecting the kinetics of opening and closing of the ion channels, or to causing any change in the channel open probability of the ion channels. For example, the compounds of the invention are particularly useful at increasing the channel open probability of KCNQ2/3 channels in, for example, a mammalian subject including a human subject, by administering a therapeutically effective amount. The ability of the compounds of the invention to modulate potassium channels can be measured using the assay described below as well as other methods well known in the art.

For example, the compounds of the invention intended for pharmaceutical use can be administered as crystalline or amorphous products. They can be obtained, for example, as solid plugs, powders, or films by methods such as precipitation, crystallization, freeze drying, spray drying, or evaporative drying. Microwave or radio frequency drying can be used for this purpose.

The compounds of the invention intended for pharmaceutical use can be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation can be found, for example, in 'Remington's Pharmaceutical Sciences', 19th Edition (Mack Publishing Company, 1995).]

The compounds of the invention can be administered orally. Oral administration can involve swallowing, so that the compound enters the gastrointestinal tract, or buccal or sublingual administration can be employed by which the compound enters the blood stream directly from the mouth.

Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations.

Liquid formulations include suspensions, solutions, syrups and elixirs. Such formulations can be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations can also be prepared by the reconstitution of a solid, for example, from a sachet.

The compounds of the invention can also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug can make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets can also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets can also optionally comprise surface active agents, such as sodium lauryl sulfate and polysorbate 80, and glidants such as silicon dioxide and talc. When present, surface active agents can comprise from 0.2 wt % to 5 wt % of the tablet, and glidants can comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colorants, flavoring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends can be compressed directly or by roller to form tablets. Tablet blends or portions of blends can alternatively be wet-, dry-, or melt-granulated, melt congealed, or extruded before tabletting. The final formulation can comprise one or more layers and can be coated or uncoated; it can even be encapsulated. The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration can be formulated to be immediate and/or modified release. Modified release formulations include delayed-, sustained-, pulsed-, controlled-, targeted and programmed release.

The compounds of the invention can also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which can contain excipients such as salts, carbohydrates and buffering agents (preferably to a pH of 3 to 9), but, for some applications, they can be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, can readily be accomplished using standard pharmaceutical techniques well known to those skilled in the art.

The solubility of compounds of the invention used in the preparation of parenteral solutions can be increased by the use of appropriate formulation techniques, such as the incorporation of solubility-enhancing agents.

Formulations for parenteral administration can be formulated to be immediate and/or modified release. Thus, compounds of the invention can be formulated as a solid, semi-solid, or thixotropic liquid for administration as an implanted depot providing modified release of the active compound. Examples of such formulations include drug-coated stents and PLGA, [poly(lactide-co-glycolide)] microspheres.

The compounds of the invention can also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes can also be used. Typical carriers include alcohol, water, mineral oil, liquid petrolatum, white petrolatum, glycerin, polyethylene glycol and propylene glycol. Penetration enhancers can be incorporated [see, for example, J Pharm Sci, 88 (10), 955-958 by Finnin and Morgan (October 1999).]

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder can comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This can be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator can be formulated to contain a powder mix of the compound of the invention, a suitable powder base such as lactose or starch and a performance modifier such as 1-leucine, mannitol, or magnesium stearate. The lactose can be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist can contain from 1 µg to 20 mg of the compound of the invention per actuation and the actuation volume can vary from 1 µl to 100 µl. a typical formulation can comprise a compound of the invention, propylene glycol, sterile water, ethanol and sodium chloride. alternative solvents which can be used instead of propylene glycol include glycerol and polyethylene glycol.

Suitable flavors, such as menthol and levomenthol, or sweeteners, such as saccharin or saccharin sodium, can be added to those formulations of the invention intended for inhaled/intranasal administration.

Formulations for inhaled/intranasal administration can be formulated to be immediate and/or modified release using, for example, poly(DL-lactic-coglycolic acid (PGLA). Modified release formulations include delayed-, sustained-, pulsed-, controlled-, targeted and programmed release.

The compounds of the invention can be administered rectally or vaginally, for example, in the form of a suppository, pessary, or enema. Cocoa butter is a traditional suppository base, but various alternatives can be used as appropriate.

The compounds of the invention can also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. a polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gellan gum, can be incorporated together with a preservative, such as benzalkonium chloride. Such formulations can also be delivered by iontophoresis.

The compounds of the invention can be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes can be used. as an alternative to direct complexation with the drug, the cyclodextrin can be used as an auxiliary additive, i.e. as a carrier, diluent, or solubilizer. Most commonly used for these purposes are alpha-, beta- and gamma-cyclodextrins, examples of which can be found in International Patent Applications Nos. WO 91/11172, WO 94/02518 and WO 98/55148.

Dosage ranges are based on an average human subject having a weight of about 65 kg to 70 kg. The physician will readily be able to determine doses for subjects whose weight falls outside this range, such as infants and the elderly. Depending on the disease and condition of the patient, the term "treatment" as used herein can include one or more of curative, palliative and prophylactic treatment.

As directed by this invention and exemplified above, compounds of formula I are designed for oral or intravenous dosing of up to 2000 mg per day. Yet the high activities of many of these compounds indicate that dosing of less than 1200 mg per day in humans can be administered. A therapeutically effective amount or dose of the compounds of the invention can be determined using the assays exemplified below as well as others well known in the art.

Thus, this invention comprises tablets, capsules, solutions, and suspensions of compounds of formula I which are formulated for oral administration. Similarly, solutions and suspensions suitable for oral pediatric administration, comprising, in addition to compounds of formula I, a syrup such as sorbitol or propylene glycol, among many other examples, are also directed to the invention. More specifically, solutions and suspensions comprising, in addition to compounds of formula I, a syrup such as sorbitol or propylene glycol, along with colorants and flavorings suitable for oral pediatric administration, are also directed to the invention. Additionally, both chewable and non-chewable tablets comprising compounds of formula I, along with pharmaceutically acceptable tabletting agents and other pharmaceutically acceptable carriers and excipients, are also directed to the invention.

Therefore, in one embodiment the invention is directed to a method of treating or preventing a disease, disorder, or condition that is affected by modulation of potassium ion channels in a patient comprising administration of a compound of formula I in an amount of up to 2000 mg per day.

In another embodiment, this invention is directed to a method of treating or preventing a disease, disorder, or condition that is affected by modulation of potassium ion channels in a patient comprising administration of a compound of formula I in an amount of from about 10 mg to about 2000 mg per day.

In a more specific embodiment, this invention is directed to a method of treating or preventing a seizure disorder in a patient comprising administration of a compound of formula I in an amount of up to about 2000 mg per day.

In another embodiment, this invention is directed to a method of treating or preventing a seizure disorder in a patient comprising administration of a compound of formula I in an amount of from about 10 mg per day to about 2000 mg per day.

In another embodiment, this invention is directed to a method of treating or preventing a seizure disorder in a patient comprising administration of a compound of formula I in an amount of from about 300 mg per day to about 2000 mg per day.

In another embodiment, this invention is directed to a method of treating or preventing a seizure disorder in a patient comprising administration of a compound of formula I in an amount of from about 300 mg per day to about 1200 mg per day.

EXAMPLES

In the examples described below, unless otherwise indicated, all temperatures are set forth in degrees Celsius and all parts and percentages are by weight. Reagents can be purchased from commercial suppliers, such as Sigma-Aldrich Chemical Company, Acros Organics, or Lancaster Synthesis Ltd. and can be used without further purification unless otherwise indicated. Tetrahydrofuran (THF), methylene chloride ($CH_2Cl_2$ or DCM), N,N-dimethylacetamide (DMA), acetonitrile (MeCN), and N,N-dimethylformamide (DMF) can be purchased from Aldrich in Sure-Seal bottles and used as received. All solvents can be purified using standard methods known to those skilled in the art, unless otherwise indicated. Diethyl ether is abbreviated as $Et_2O$. Ethyl acetate is abbreviated as EtOAc. Trifluoroacetic acid is abbreviated as TFA. Acetic acid is abbreviated as HOAc or AcOH. Similarly, acetyl chloride is abbreviated as AcCl. Coupling reagent O-(7-azabenzotriazol-1-yl)-N,N,N',N'-tetra-methyluronium hexafluorophosphate is abbreviated as HATU. Trifluoromethanesulfonate, or triflate, is abbreviated as "OTf." T-Butyldimethylsilyl is abbreviated as TBS. Tert-Butoxycarbonyl is abbreviated as BOC. N,N-Di-isopropyl-N-ethylamine is abbreviated as i-$Pr_2$NEt. 4-(N,N-Dimethylamino) pyridine is abbreviated as DMAP.

The reactions set forth below were performed generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 pre-coated plates (Merck Art 5719) and eluted with appropriate solvent ratios (v/v). Reactions were assayed by TLC or LCMS and terminated as judged by the consumption of starting material. Visualization of the TLC plates was done with UV light (254 nm wavelength) or with an appropriate TLC visualizing solvent and activated with heat. Analytical HPLC was performed with Waters or Agilent instruments. Flash column chromatography (Still et al., *J. Org. Chem.*, 1978, 43, 2923) was performed using silica gel 60 (Merck Art 9385) or various MPLC systems, such as Biotage or ISCO purification system. Preparative HPLC routinely performed on Prep LC 4000 system from Water with Ultra 120 10 mm C8 column from Peeke Scientific for single compounds; combinational, solution-based samples described in detail herein. Microwave chemistry was carried out using an Emrys™ Optimizer EXP from Personal Chemistry, Inc. (now Biotage).

The compound structures in the examples below were confirmed by one or more of the following methods: proton magnetic resonance spectroscopy, mass spectroscopy, and elemental microanalysis. Proton magnetic resonance ($^1$H NMR) spectra were determined using a Bruker spectrometer operating at field strength of 300 or 400 megahertz (MHz). Chemical shifts are reported in parts per million (ppm, δ) downfield from an internal tetramethylsilane standard. Alternatively, $^1$H NMR spectra were referenced relative to signals from residual protons in deuterated solvents as follows: $CDCl_3$=7.25 ppm; DMSO-$d_6$=2.49 ppm; $CD_3CN$=1.94 ppm, $CD_3OD$ or methanol-$d_4$=3.30 ppm; $C_6D_6$=7.16 ppm. Peak multiplicities are designated as follows: s, singlet; d, doublet; dd, doublet of doublets; t, triplet; dt, doublet of triplets; q, quartet; br, broadened; m, multiplet. Coupling constants are given in Hertz (Hz). Mass spectra (MS) data were obtained using Shimadzu SCL-10A and Waters LC mass spectrometer with APCI or ESI ionization. Elemental microanalyses were performed by Atlantic Microlab Inc., and gave results for the elements stated within ±0.4% of the theoretical values.

Preferred compounds in accordance with the invention can be prepared in manners analogous to those specifically described below.

The examples and preparations provided below further illustrate and exemplify the compounds of the present invention and methods of preparing such compounds. It is to be understood that the scope of the present invention is not limited in any way by the scope of the following examples and preparations. The skilled artisan will recognize that different acids, amines, alkyl halides, aryl halides, coupling reagents, and heterocycles can be substituted in the following descriptions to suit the preparations of a desired embodiment. The following methods can be scaled upwards or downwards to suit the amount of desired material.

Example 1
This Example illustrates chemical synthesis of compounds of formulas XI, XVI, XXI and XXII.
Section I. The preparation of compounds of formula XI is outlined in Scheme 1.
Scheme 1:
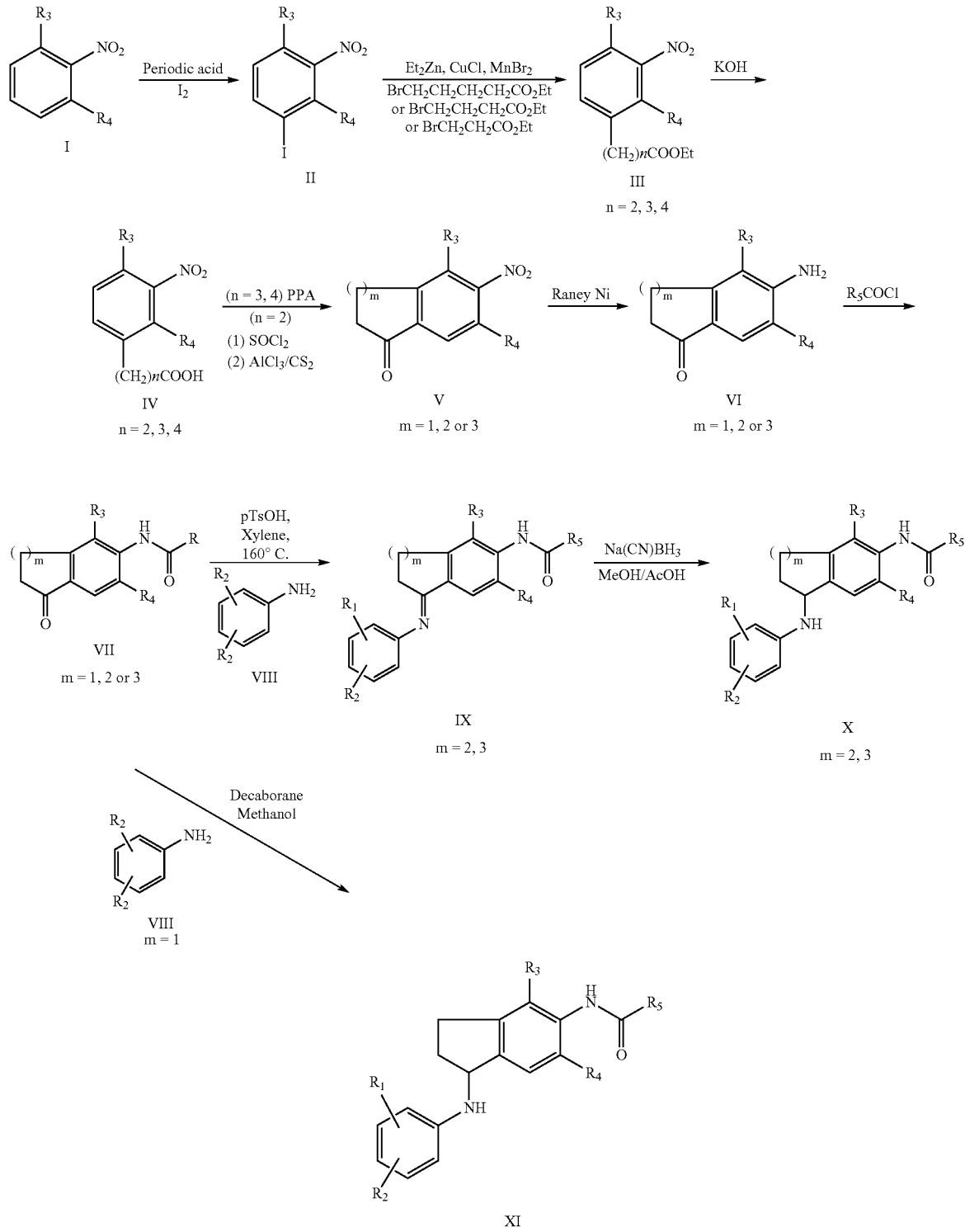

Section II. The preparation of compounds of formula XVI is outlined in Scheme 2.
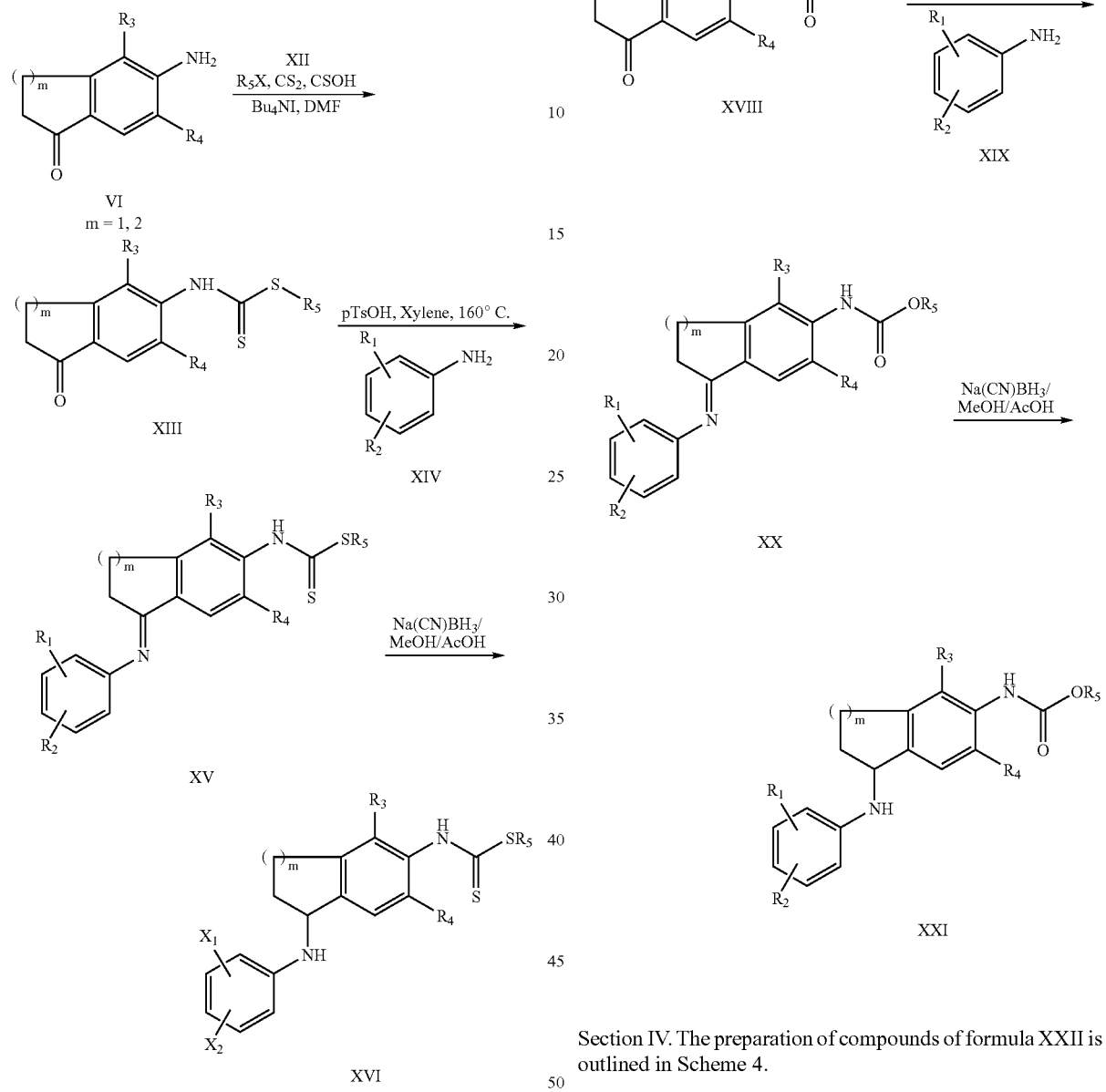
Section III. The preparation of compounds of formula XXI is outlined in Scheme 3.
Scheme 3:
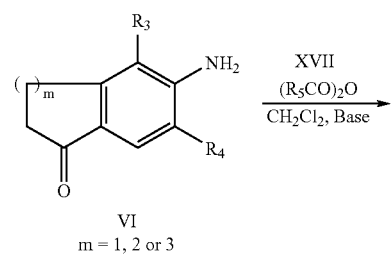
Section IV. The preparation of compounds of formula XXII is outlined in Scheme 4.
Scheme 4:
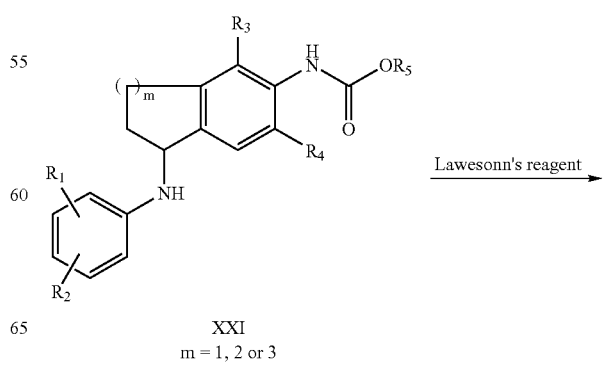

81

-continued

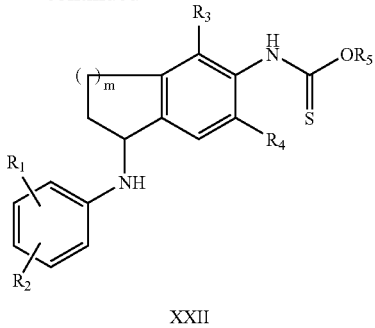

XXII

Compounds of this invention can be prepared by a variety of methods. The procedures below are intended to illustrate those methods, and the examples given are intended to illustrate the scope of this invention. Neither the methods not the examples should be construed as limiting the invention in any way.

Example 2

Examples 2 through 19 illustrate NMR data of several functionalities pertaining to the compound of Formula I.

N-(5-(4-fluorophenylamino)-1,3-dimethyl-5,6,7,8-tetrahydronaphthalen-2-yl)-3,3-dimethylbutanamide Step A: 5-Iodo-1,3-dimethyl-2-nitrobenzene

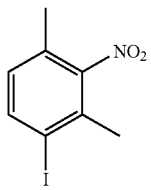

To a mixture of 2,6-dimethylnitrobenzene (151 g, 1.0 mol), acetic acid (1200 ml), and conc. $H_2SO_4$ (60 ml) was added iodine (102 g, 0.4 mol) and periodic acid dehydrate (205 g, 0.9 mol). The resulting solution was heated at 90° C. for 4 days. After cooling to room temperature, the reaction mixture was diluted with water (2000 ml). The yellow crystals were filtered and washed with water to give 220 g of pure product (79%). $^1$H-NMR δ (DMSO-$d_6$, 300 MHz): 7.95 (d, J=7.8 Hz, 1H), 7.08 (d, J=7.8 Hz, 1H), 2.27 (s, 3H), 2.16 (s, 3H).

Step B: Ethyl 4-(2,4-dimethyl-3-nitrophenyl)butanoate

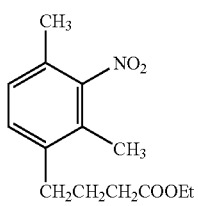

82

A three-necked flask equipped with a thermometer, a gas inlet, and a magnetic stirring bar was charged under argon with $MnBr_2$ (320 mg, 1.5 mmol) in DMPU (25 ml). CuCl (85 mg, 1 mmol), ethyl 4-bromobutyrate (5.85 g, 30 mmol) and $Et_2Zn$ (2.7 ml, 27 mmol) were successively added. The reaction mixture turned dark red and was stirred for 4 h at 25° C. After cooling to −30° C., a solution of $Cl_2Pd(dppf)$ (0.925 g, 10 mmol) and 2,4-dimethyl-3-nitroiodobenzene (6.93 g, 25 mmol) in anhydrous THF (25 ml) was slowly added. The reaction mixture was warmed to 25° C. for 30 min and was then stirred at 65° C. overnight and quenched with an aqueous 2N HCl solution (100 ml). This mixture was extracted with $CH_2Cl_2$ three times, and the organic layer was dried over anhydrous $Na_2SO_4$. The solvent was removed under reduced pressure, and the crude residue obtained was purified by Biotage (hexane/EtOAc, 0-30%, 40 min) to give 4.5 g of yellow oily products (68%). $^1$H-NMR δ (CDCl$_3$, 300 MHz): 7.13 (d, J=7.8 Hz, 1H), 7.03 (d, J=7.8 Hz, 1H), 4.12 (q, J=7.2 Hz, 2H), 2.64 (t, J=7.8 Hz, 2H), 2.34 (t, J=7.8 Hz, 2H), 2.23 (s, 3H), 2.20 (s, 3H), 1.86 (m, J=7.8 Hz, 2H), 1.24 (t, J=7.8 Hz, 3H).

Step C: 4-(2,4-Dimethyl-3-nitrophenyl)butanoic acid

A suspension of 4-(2,4-dimethyl-3-nitro-phenyl)-butyric acid ethyl ester (4 g, 16.9 mmol) in 100 ml of 5% KOH was refluxed at 120° C. for 4 hours. This reaction was then cooled to 0° C. and neutralized with 10% HCl to pH 3-4. The resulting solid was filtered and washed with water. After drying under reduced pressure at 40° C., 3.19 g (80%) of pure product as a white solid was obtained. $^1$H-NMR δ (DMSO-$d_6$, 300 MHz): 12.12 (brs, 1H, exchangeable with $D_2O$), 7.26 (d, J=7.8 Hz, 1H), 7.20 (d, J=7.8 Hz, 1H), 2.61 (t, J=7.8 Hz, 2H), 2.25 (t, J=7.8 Hz, 2H), 2.17 (s, 3H), 2.13 (s, 3H), 1.70 (m, J=7.8 Hz, 2H).

Step D: 5,7-Dimethyl-6-nitro-3,4-dihydronaphthalen-1(2H)-one

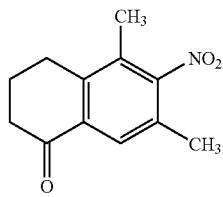

PPA (100 g) was warmed to 110° C. and 4-(2,4-dimethyl-3-nitrophenyl)butanoic acid (3.04 g, 12.8 mmol) was added. The resulting solid slowly turn to a brown solution. The reaction was stirred at 110° C. for 4 hours, then poured into 200 ml of water with strong stirring. The mixture was extracted with dichloromethane (×3), and the organic solution was dried over anhydrous $Na_2SO_4$ and evaporated to dryness. The residue was purified by Biotage (hexane/EtOAc, 0-30%, 40 min) to give pure compounds as yellow solid (2 g, 71%).

Step E: 6-Amino-5,7-dimethyl-3,4-dihydronaphthalen-1(2H)-one

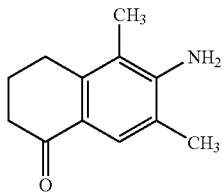

To a solution of 5,7-dimethyl-6-nitro-3,4-dihydronaphthalen-1(2H)-one (1 g, 4.56 mmol) in 50 ml of methanol was added a catalytic amount of Raney Ni. The mixture was hydrogenated under regular pressure at room temperature for 4 hours and filtered through Celite and washed with methanol. The filtrate was evaporated to dryness under reduced pressure and dried in vacuo to give the crude product, which is pure enough for next step. $^1$H-NMR δ (CDCl$_3$, 300 MHz): 7.77 (s, 1H), 4.09 (brs, 2H, exchangeable with D$_2$O), 2.85 (t, J=6.0 Hz, 2H), 2.54 (t, J=6.0 Hz, 2H), 2.19 (s, 3H), 2.09 (s, 3H), 2.10 (m, 2H).

Step F: N-(1,3-dimethyl-5-oxo-5,6,7,8-tetrahydronaphthalen-2-yl)-3,3-dimethylbutanamide

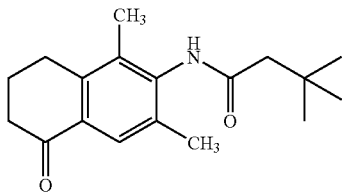

To a solution of 6-amino-5,7-dimethyl-3,4-dihydronaphthalen-1(2H)-one (1 g, 5.3 mmol) and triethylamine (1.07 g, 10.6 mmol) in anhydrous dichloromethane (20 ml) was added dropwise tert-butylacetyl chloride (0.78 g, 5.8 mmol) at room temperature. The reaction mixture was stirred an additional 3 hours at this temperature. The solvent was removed under reduced pressure, and the residue was purified by Biotage (hexane/EtOAc, 0-40%, 40 min) to give a white solid (1.4 g, 92%). $^1$H-NMR δ (CDCl$_3$, 300 MHz): 7.82 (s, 1H), 6.73 (brs, 1H, exchangeable with D$_2$O), 2.85 (t, J=6.0 Hz, 2H), 2.60 (t, J=6.0 Hz, 2H), 2.33 (s, 2H), 2.27 (s, 3H), 2.18 (s, 3H), 2.15 (m, J=6.0 Hz, 2H), 1.16 (s, 9H). MS: 288 (M+1).

Step G: N-(5-(4-fluorophenylamino)-1,3-dimethyl-5,6,7,8-tetrahydro naphthalen-2-yl)-3,3-dimethylbutanamide

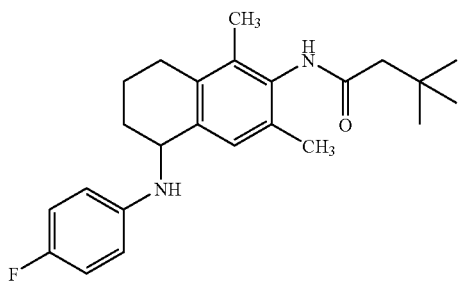

A mixture of N-(1,3-dimethyl-5-oxo-5,6,7,8-tetrahydronaphthalen-2-yl)-3,3-dimethylbutanamide (150 mg, 0.52 mmol), 4-fluoroaniline (116 mg, 1.04 mmol), and pTSA (20 mg) in 20 ml of m-xylene was heated at 160° C. for 6 hours. The solvent was removed in vacuo, and the residue was dissolved in a mixture of methanol (10 ml) and acetic acid (2 ml). Sodium cyanoborohydride (49 mg, 0.78 mmol) was added, and the resulting mixture was stirred at room temperature for 2 hours. After neutralization with saturated sodium bicarbonate, the mixture was extracted with chloroform (×3). The organic layer were combined, dried over anhydrous Na$_2$SO$_4$ and evaporated to dryness in vacuo. The residue was purified by Biotage (hexane/EtOAc, 0-30%, 40 min) to give a white solid (75 mg, 38%). $^1$H-NMR δ (DMSO-d$_6$, 500 MHz): 9.09 (brs, 1H, exchangeable with D$_2$O), 7.00 (s, 1H), 6.89 (t, J=7.5 Hz, 2H), 6.65 (dd, J=5.7 and 7.5 Hz, 2H), 5.70 (brs, 1H, exchangeable with D$_2$O), 4.45 (m, 1H), 2.61 (m, 1H), 2.51 (m, 1H), 2.20 (s, 2H), 2.06 (s, 3H), 1.99 (s, 3H), 1.84 (m, 1H), 1.73 (m, 3H), 1.04 (s, 9H). MS: 383 (M+1).

Example 3

(−)N-(5-(4-fluorophenylamino)-1,3-dimethyl-5,6,7,8-tetrahydro naphthalen-2-yl)-3,3-dimethylbutanamide (−)N-(5-(4-fluorophenylamino)-1,3-dimethyl-5,6,7,8-tetrahydro naphthalen-2-yl)-3,3-dimethylbutanamide was obtained by chiral HPLC using the following condition: column: CHIRALCEL® AD-H® (250×20 mm); Eluent: hexane/isopropanol (95/5); Flow Rate: 12 ml/min; Temperature: room temperature; UV detection: 254 nm; Run Time. 60 min.
[α]$_D$−11.51 (methanol, 25° C.), Retention Time: 24.6 min.

Example 4

(+)N-(5-(4-fluorophenylamino)-1,3-dimethyl-5,6,7,8-tetrahydro naphthalen-2-yl)-3,3-dimethylbutanamide (+)N-(5-(4-fluorophenylamino)-1,3-dimethyl-5,6,7,8-tetrahydro naphthalen-2-yl)-3,3-dimethylbutanamide was obtained by chiral HPLC using the condition previously described.
[α]$_D$+10.67 (methanol, 25° C.), Retention Time: 28.0

Example 5

N-(1,3-dimethyl-5-(4-(trifluoromethyl)phenylamino)-5,6,7,8-tetrahydronaphthalen-2-yl)-3,3-dimethylbutanamide

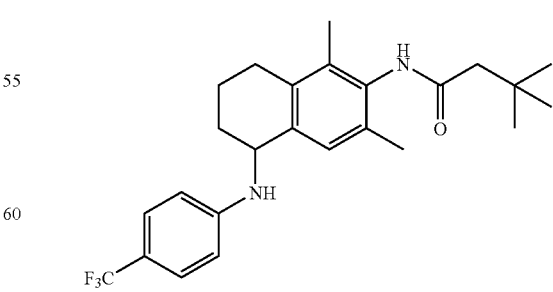

This compound was synthesized using the same procedure described above (example 2). $^1$H-NMR δ (DMSO-d$_6$, 300 MHz): 9.11 (brs, 1H, exchangeable with D$_2$O), 7.35 (d, J=8.4

Hz, 2H), 6.95 (s, 1H), 6.77 (d, J=8.4 Hz, 2H), 6.64 (d, J=6.9 Hz, 1H, exchangeable with D$_2$O), 4.58 (m, 1H), 2.61 (m, 1H), 2.51 (m, 1H), 2.20 (s, 2H), 2.06 (s, 3H), 2.00 (s, 3H), 1.85 (m, 1H), 1.77 (m, 3H), 1.04 (s, 9H). MS: 433 (M+1).

Example 6

N-(1,3-dimethyl-5-(3,4-dichlorophenylamine)-5,6,7,8-tetrahydronaphthalen-2-yl)-3,3-dimethylbutanamide

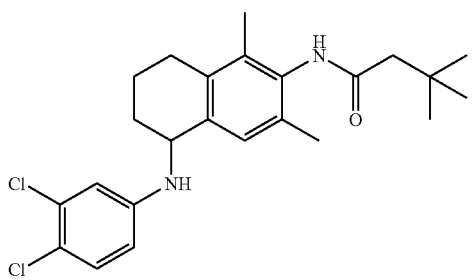

This compound was synthesized using the same procedure described above (example 2). $^1$H-NMR δ (DMSO-d$_6$, 400 MHz): 9.11 (brs, 1H, exchangeable with D$_2$O), 7.25 (d, J=9.0 Hz, 1H), 6.97 (s, 1H), 6.88 (d, J=2.5 Hz, 1H), 6.67 (dd, J=2.5 and 9.0 Hz, 1H), 6.37 (d, J=6.9 Hz, 1H, exchangeable with D$_2$O), 4.58 (m, 1H), 2.61 (m, 1H), 2.51 (m, 1H), 2.22 (s, 2H), 2.09 (s, 3H), 2.02 (s, 3H), 1.83 (m, 1H), 1.75 (m, 3H), 1.06 (s, 9H). MS: 433 (M+1).

Example 7

N-(1,3-dimethyl-5-(4-chlorophenylamino)-5,6,7,8-tetrahydronaphthalen-2-yl)-3,3-dimethylbutanamide

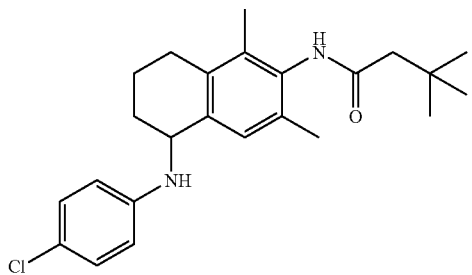

This compound was synthesized using the same procedure described above (example 2). $^1$H-NMR δ (DMSO-d$_6$, 400 MHz): 9.10 (brs, 1H, exchangeable with D$_2$O), 7.08 (d, J=8.4 Hz, 2H), 6.99 (s, 1H), 6.68 (d, J=8.4 Hz, 2H), 6.52 (brs, 1H, exchangeable with D$_2$O), 4.50 (m, 1H), 2.61 (m, 1H), 2.51 (m, 1H), 2.22 (s, 2H), 2.08 (s, 3H), 2.02 (s, 3H), 1.85 (m, 1H), 1.75 (m, 3H), 1.06 (s, 9H). MS: 399 (M+1).

Example 8

N-(1,3-dimethyl-5-(4-bromophenylamino)-5,6,7,8-tetrahydronaphthalen-2-yl)-3,3-dimethylbutanamide

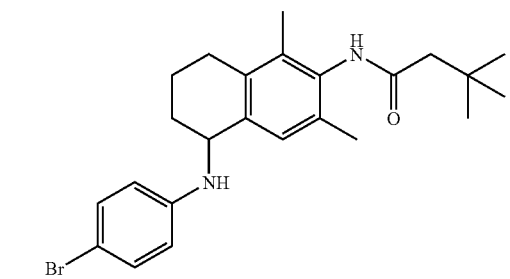

This compound was synthesized using the same procedure described above (example 2). $^1$H-NMR δ (DMSO-d$_6$, 400 MHz): 9.10 (brs, 1H, exchangeable with D$_2$O), 7.19 (d, J=8.4 Hz, 2H), 6.99 (s, 1H), 6.65 (d, J=8.4 Hz, 2H), 6.51 (d, J=6.9 Hz, 1H, exchangeable with D$_2$O), 4.50 (m, 1H), 2.61 (m, 1H), 2.51 (m, 1H), 2.22 (s, 2H), 2.08 (s, 3H), 2.02 (s, 3H), 1.85 (m, 1H), 1.75 (m, 3H), 1.06 (s, 9H). MS: 443 (M+1).

Example 9

N-(1,3-dimethyl-5-(3-chlorophenylamino)-5,6,7,8-tetrahydronaphthalen-2-yl)-3,3-dimethylbutanamide

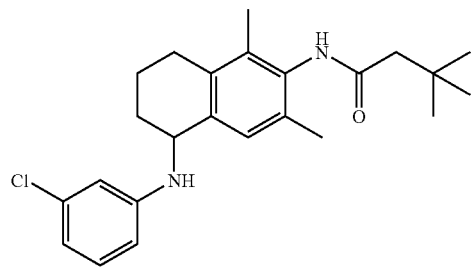

This compound was synthesized using the same procedure described above (example 2). $^1$H-NMR δ (DMSO-d$_6$, 400 MHz): 9.11 (brs, 1H, exchangeable with D$_2$O), 7.07 (t, J=8.0 Hz, 1H), 6.99 (s, 1H), 6.71 (t, J=1.8 Hz, 1H), 6.64 (dd, J=1.8 and 8.0 Hz, 1H), 6.51 (dd, J=1.8 and 8.0 Hz, 1H), 6.15 (brs, 1H, exchangeable with D$_2$O), 4.54 (m, 1H), 2.62 (m, 1H), 2.51 (m, 1H), 2.22 (s, 2H), 2.09 (s, 3H), 2.02 (s, 3H), 1.85 (m, 1H), 1.76 (m, 3H), 1.07 (s, 9H). MS: 399 (M+1).

Example 10

N-(1,3-dimethyl-5-(3,5-difluorophenylamino)-5,6,7,8-tetrahydronaphthalen-2-yl)-3,3-dimethylbutanamide

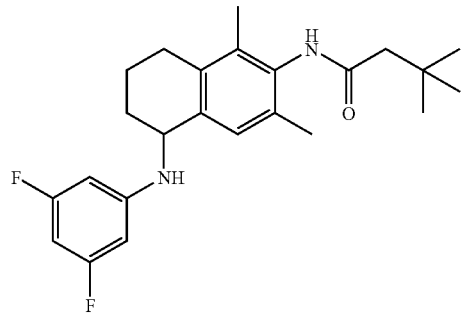

This compound was synthesized using the same procedure described above (example 2). $^1$H-NMR δ (DMSO-d$_6$, 400 MHz): 9.12 (brs, 1H, exchangeable with D$_2$O), 6.97 (s, 1H), 6.56 (brs, 1H, exchangeable with D$_2$O), 6.34 (dd, J=2.0 and 10.8 Hz, 2H), 6.18 (tt, J=2.0 and 8.0 Hz, 1H), 4.55 (m, 1H), 2.63 (m, 1H), 2.51 (m, 1H), 2.22 (s, 2H), 2.09 (s, 3H), 2.02 (s, 3H), 1.85 (m, 1H), 1.76 (m, 3H), 1.07 (s, 9H). MS: 401 (M+1).

Example 11

N-(1-(4-fluorophenylamino)-4,6-dimethyl-2,3-dihydro-1H-inden-5-yl)-3,3-dimethylbutanamide Step A: Ethyl 3-(2,4-dimethyl-3-nitrophenyl)propanoate

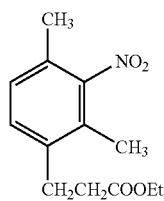

Method A: To a solution of 2,4-dimethyl-3-nitroiodobenzene (140 g, 0.51 mol), acrolein diethylacetal (229 ml, 1.5 mol), n-Bu$_4$NCl (139 g, 0.5 mol), n-Bu$_3$N (238 ml, 1.0 mol) in 2000 ml of DMF, Pd(OAc)$_2$ (3.4 g, 0.015 mol) was added. The mixture was warmed at 90° C. and stirred for 2 hours. After cooling, the reaction mixture was diluted with 2N HCl and extracted with diethyl ether. The organic layer was dried over anhydrous sodium sulfate and concentrated under reduced pressure. The residue was used for next step without further purification. An analytically pure sample was obtained by chromatography (ISCO, hexane/ethyl acetate, 0-30%, 40 min). $^1$H-NMR δ (DMSO-d$_6$, 300 MHz): 7.27 (d, J=7.8 Hz, 1H), 7.16 (d, J=7.8 Hz, 1H), 4.03 (q, J=7.2 Hz, 2H), 2.87 (t, J=7.8 Hz, 2H), 2.57 (t, J=7.8 Hz, 2H), 2.16 (s, 3H), 2.13 (s, 3H), 1.14 (t, J=7.2 Hz, 3H).

Method B: This compound was synthesized using the procedure described in example 2, step B, from 5-iodo-1,3-dimethyl-2-nitrobenzene (see example 2) and ethyl 3-bromopropanoate.

Step B: 3-(2,4-Dimethyl-3-nitrophenyl)propanoic acid

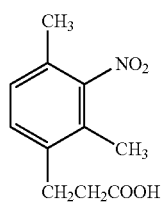

This compound was synthesized using the procedure described in example 2, step C. $^1$H-NMR δ (DMSO-d$_6$, 300 MHz): 12.21 (brs, 1H, exchangeable with D$_2$O), 7.29 (d, J=7.8 Hz, 1H), 7.20 (d, J=7.8 Hz, 1H), 2.84 (t, J=7.8 Hz, 2H), 2.49 (t, 7.8 Hz, 2H), 2.17 (s, 3H), 2.13 (s, 3H).

Step C: 4,6-Dimethyl-5-nitro-2,3-dihydro-1H-inden-1-one

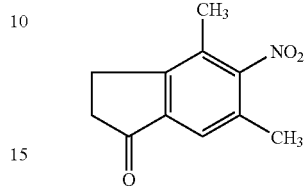

A stirred solution of 5-(2,4-dimethyl-3-nitro-phenyl)-propionic acid (115 g, 0.52 mol) and thionyl chloride (74.2 g, 0.63 mol) in 350 ml of anhydrous methylene chloride was heated under reflux for 16 hours under argon. The reaction mixture was concentrated under reduced pressure to give a residue, which was dissolved in 150 ml of anhydrous methylene chloride. The solution was concentrated under reduced pressure, and the residue was subjected to high vacuum to give 5-(2,4-dimethyl-3-nitro-phenyl)-propionyl chloride as an yellow oil.

A stirred mixture of anhydrous aluminum chloride (86.7 g, 0.65 mol) and 400 ml of carbon disulfide was cooled to 5° C., and a solution of 5-(2,4-dimethyl-3-nitro-phenyl)-propionyl chloride from above in 150 ml of carbon disulfide was added dropwise. During the addition the temperature of the reaction mixture was maintained at 5-10° C. Upon complete addition, the reaction mixture was stirred at 5° C. for 15 min, at room temperature for 30 min, then under reflux for 4 hours, and finally at room temperature for 16 hours. The reaction mixture was poured into 150 ml of ice-water, and the mixture was stirred for one hour and extracted with four portions of 400 ml each of diethyl ether. The combined ether extracts were dried over anhydrous sodium sulfate, filtered, and the filtrate concentrated under reduced pressure to give solid residue. The residue was crystallized from methanol after treatment with decolorizing carbon to give 5-nitro-4,6-dimethyl-indan-1-one as yellowish solids (90 g, 84%). $^1$H-NMR δ (DMSO-d$_6$, 300 MHz): 7.56 (s, 1H), 3.04 (t, J=5.7 Hz, 2H), 2.69 (t, J=5.7 Hz, 2H), 2.27 (s, 3H), 2.22 (s, 3H).

Step D: 5-Amino-4,6-dimethyl-2,3-dihydro-1H-inden-1-one

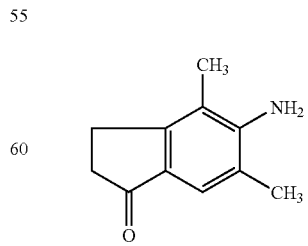

This compound was synthesized using the procedure described in example 2, step E. $^1$H-NMR δ (CDCl$_3$, 300

MHz): 7.11 (s, 1H), 5.59 (brs, 2H, exchangeable with D₂O), 2.82 (t, J=5.7 Hz, 2H), 2.42 (t, J=5.7 Hz, 2H), 2.10 (s, 3H), 2.02 (s, 3H).

Step E: 3,3-Dimethyl-N-(4-methyl-1-oxo-2,3-dihydro-1H-inden-5-34)butanamide

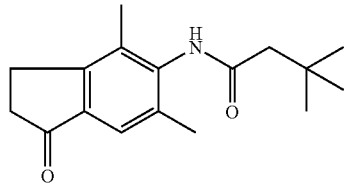

This compound was synthesized using the procedure described in example 2, step F. ¹H-NMR δ (DMSO-d₆, 300 MHz): 7.47 (s, 1H), 3.01 (t, J=5.7 Hz, 2H), 2.67 (t, J=5.7 Hz, 2H), 2.38 (s, 2H), 2.09 (s, 3H), 2.06 (s, 3H), 0.97 (s, 9H).

Step F: N-(1-(4-fluorophenylamino)-4,6-dimethyl-2,3-dihydro-1H-inden-5-yl)-3,3-dimethylbutanamide

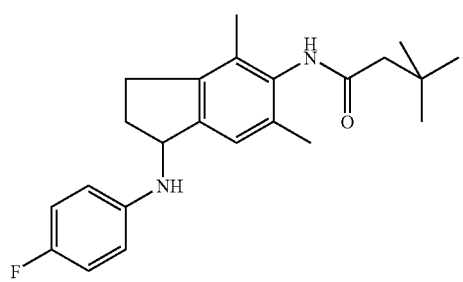

A mixture of N-(4,6-dimethyl-1-oxo-indan-5-yl)-3,3-dimethyl-butyramide (5 g, 19 mmol), 4-fluoroaniline (5 g, 45 mmol), and decaborane (4.5 g, 36.8 mmol) in 100 ml of anhydrous methanol was stirred for 2 days at room temperature in an high pressure reaction equipment. The reaction mixture was poured into 500 ml of ice-water with strong stirring and the precipitates were filtered and washed with water. The dried solid was crystallized from hexane/ethyl acetate (5:1) to give white crystals (6 g, 86%). ¹H-NMR δ (DMSO-d₆, 400 MHz): 9.08 (brs, 1H, exchangeable with D₂O, NH), 6.98 (s, 1H), 6.92 (t, J=8.8 Hz, 2H), 6.69 (dd, J=4.8 and 8.8 Hz, 2H), 5.76 (d, J=8.0 Hz, 1H, exchangeable with D₂O, NH), 4.86 (q, J=8.0 Hz, 1H), 2.86 (ddd, J=4.8, 8.7 and 16.2 Hz, 1H), 2.70 (quint, J=8.1 Hz, 1H), 2.46 (m, 1H), 2.22 (s, 2H), 2.11 (s, 3H), 2.06 (s, 3H), 1.74 (m, 1H), 1.07 (s, 9H). MS: 369 (M+1).

Example 12

(−)-N-(1-(4-fluorophenylamino)-4,6-dimethyl-2,3-dihydro-1H-inden-5-yl)-3,3-dimethylbutanamide (−) N-(1-(4-fluorophenylamino)-4,6-dimethyl-2,3-dihydro-1H-inden-5-yl)-3,3-dimethylbutanamide was obtain by chiral HPLC resolution: Column, CHIRALPAK®AY®; Eluent, 100% acetonitrile; Temperature, room temperature; UV detection, 260 nm.
[α]$_D$−34.47 (methanol, 25° C.), 99.9% ee, RT: 4.0 min Example 13

(+) N-(1-(4-fluorophenylamino)-4,6-dimethyl-2,3-dihydro-1H-inden-5-yl)-3,3-dimethylbutanamide (+) N-(1-(4-fluorophenylamino)-4,6-dimethyl-2,3-dihydro-1H-inden-5-yl)-3,3-dimethylbutanamide was obtain by chiral HPLC resolution using the conditions described above.
[α]$_D$+29.27 (methanol, 25° C.), 99.0% ee, RT: 6.1 min Example 14

N-(4,6-dimethyl-1-(4-(trifluoromethyl)phenylamino)-2,3-dihydro-1H-inden-5-yl)-3,3-dimethylbutanamide

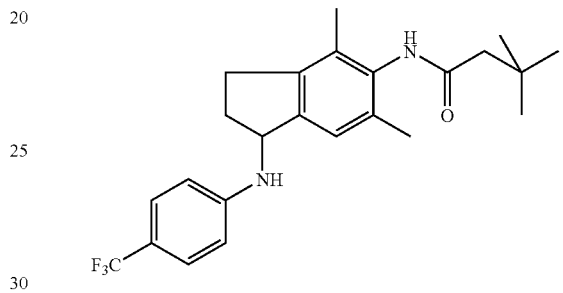

This compound was synthesized using the same procedure described above (example 11). ¹H-NMR δ (DMSO-d₆, 400 MHz): 9.10 (brs, 1H, exchangeable with D₂O, NH), 7.39 (d, J=8.0 Hz, 2H), 6.97 (s, 1H), 6.81 (d, J=8.0 Hz, 2H), 6.67 (d, J=8.0 Hz, 1H, exchangeable with D₂O, NH), 4.99 (q, J=8.0 Hz, 1H), 2.88 (ddd, J=4.8, 8.7 and 16.2 Hz, 1H), 2.74 (quint, J=8.1 Hz, 1H), 2.53 (m, 1H), 2.22 (s, 2H), 2.12 (s, 3H), 2.07 (s, 3H), 1.78 (m, 1H), 1.07 (s, 9H). MS: 417 (M−1).

Example 15

(−)-N-(4,6-dimethyl-1-(4-(trifluoromethyl)phenylamino)-2,3-dihydro-1H-inden-5-yl)-3,3-dimethylbutanamide (−) N-(4,6-dimethyl-1-(4-(trifluoromethyl)phenylamino)-2,3-dihydro-1H-inden-5-yl)-3,3-dimethylbutanamide was prepared by chiral HPLC: Column: CHIRALCEL®AD-H® (250×20 mm); Eluent: Hexane/Isopropanol (96/4); Flow Rate: 12 ml/min; Temperature: room temperature; UV detection: 254 nm; Run Time: 85 min.
[α]$_D$−4.18 (methanol, 25° C.), RT: 44 min.

Example 16

(+)-N-(4,6-dimethyl-1-(4-(trifluoromethyl)phenylamino)-2,3-dihydro-1H-inden-5-yl)-3,3-dimethylbutanamide (+) N-(4,6-dimethyl-1-(4-(trifluoromethyl)phenylamino)-2,3-dihydro-1H-inden-5-yl)-3,3-dimethylbutanamide was prepared by chiral HPLC using the conditions described above.
[α]$_D$+4.92 (methanol, 25° C.), RT: 59 min.

Example 17

N-(4,6-dimethyl-1-(4-chlorophenylamino)-2,3-dihydro-1H-inden-5-yl)-3,3-dimethylbutanamide

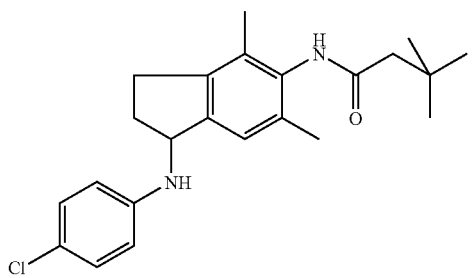

This compound was synthesized using the same procedure described above (example 11). $^1$H-NMR δ (DMSO-d$_6$, 400 MHz): 9.09 (brs, 1H, exchangeable with D$_2$O, NH), 7.10 (d, J=8.0 Hz, 2H), 6.97 (s, 1H), 6.71 (d, J=8.0 Hz, 2H), 6.08 (d, J=8.0 Hz, 1H, exchangeable with D$_2$O, NH), 4.88 (q, J=8.0 Hz, 1H), 2.87 (ddd, J=4.8, 8.7 and 16.2 Hz, 1H), 2.71 (quint, J=8.1 Hz, 1H), 2.47 (m, 1H), 2.22 (s, 2H), 2.11 (s, 3H), 2.06 (s, 3H), 1.74 (m, 1H), 1.07 (s, 9H). MS: 383 (M−1).

Example 18

N-(4,6-dimethyl-1-(4-bromophenylamino)-2,3-dihydro-1H-inden-5-yl)-3,3-dimethylbutanamide

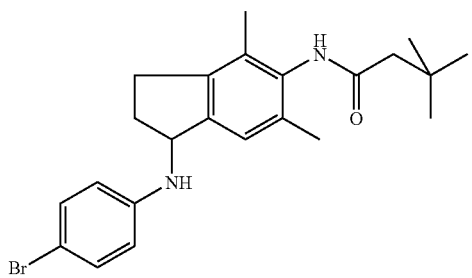

This compound was synthesized using the same procedure described above (example 11). $^1$H-NMR δ (DMSO-d$_6$, 400 MHz): 9.09 (brs, 1H, exchangeable with D$_2$O, NH), 7.21 (d, J=8.0 Hz, 2H), 6.97 (s, 1H), 6.67 (d, J=8.0 Hz, 2H), 6.11 (d, J=8.0 Hz, 1H, exchangeable with D$_2$O, NH), 4.88 (q, J=8.0 Hz, 1H), 2.86 (ddd, J=4.8, 8.7 and 16.2 Hz, 1H), 2.71 (quint, J=8.1 Hz, 1H), 2.47 (m, 1H), 2.22 (s, 2H), 2.11 (s, 3H), 2.06 (s, 3H), 1.75 (m, 1H), 1.07 (s, 9H). MS: 427 (M−1).

Example 19

N-(4,6-dimethyl-1-(3-chlorophenylamino)-2,3-dihydro-1H-inden-5-yl)-3,3-dimethylbutanamide

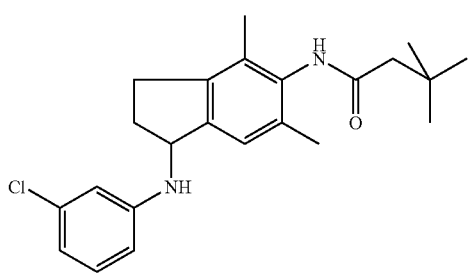

This compound was synthesized using the same procedure described above (example 11). $^1$H-NMR δ (DMSO-d$_6$, 400 MHz): 9.09 (brs, 1H, exchangeable with D$_2$O, NH), 7.08 (t, J=8.0 Hz, 1H), 6.97 (s, 1H), 6.72 (t, J=1.8 Hz, 1H), 6.66 (dd, J=1.8 and 8.0 Hz, 1H), 6.53 (dd, J=1.8 and 8.0 Hz, 1H), 6.22 (d, J=8.0 Hz, 1H, exchangeable with D$_2$O, NH), 4.91 (q, J=8.0 Hz, 1H), 2.87 (ddd, J=4.8, 8.7 and 16.2 Hz, 1H), 2.72 (quint, J=8.1 Hz, 1H), 2.47 (m, 1H), 2.22 (s, 2H), 2.12 (s, 3H), 2.06 (s, 3H), 1.74 (m, 1H), 1.07 (s, 9H). MS: 383 (M−1).

Example 20

N-(4,6-dimethyl-1-(3,4-dichlorophenylamine)-2,3-dihydro-1H-inden-5-yl)-3,3-dimethylbutanamide

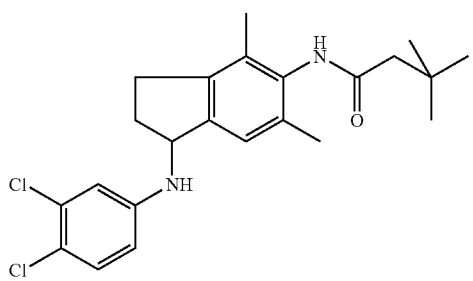

This compound was synthesized using the same procedure described above (example 11). $^1$H-NMR δ (DMSO-d$_6$, 400 MHz): 9.10 (brs, 1H, exchangeable with D$_2$O, NH), 7.27 (d, J=8.0 Hz, 1H), 6.97 (s, 1H), 6.90 (d, J=2.0 Hz, 1H), 6.70 (dd, J=2.0 and 8.0 Hz, 1H), 6.40 (d, J=8.0 Hz, 1H, exchangeable with D$_2$O, NH), 4.92 (q, J=8.0 Hz, 1H), 2.87 (ddd, J=4.8, 8.7 and 16.2 Hz, 1H), 2.71 (quint, J=8.1 Hz, 1H), 2.49 (m, 1H), 2.22 (s, 2H), 2.12 (s, 3H), 2.06 (s, 3H), 1.73 (m, 1H), 1.07 (s, 9H). MS: 417 (M−1).

Example 21

N-(4,6-dimethyl-1-(3,4-difluorophenylamino)-2,3-dihydro-1H-inden-5-yl)-3,3-dimethylbutanamide

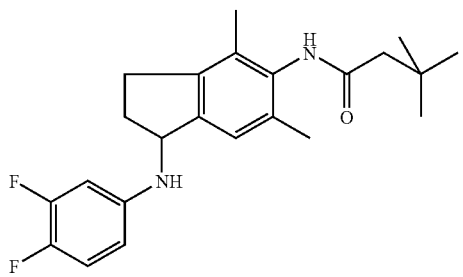

This compound was synthesized using the same procedure described above (example 11). $^1$H-NMR δ (DMSO-d$_6$, 400 MHz): 9.09 (brs, 1H, exchangeable with D$_2$O, NH), 7.11 (q, J=8.8 Hz, 1H), 6.97 (s, 1H), 6.67 (dq, J=2.0 and 8.8 Hz, 1H), 6.47 (d, J=8.0 Hz, 1H, exchangeable with D$_2$O, NH), 6.10 (m, 1H), 4.88 (q, J=8.0 Hz, 1H), 2.87 (ddd, J=4.8, 8.7 and 16.2 Hz, 1H), 2.72 (quint, J=8.1 Hz, 1H), 2.49 (m, 1H), 2.22 (s, 2H), 2.11 (s, 3H), 2.06 (s, 3H), 1.73 (m, 1H), 1.06 (s, 9H). MS: 385 (M−1).

Example 22

N-(4,6-dimethyl-1-(3,5-difluorophenylamino)-2,3-dihydro-1H-inden-5-yl)-3,3-dimethylbutanamide

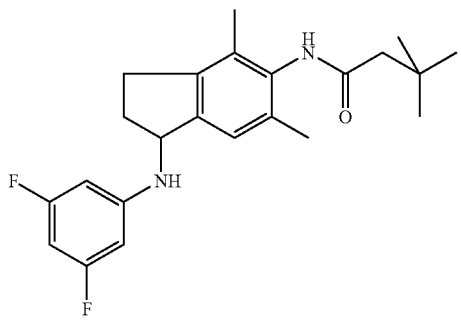

This compound was synthesized using the same procedure described above (example 11). $^1$H-NMR δ (DMSO-$d_6$, 400 MHz): 9.10 (brs, 1H, exchangeable with $D_2O$, NH), 6.97 (s, 1H), 6.59 (d, J=8.0 Hz, 1H, exchangeable with $D_2O$, NH), 6.35 (dd, J=2.0 and 10.8 Hz, 2H), 6.22 (tt, J=2.0 and 8.0 Hz, 1H), 4.92 (q, J=8.0 Hz, 1H), 2.87 (ddd, J=4.8, 8.7 and 16.2 Hz, 1H), 2.72 (quint, J=8.1 Hz, 1H), 2.49 (m, 1H), 2.22 (s, 2H), 2.12 (s, 3H), 2.06 (s, 3H), 1.73 (m, 1H), 1.07 (s, 9H). MS: 385 (M−1).

Example 23

N-(1-(6-fluoropyridin-3-ylamino)-4,6-dimethyl-2,3-dihydro-1H-inden-5-yl)-3,3-dimethylbutanamide

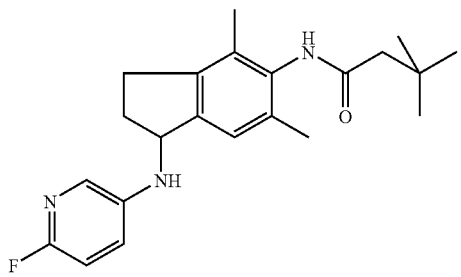

This compound was synthesized using the same procedure described above (example 11). $^1$H-NMR δ (DMSO-$d_6$, 400 MHz): 9.07 (brs, 1H, exchangeable with $D_2O$, NH), 7.60 (m, 1H), 7.27 (ddd, J=3.0, 7.0 and 8.6 Hz, 1H), 6.98 (s, 1H), 6.89 (dd, J=3.0 and 8.6 Hz, 1H), 6.05 (d, J=8.0 Hz, 1H, exchangeable with $D_2O$, NH), 4.91 (q, J=7.4 Hz, 1H), 2.88 (ddd, J=4.8, 8.7 and 16.2 Hz, 1H), 2.72 (quint, J=8.1 Hz, 1H), 2.51 (m, 1H), 2.22 (s, 2H), 2.12 (s, 3H), 2.06 (s, 3H), 1.73 (m, 1H), 1.07 (s, 9H). MS: 368 (M−1).

Example 24

N-(1-(6-trifluoromethylpyridin-3-ylamino)-4,6-dimethyl-2,3-dihydro-1H-inden-5-yl)-3,3-dimethylbutanamide

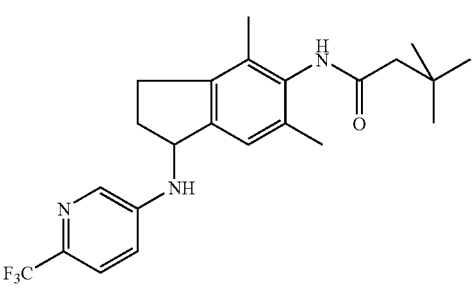

This compound was synthesized using the same procedure described above (example 11). $^1$H-NMR δ (DMSO-$d_6$, 400 MHz): 9.09 (brs, 1H, exchangeable with $D_2O$, NH), 8.16 (d, J=2.6 Hz, 1H), 7.54 (d, J=8.4 Hz, 1H), 7.17 (dd, J=2.6 and 8.4 Hz, 1H), 6.98 (s, 1H), 6.95 (d, J=8.0 Hz, 1H, exchangeable with $D_2O$, NH), 5.04 (q, J=8.0 Hz, 1H), 2.87 (ddd, J=4.8, 8.7 and 16.2 Hz, 1H), 2.72 (quint, J=8.1 Hz, 1H), 2.50 (m, 1H), 2.22 (s, 2H), 2.12 (s, 3H), 2.07 (s, 3H), 1.73 (m, 1H), 1.07 (s, 9H). MS: 418 (M−1).

Example 25

Ethyl 1-(4-fluorophenylamino)-2,3-dihydro-1H-inden-5-yl-carbamate

Step A: Ethyl 1-oxo-2,3-dihydro-1H-inden-5-yl-carbamate

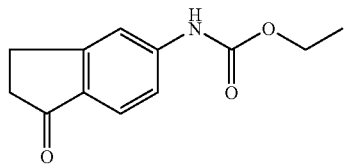

5-Amino-indan-1-one (0.15 g, 1 mmol) was dissolved in 8 ml of anhydrous ethanol and diethyl pyrocarbonate (0.20 g, 1.2 mmol) was added dropwise at room temperature. The resulting mixture was stirred at room temperature for 4 hours, then concentrated to dryness under reduced pressure to give the crude product, which is used for next step without further purification. CL Step B: Ethyl 1-(4-fluorophenylamino)-2,3-dihydro-1H-inden-5-yl-carbamate

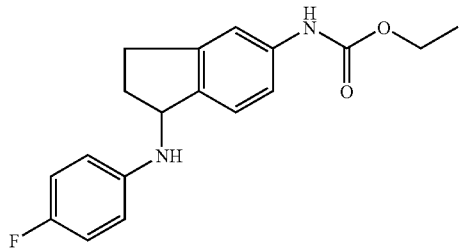

This compound was synthesized using the procedure described in example 11, step F. $^1$H-NMR δ (CDCl$_3$, 300 MHz): 7.39 (d, J=1.5 Hz, 1H), 7.25 (d, J=8.4 Hz, 1H), 7.10 (dd, J=1.5 and 8.4 Hz, 1H), 6.91 (t, J=8.8 Hz, 2H), 6.63 (dd, J=4.8 and 8.8 Hz, 2H), 4.89 (t, 6.6 Hz, 1H), 4.23 (q, J=7.2 Hz, 2H), 2.98 (ddd, J=4.8, 8.7 and 16.2 Hz, 1H), 2.85 (quint, J=8.1 Hz, 1H), 2.55 (m, 1H), 1.89 (m, 1H), 1.31 (t, J=7.2 Hz, 3H). MS: 313 (M−1).

Example 26

Biological Results

Compounds of this invention formula were evaluated for activity toward potassium channels in a cell-based Rb$^+$ efflux assay. This cellular bioassay is believed to faithfully represent the M channel activities identified with KCNQ2/3 heteromultimers. The most active compounds of this invention have EC$_{50}$s in the single-digit nM range, which represents a 40- to 400-fold improvement over retigabine. Additionally, antiseizure activity in vivo was evaluated in a mouse maximal electroshock seizure (MES) model, and neurotoxicities were determined from a rotorod neurocognitive motor impairment model and open field observation.

Methods:

Rubidium Efflux Test

PC-12 cells were grown at 37° C. and 5% CO$_2$ in DMEM/F12 Medium (Dulbecco's Modified Eagle Medium with Nutrient Mix F-12, available from Invitrogen of Carlsbad, Calif.), supplemented with 10% horse serum, 5% fetal bovine serum, 2 mM glutamine, 100 U/ml penicillin, and 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated, and the cells were washed once with 0.2 ml wash buffer (25 mM HEPES, pH 7.4, 150 mM NaCl, 1 mM MgCl$_2$, 0.8 mM NaH$_2$PO$_4$, 2 mM CaCl$_2$). The cells were then loaded with 0.2 ml Rb$^+$ loading buffer (wash buffer plus 5.4 mM RbCl$_2$, 5 mM glucose) and incubated at 37° C. for 2 h. Attached cells were washed quickly three times with buffer (same as Rb$^+$ loading buffer, but containing 5.4 mM KCl instead of RbCl) to remove extracellular Rb$^+$. Immediately following the wash, 0.2 ml of depolarization buffer (wash buffer plus 15 mM KCl solution) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for Rb$^+$ contents by atomic absorption spectroscopy (see below), they were stored at 4° C. without any negative effects on subsequent Rb$^+$ analysis.

The concentrations of Rb$^+$ in the supernatants (Rb$^+_{Sup}$) and the cell lysates (Rb$^+_{Lys}$) were quantified using an ICR8000 flame atomic absorption spectrometer (Aurora Biomed Inc., Vancouver, B.C.) under conditions defined by the manufacturer. Samples 0.05 ml in volume were processed automatically from microtiter plates by dilution with an equal volume of Rb$^+$ sample analysis buffer and injection into an air-acetylene flame. The amount of Rb$^+$ in the sample was measured by absorption at 780 nm using a hollow cathode lamp as light source and a PMT detector. A calibration curve covering the range 0-5 mg/L Rb$^+$ in sample analysis buffer was generated with each set of plates. The percent Rb$^+$ efflux (F) was defined by $$F=[Rb^+_{Sup}/(Rb^+_{Sup}+Rb^+_{Lys})]\times 100\%.$$

where the F$_c$ is the efflux in the presence of compound in depolarization buffer, F$_b$ is the efflux in basal buffer, and F$_s$ is the efflux in depolarization buffer, and F$_c$ is the efflux in the presence of compound in depolarization buffer. The efflux (F) and compound concentration relationship was plotted to calculate an EC$_{50}$ value, a compound's concentration for 50% of maximal Rb$^+$ efflux. The results are shown below.

Seizure Model Tests

Maximal Electroshock Seizure (MES) Test

The MES testing protocol is based on procedures established at the National Institute of Neurological Disorders and Stroke in conjunction with the Anticonvulsant Screening Program (ASP) at the University of Utah (White, H. S., Woodhead, J. H., Wilcox, K. S., Stables, J. P., Kupferberg, H. J and Wolf, H. H. 2002. "General Principles: Discovery and Preclinical Development of Antiepileptic Drugs," in *Antiepileptic Drugs,* 5th Edition, R. H. Levy, ed.; R. H. Mattson, B. S. Meldrum, and E. Perucca. Philadelphia, Lippincott Williams & Wilkins.), The goal of the test is to rapid identify and characterize the in vivo anticonvulsant activity of any compounds that have been shown active in PC-12 cellular based Rb$^+$ efflux assay.

Adult male CF-1 albino mice (18-25 g, Charles River Laboratories) are exclusively used for MES screening of compounds. Male Sprague-Dawley albino rats (100-125 g, Charles River Laboratories) are also used to test anticonvulsant compounds. Animals are permitted to rest and recover from transit for at least 48 hr prior to experimentation. Animals are used for AED testing only once. In some instances, the animals can be anesthetized prior to blood collection or whole brain extraction for pharmacokinetic assay. All animals are maintained and handled as outlined in standard animal care guidelines.

In the experiments, testing compounds are prepared as suspensions in 0.5% methyl cellulose (Sigma, Cat # M0512, Viscosity 4000 cP at 20° C.) in water, regardless of solubility. Dry powder compounds are initially ground with a glass rod in a test tube in several drops of methyl cellulose to create a paste and to break down any large chunks. After several minutes of grinding, the volume of the suspension is increased to the final concentration desired. The suspension is then sonicated using a Branson sonicator model 3510 in a water bath at room temperature for 15 minutes. Compound suspensions are further vortexed prior to animal dosing. In some of the cases, DMSO is used to initially solubilize compounds in small volumes and then this solution is added to the 0.5% methyl cellulose solution, in order to create more even and less aggregated compound suspensions. The final concentration of DMSO is 3.75%, an amount with no apparent toxicity or neuroprotective effects in our usual rotarod and MES tests. Methyl cellulose/DMSO compound suspensions are identically prepared for intraperitoneally (i.p.)dosing to mice or orally (p.o.) dosing to rats.

Initially the animals are weighed with an electronic scale and then marked. Data recording sheets are generated for each compound assessment. Mice or rats are dosed with the compound suspension at 0.01 mL/g of body weight. The typical injection volume range is between 180-250 μl for mice. Compounds are dosed by i.p. to mice using a 25 or 22 gauge needle, depending on the viscosity of the suspension. Rats are p.o. dosed using a flexible feeding tube, typically starting at a compound dose of 5 mg/kg.

A Rodent Electroconvulsive Stimulator (Model 200, Hamit-Darvin-Freesh, Snow Canyon Clinic, Ivins, Utah) is used for MES testing. A 60-Hz alternating current (50 mA for mice; 150 mA for rats) is delivered for 0.2 seconds through corneal electrodes to the mice. A drop of 0.5% tetracaine (Sigma, Cat. # T-7508) solution is placed on the eye prior to current delivery. The electrodes are subsequently placed gently onto the eyes of the animal and the electrical shock is initiated by triggering through a foot-pedal activator. The animals are restrained by hand and gently released as the shock is delivered and the seizure commences. Animals are monitored for hind limb tonic extension as the end point for this test. Current delivery is recorded as a measure of overall seizure-induction potential. Electrical current delivery can vary from approximately 30-55 mA (mice) or 90-160 mA (rats) depending on impedance in the animal and quality of the current delivery (i.e. correct placement of the electrodes on the cornea). Seizures will be successfully induced in control animals throughout this current range. Tonic extension is considered abolished if the hind limbs fail to become fully extended with the plane of the body at 180°. Lack of tonic extension suggests that the test compound has prevented the spread of seizure discharge through neural tissue. Although it is unnecessary in mice, the rats are pre-screened for seizure induction potential using the MES test in the absence of test compound twenty-four hours before compound dosing and the subsequent MES test. A success rate of 92-100% has been determined for the rat seizure induction potential. Rats that fail to develop tonic/clonic seizures during the pre-screening are not used for drug testing.

For a compound testing, time-to-peak effect studies are initially performed using 0.5, 1, 2, 4, 8 and 24 hr time points, typically using a single 5 or 25 mg/kg dose. The determined time-to-peak effect is used for further titration of a compound's potency ($ED_{50}$, the dose of a drug that protects 50% of animals from electrical induced seizure) in both mouse and rat models. For titrations, 8 animals are used per concentration, and dose (normally 5 concentrations) is varied until a full dose response curve is obtained. Probit analysis (ASP method) or non-linear regression analysis on Graph Pad (constraining the lower dose/effect value) is used to calculate an $ED_{50}$ value for the test compound.

Acute Toxicity Test

Rotarod Test

Prior to MES testing, compound dosed mice are scrutinized for abnormal neurologic status as defined by motor impairment on a slowly turning (6 rpm) rotarod apparatus (Model 755, Series 8, IITC Life Sciences, Woodland Hills, Calif.). The inability of a mouse to maintain its balance on the rotarod over a period of one minute (three falls=failure) signifies motor impairment and hence acute toxicity. These measurements are done at the same time points as the MES assay. Untreated normal mice are able to maintain balance on the rotarod for at least one minute without falling. Median toxicity of a compound ($TD_{50}$, the dose of a drug that results in motor impairment in 50% of animals) is determined.

Open Field Test

Before MES test, compound treated rats are visually observed for acute toxicity signs for approximately one minute in the open field test. Here, rats are gently placed into a plexiglass enclosure and are monitored for behavior consistent with toxicity including ataxia, trembling, hypoactivity (including failure to seek the walls), hypersensitivity, lack of exploratory behavior and lack of avoidance of the open area. Typically if the rats exhibits two or more of these abnormal behaviors they are scored as toxic. Of the three pairs of stereoisomers of compounds tested, the (+) stereoisomer constantly exhibited significantly less acute toxicity in this open field test than the (−) counterpart.

TABLE 1

ACTIVITIES OF EXEMPLARY COMPOUNDS

| COMPOUND | Mouse MES test | Rat ED50 | ACTIVITY EC50 |
|---|---|---|---|
|  | A | ND | C |
| (−)N-(5-(4-fluorophenylamino)-1,3-dimethyl-5,6,7,8-tetrahydronaphthalen-2-yl)-3,3-dimethylbutanamide | A | ND | B |
| (+)N-(5-(4-fluorophenylamino)-1,3-dimethyl-5,6,7,8-tetrahydronaphthalen-2-yl)-3,3-dimethylbutanamide | A | ND | C |
|  | A | ND | B |

TABLE 1-continued

ACTIVITIES OF EXEMPLARY COMPOUNDS

| COMPOUND | Mouse MES test | Rat ED50 | ACTIVITY EC50 |
|---|---|---|---|
| (3,4-dichlorophenyl-NH tetrahydronaphthalenyl dimethyl neopentyl amide) | B | ND | B |
| (4-chlorophenyl-NH tetrahydronaphthalenyl dimethyl neopentyl amide) | A | ND | B |
| (4-bromophenyl-NH tetrahydronaphthalenyl dimethyl neopentyl amide) | ND | ND | B |
| (3-chlorophenyl-NH tetrahydronaphthalenyl dimethyl neopentyl amide) | A | ND | B |
| (3,5-difluorophenyl-NH tetrahydronaphthalenyl dimethyl neopentyl amide) | A | ND | B |

TABLE 1-continued

ACTIVITIES OF EXEMPLARY COMPOUNDS

| COMPOUND | Mouse MES test | Rat ED50 | ACTIVITY EC50 |
|---|---|---|---|
| 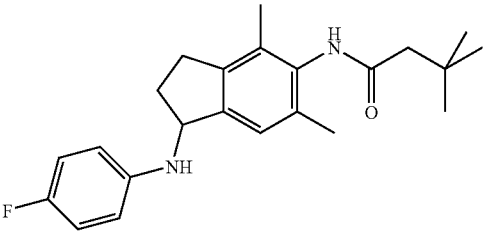 | A | A | B |
| (−)N-(1-(4-fluorophenylamino)-4,6-dimethyl-2,3-dihydro-1H-inden-5-yl)-3,3-dimethylbutanamide | A | A | A |
| (+)N-(1-(4-fluorophenylamino)-4,6-dimethyl-2,3-dihydro-1H-inden-5-yl)-3,3-dimethylbutanamide | A | A | B |
| 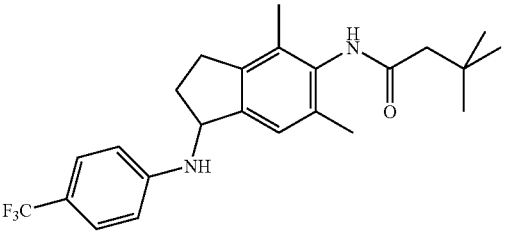 | A | A | B |
| (−)N-(4,6-dimethyl-1-(4-(trifluoromethyl)phenylamino)-2,3-dihydro-1H-inden-5-yl)-3,3-dimethylbutanamide | A | A | A |
| (+)N-(4,6-dimethyl-1-(4-(trifluoromethyl)phenylamino)-2,3-dihydro-1H-inden-5-yl)-3,3-dimethylbutanamide | A | A | B |
| 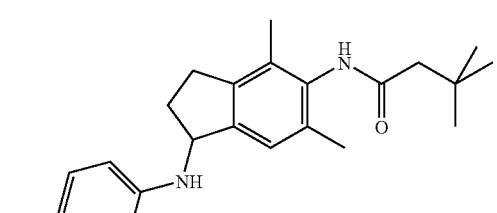 | A | ND | A |
| 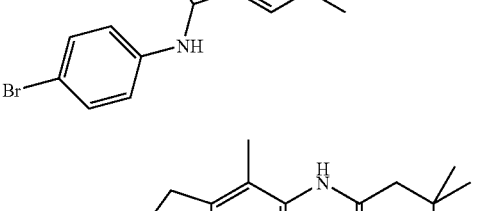 | A | ND | A |
| 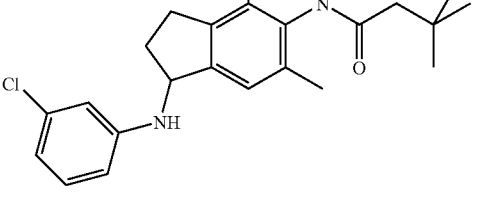 | A | ND | B |

TABLE 1-continued

ACTIVITIES OF EXEMPLARY COMPOUNDS

| COMPOUND | Mouse MES test | Rat ED50 | ACTIVITY EC50 |
|---|---|---|---|
| (3,4-dichlorophenyl-NH indane with 4,6-dimethyl, NHC(O)CH₂C(CH₃)₃) | A | ND | A |
| (3,4-difluorophenyl-NH indane with 4,6-dimethyl, NHC(O)CH₂C(CH₃)₃) | A | ND | B |
| (3,5-difluorophenyl-NH indane with 4,6-dimethyl, NHC(O)CH₂C(CH₃)₃) | A | ND | B |
| (6-fluoropyridin-3-yl-NH indane with 4,6-dimethyl, NHC(O)CH₂C(CH₃)₃) | A | ND | D |
| (6-trifluoromethylpyridin-3-yl-NH indane with 4,6-dimethyl, NHC(O)CH₂C(CH₃)₃) | A | ND | C |
| (4-fluorophenyl-NH indane, NHC(O)OEt) | ND | ND | E |

TABLE 1-continued

ACTIVITIES OF EXEMPLARY COMPOUNDS

| COMPOUND | Mouse MES test | Rat ED50 | ACTIVITY EC50 |
|---|---|---|---|
| 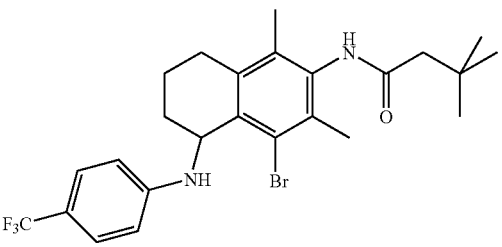 | ND | ND | E |

Legend:
For Rb+ efflux cellular assay: A: EC50 ≦ 1 nM; B: = 1 nM < EC50 ≦ 10 nM; C: 10 nM < EC50 ≦ 50 nM; D: 50 nM < EC50 ≦ 500 nM; E: > 500 nM.
For mouse MES test at ip dosing of 12.5 mg/kg: A: active; B: inactive;
For rat MES test: A: ED50 < 20 mg/kg; B: ED50 > 20 mg/kg;
ND: not determined;

Studies of Compound's KCNQ2/3 Opening Activity and KCNQ Subtype Selectivity Using Electrophysiological Patch Clamp in *Xenopus* oocytes Expression in *Xenopus laevis* Oocytes Female *Xenopus laevis* extracted ovaries were purchased from eNASCO (LM00935MX, eNASCO Fort Atkinson, Wis.). Following manual dissection of the oocytes into smaller groups, the oocytes were defolliculated by enzymatic treatment with collagenase type 2 (LS004177, Worthington, Lakewood, N.J.) for 1½ hour in the presence of calcium-free Culture Bath solution (88 mM NaCl, 1 mM KCl, 0.82 mM $MgSO_4$, 2.4 mM $NaHCO_3$, and 5 mM HEPES, pH 7.5). Oocytes were then kept in supplemented Culture Bath solution (88 mM NaCl, 1 mM KCl, 0.82 mM $MgSO_4$, 0.9 mM $CaCl_2$, 2.4 mM $NaHCO_3$, 1 mM sodium pyruvate, 0.05 mg/ml Geneticin, 100 U/ml penicillin, 0.1 mg/ml streptomycin and 5 mM HEPES, pH 7.5) at 19° C. for 24 hours before injection of cRNA. Approximately 50 nl cRNA (about 50 ng) was injected for KCNQ1, KCNQ4, and KCNQ5 using a Nanoject microinjector (Drummond, Broomall, Pa., USA). For co-expression of KCNQ2 and KCNQ3 and of KCNQ1 and KCNE1, cRNA's were mixed in equal molar ratios before injection of approximately 50 nl. The mixtures contained about 10+10 ng and 12.5+2.5 ng cRNA, respectively. The smaller amounts are needed because larger currents arise when KCNQ2/KCNQ3 and KCNQ1/KCNE1 are co-expressed. Oocytes were kept in Culture Barth solution at 19° C. which was changed daily and currents were recorded after 3 to 5 days.

Electrophysiology

KCNQ channel currents expressed in *Xenopus laevis* oocytes were recorded using a two-electrode voltage-clamp. The recordings were made at room temperature in recording solution (96 mM NaCl, 2 mM KCl, 1 mM $MgCl_2$, 1.8 mM $CaCl_2$, and 5 mM HEPES, pH 7.5) using a two-electrode voltage-clamp amplifier (OC-725C, Warner Instrument, Hamden, Conn., USA). The oocytes were placed in custom built perfusion chambers connected to a continuous flow system and impaled with a current electrode and a voltage-clamp electrode pulled from borosilicate glass on a Flaming/Brown Micropipette Puller (Sutter Instruments Co, Novato, Calif., USA). Recording electrodes were filled with 3 M KCl and had a resistance of 0.5 to 2.5 MΩ.

Compounds

All compounds were dissolved in DMSO to obtain concentrated stock solutions. On the day of electrophysiological experiments the stock solutions were thawed and diluted in recording solution to their final concentrations. The final DMSO concentration never exceeded 0.1%. Compound delivery was performed using a custom built multi-barrel apparatus connected to the flow system.

Calculations

Data were acquired by means of an Axograph X software (Axograph Scientific) and analyzed using Graph Pad Prism (GraphPad Software Inc., CA, USA).

Concentration—response curves were constructed by plotting the increase in steady-state current expressed in percentages as a function of drug concentration. During the course of the experiment, while various concentrations of the drug were being dosed, the resting voltage was held at −90 mV and pulsed to −60 mV, −40 mV, and −50 mV for 5 s for KCNQ2/KCNQ3, KCNQ4 and KCNQ5 channels respectively. The plot was then fitted to a Hill function:

$$Response = R2 + (R1-R2)/[1+(C/EC_{50})^{nH}]$$

where R1 is the initial response, R2 is the maximum response, C is the drug concentration and nH is the slope (Hill coefficient) of the curve.

The efficacy of compounds of this invention in comparison with retigabine (as a positive control) was determined by recording the steady current using the above voltage protocol for the channels in the presence of the $EC_{75}$ of the drugs. After steady channel current was recorded in the presence of retigabine at its EC75, recorded oocyte was washed with the recording solution until its steady current returned to its normal level without the presence of any drugs. Then the channel steady current was recorded in the presence of the test compound at its $EC_{75}$. The percent efficacy was then expressed as:

$$\% \text{ efficacy} = (C2/C1) \times 100\%$$

where C2 is the recorded steady current in the presence of a compound at its $EC_{75}$ and C1 is the recorded steady current in the presence of Retigabine at its $EC_{75}$.

Results

Representative example compounds exhibited no modulating activity on the cardiac KCNQ1 channel, while they demonstrated significantly activity in activating the rest KCNQ channels.

What is claimed is:

1. A compound of formula I,

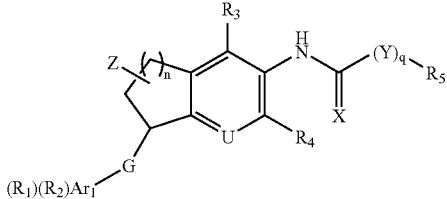

wherein G is —O—, —S—, —C(g$_1$)(g$_2$)-, or —NH—, where g$_1$ and g$_2$ are, independently, H, phenyl, halogen, methoxy, halomethyl, methoxymethyl, or C$_1$-C$_3$ alkyl; n=1, 2, or 3;

each Ar$_1$ is independently a 5- to 10-member mono- or bicyclic aromatic group, optionally containing 1-4 heteroatoms selected independently from N, O, and S;

R$_1$ and R$_2$ are selected, independently, from H, CN, halogen, CH$_2$CN, OH, NO$_2$, CH$_2$F, CHF$_2$, CF$_3$, CF$_2$CF$_3$, C$_1$-C$_6$ alkyl, OR$_8$, C(=O)R$_9$, C(=O)OR$_{10}$, OC(=O)R$_{11}$, SR$_{12}$, NR$_{13}$C(=O)R$_{14}$, NR$_{13}$C(=NH)R$_{14}$, C(=O)NR$_{15}$R$_{16}$, CH$_2$C(=O)NR$_{15}$R$_{16}$, CH$_3$NHC(=NH)—, CH$_3$C(=NH)NH—, CH$_2$C(=NH)NH$_2$, NR$_{17}$R$_{18}$, SO$_2$R$_{19}$, N(R$_{20}$) SO$_2$ R$_2$l, SO$_2$NR$_{22}$R$_{23}$, C$_3$-C$_6$ cycloalkyl, C$_5$-C$_6$ cycloalkenyl, C$_2$-C$_6$ alkenyl, or C$_2$-C$_6$ alkynyl; U is N or CR';

R', R$_3$, and R$_4$ are, independently, H, halogen, trifluoromethyl, C$_{1-6}$ alkyl, which C$_{1-6}$ alkyl group optionally substituted with 1 or 2 groups selected, independently, from OH, halogen, C$_1$-C$_3$ alkyl, OC$_1$-C$_3$ alkyl, or trifluoromethyl;

X=O or S; Y is O or S; Z is H, halogen, OH, CN, CH$_2$CN, C$_1$-C$_6$ alkyl, C$_3$-C$_6$ cycloalkyl, O—C$_1$-C$_6$ alkyl, (CH$_2$), C$_3$-C$_6$ cycloalkyl, O—C$_3$-C$_6$ cycloalkyl, 0-(CH$_2$)wC3-C6 cycloalkyl, q=1 or 0;

R$_5$ is C$_1$-C$_6$ alkyl, (CHR$_6$), C$_3$-C$_6$ cycloalkyl, (CHR$_6$)$_w$CH$_2$C$_3$-C$_6$ CH$_2$(CHR$_6$)$_w$C$_3$-C$_6$ cycloalkyl, (CHR$_6$)$_w$C$_5$-C$_6$ cycloalkenyl, CH$_2$(CHR$_6$), C$_5$-C$_6$ cycloalkenyl, C$_2$-C$_6$ alkenyl, C$_2$-C$_6$ alkynyl, Ar$_2$, (CHR$_6$)$_w$Ar$_2$, CH$_2$(CHR$_6$)$_w$Ar$_2$, or (CHR$_6$)$_w$CH$_2$Ar$_2$, where w -0-3, each Ar$_2$ is independently a 5- to 10-member mono- or bicyclic aromatic group, optionally containing 1-4 ring heteroatoms selected independently from N, O, and S;

R$_6$ is H or C$_1$-C$_3$ alkyl; and

R$_8$-R$_{23}$ are, independently, H, C$_1$-C$_6$ alkyl, C$_3$-C$_6$ cycloalkyl, (CHR$_6$)$_w$C$_3$-C$_6$ cycloalkyl, C$_2$-C$_6$ alkenyl, C$_2$-C$_6$ alkenyl, C$_2$-C$_6$ alkynyl, where all alkyl, cycloalkyl, alkenyl, alkynyl, aryl, groups are optionally substituted with one or two substituents selected independently from C$_1$-C$_3$ alkyl, halogen, OH, OMe, CN, CH$_2$F, and trifluoromethyl; where, additionally, the alkenyl and alkynyl groups are optionally substituted with phenyl or C$_3$-C$_6$ cycloalkyl; and where all cycloalkyl groups optionally contain one or two ring heteroatoms selected independently from N, O, and S;

or a pharmaceutically acceptable salt thereof.

2. The compound of claim 1, where NH—C(=X)—(Y)$_q$—R$_5$ is NHC(=O)R$_5$.

3. The compound of claim 1, where NH—C(=X)—(Y)$_q$—R$_5$ is NHC(=O)OR$_5$.

4. The compound of claim 1, where NH—C(=X)—(Y)$_q$—R$_5$ is NHC(=S)SR$_5$.

5. The compound of claim 1, where NH—C(=X)—(Y)$_q$—R$_5$ is NHC(=S)R$_5$.

6. The compound of claim 1, where NH—C(=X)—(Y)$_q$—R$_5$ is NHC(=S)OR$_5$.

7. The compound of claim 1, where NH—C(=X)—(Y)$_q$—R$_5$ is NHC(=O)SR$_5$.

8. A compound of formula I-N,

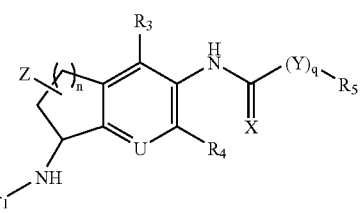

where all variables are as defined in claim 1.

9. A compound of formula I-O,

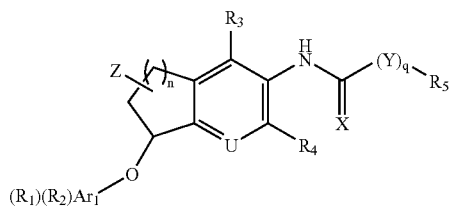

where all variables are as defined in claim 1.

10. A compound of formula I-S,

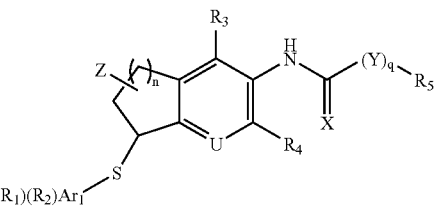

where all variables are as defined in claim 1.

11. A compound of formula I-Cgg,

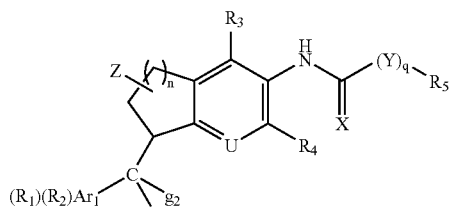

where all variables are as defined in claim 1.

12. The compound of claim 1 which is a compound of formula IA

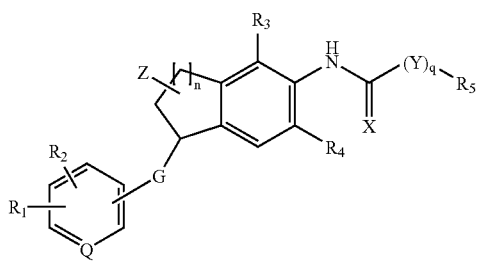

wherein Q=CR$_7$ or N, where R$_7$ is H or C$_1$-C$_6$ alkyl and all other variables are as defined in claim 1.

13. The compound of claim 12 which is a compound of formula I-N-A,

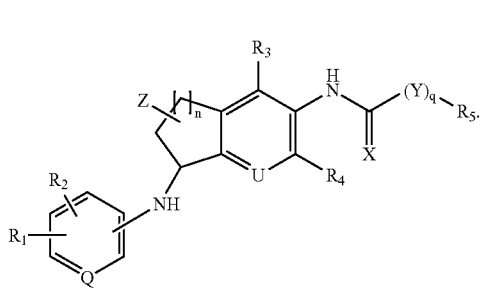

14. The compound of any of claims 1-13, where Ar$_1$ is phenyl or pyridyl, and n is 1.

15. The compound of any of claims 1-13, where Ar$_1$ is phenyl or pyridyl, and n is 2.

16. The compound of any of claims 1-13, where Ar$_1$ is phenyl or pyridyl, and n is 3.

17. The compound of any of claims 1-13, where R$_1$ is H, CH$_3$, CF$_3$, Cl, or F; Ar$_1$ is phenyl; and n is 1.

18. The compound of any of claims 1-13, where R$_1$ is H, CH$_3$, CF$_3$, Cl, or F; Ar$_1$ is phenyl; and n is 2.

19. The compound of any of claims 1-13, where R$_1$ is H, CH$_3$, CF$_3$, Cl, or F; Ar$_1$ is phenyl; and n is 3.

20. The compound of any of claims 1-13, where R$_1$ is H, CH$_3$, CF$_3$, Cl, or F; Z is H, halogen, or methyl; R$_3$ is H, CH$_3$, Cl, or F; Ar$_1$ is phenyl; and n is 1.

21. The compound of any of claims 1-13, where R$_1$ is H, CH$_3$, CF$_3$, Cl, or F; Z is H, halogen, or methyl; R$_3$ is H, CH$_3$, Cl, or F; Ar$_1$ is phenyl; and n is 2.

22. The compound of any of claims 1-13, where R$_1$ is H, CH$_3$, CF$_3$, Cl, or F; Z is H, halogen, or methyl; R$_3$ is H, CH$_3$, Cl, or F; Ar$_1$ is phenyl; and n is 3.

23. The compound of any of claims 1-13, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; Ar$_1$ is phenyl; X is O; and n is 1.

24. The compound of any of claims 1-13, where R$_1$ is H, CH$_3$, CF$_3$, Cl, or F; Z is H, halogen, or methyl; R$_3$ is H, CH$_3$, Cl, or F; Ar$_1$ is phenyl; X is O; and n is 2.

25. The compound of any of claims 1-13, where R$_1$ is H, CH$_3$, CF$_3$, Cl, or F; Z is H, halogen, or methyl; R$_3$ is H, CH$_3$, Cl, or F; Ar$_1$ is phenyl; X is O; and n is 3.

26. The compound of any of claims 1-11, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; Ar$_1$ is phenyl; X is O; U is CH; q is zero; R$_5$ is C$_5$-C$_6$ alkyl or (CHR$_6$)$_w$C$_3$-C$_6$ cycloalkyl; and n is 1.

27. The compound of any of claims 1-11, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; Ar$_1$ is phenyl; X is O; U is CH; q is zero; R$_5$ is C$_5$-C$_6$ alkyl or (CHR$_6$)$_w$C$_3$-C$_6$ cycloalkyl; and n is 2.

28. The compound of any of claims 1-11, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; Ar$_1$ is phenyl; X is O; U is CH; q is zero; R$_5$ is C$_5$-C$_6$ alkyl or (CHR$_6$)$_w$C$_3$-C$_6$ cycloalkyl; and n is 3.

29. The compound of claim 13, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; Ar$_1$ is phenyl; X is O; U is CH; q is zero; R$_5$ is C$_5$-C$_6$ alkyl or (CHR$_6$)$_w$C$_3$-C$_6$ cycloalkyl; and n is 1.

30. The compound of claim 13, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; Ar$_1$ is phenyl; X is O; U is CH; q is zero; R$_5$ is C$_5$-C$_6$ alkyl or (CHR$_6$)$_w$C$_3$-C$_6$ cycloalkyl; and n is 2.

31. The compound of claim 13, where R$_1$ is H, CH$_3$, CF$_3$, Cl, or F; R$_2$ is H, F, or Cl; Z is H; R$_3$ is H, CH$_3$, Cl, or F; R$_4$ is H or CH$_3$; MI is phenyl; X is O; U is CH; q is zero; R$_5$ is C$_5$-C$_6$ alkyl or (CHR$_6$)$_w$C$_3$-C$_o$ cycloalkyl; and n is 3.

32. A composition comprising a pharmaceutically acceptable carrier and one or more of the following:
  i. a compound of formula I according to claim 1;
  ii. a pharmaceutically acceptable salt of said compound of formula I; or
  iii. a pharmaceutically acceptable ester of said compound of formula I.

33. The composition of claim 32, wherein the compound of formula I is a compound of formula I-N, I-O, I-S or I-Cgg:

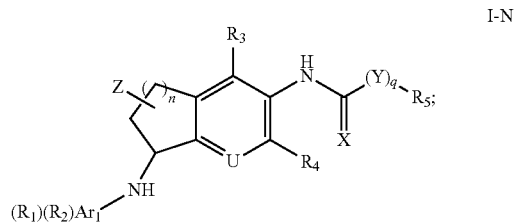

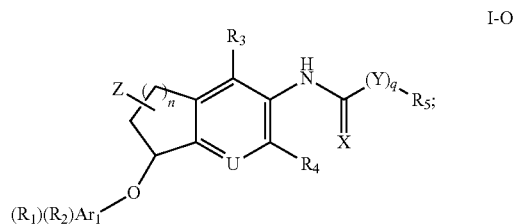

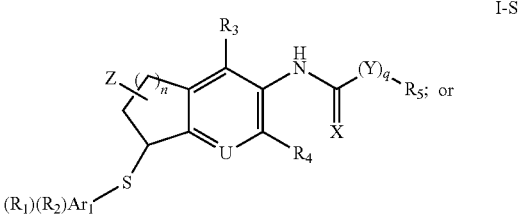

-continued

I-Cgg

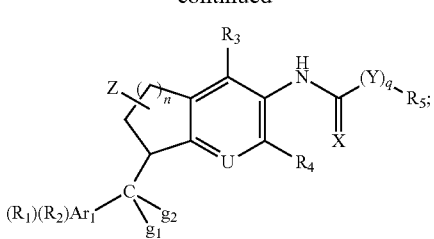

wherein all variable are as described in claim 1.

34. A compound selected from one of the following:
i) N-(5-(4-fluorophenylamino)-1,3-dimethyl-5,6,7,8-tetrahydronaphthalen-2-yl)-3,3-dimethylbutanamide;
ii) N-(1,3-dimethyl-5-(4-(trifluoromethyl)phenylamino)-5,6,7,8-tetrahydronaphthalen-2-yl)-3,3-dimethylbutanamide;
iii) N-(1,3-dimethyl-5-(3,4-dichlorophenylamino)-5,6,7,8-tetrahydronaphthalen-2-yl)-3,3-dimethylbutanamide;
iv) N-(1,3-dimethyl-5-(4-chlorophenylamino)-5,6,7,8-tetrahydronaphthalen-2-yl)-3,3-dimethylbutanamide;
v) N-(1,3-dimethyl-5-(4-bromophenylamino)-5,6,7,8-tetrahydronaphthalen-2-yl)-3,3-dimethylbutanamide;
vi) N-(1,3-dimethyl-5-(3-chlorophenylamino)-5,6,7,8-tetrahydronaphthalen-2-yl)-3,3-dimethylbutanamide;
vii) N-(1,3-dimethyl-5-(3,5-difluorophenylamino)-5,6,7,8-tetrahydronaphthalen-2-yl)-3,3-dimethylbutanamide;
viii) N-(1-(4-fluorophenylamino)-4,6-dimethyl-2,3-dihydro-1H-inden-5-yl)-3,3-dimethylbutanamide;
ix) N-(4,6-dimethyl-1-(4-(trifluoromethyl)phenylamino)-2,3-dihydro-1H-inden-5-yl)-3,3-dimethylbutanamide;
x) N-(4,6-dimethyl-1-(4-chlorophenylamino)-2,3-dihydro-1H-inden-5-yl)-3,3-dimethylbutanamide;
xi) N-(4,6-dimethyl-1-(4-bromophenylamino)-2,3-dihydro-1H-inden-5-yl)-3,3-dimethylbutanamide;
xii) N-(4,6-dimethyl-1-(3-chlorophenylamino)-2,3-dihydro-1H-inden-5-yl)-3,3-dimethylbutanamide;
xiii) N-(4,6-dimethyl-1-(3,4-dichlorophenylamino)-2,3-dihydro-1H-inden-5-yl)-3,3-dimethylbutanamide;
xxiv) N-(4,6-dimethyl-1-(3,4-difluorophenylamino)-2,3-dihydro-1H-inden-5-yl)-3,3-dimethylbutanamide;
xxv) N-(4,6-dimethyl-1-(3,5-difluorophenylamino)-2,3-dihydro-1H-inden-5-yl)-3,3-dimethylbutanamide;
xxvi) N-(1-(6-fluoropyridin-3-ylamino)-4,6-dimethyl-2,3-dihydro-1H-inden-5-yl)-3,3-dimethylbutanamide;
xxvii) N-(1-(6-trifluoromethylpyridin-3-ylamino)-4,6-dimethyl-2,3-dihydro-1H-inden-5-yl)-3,3-dimethylbutanamide;
xxviii) Ethyl 1-(4-fluorophenylamino)-2,3-dihydro-1H-inden-5-yl-carbamate, or
xxiv) N-[4-bromo-1,3-dimethyl-5-(4-trifluoromethylphenylamino)-5,6,7,8-tetrahydro-naphthalen-2-yl]-3,3-dimethyl-butyramide.

35. A compound selected from one of the following:
i) (−)N-(5-(4-fluorophenylamino)-1,3-dimethyl-5,6,7,8-tetrahydronaphthalen-2-yl)-3,3-dimethylbutanamide;
ii) (+)N-(5-(4-fluorophenylamino)-1,3-dimethyl-5,6,7,8-tetrahydronaphthalen-2-yl)-3,3-dimethylbutanamide;
iii) (−)N-(1-(4-fluorophenylamino)-4,6-dimethyl-2,3-dihydro-1H-inden-5-yl)-3,3-dimethylbutanamide;
iv) (+)N-(1-(4-fluorophenylamino)-4,6-dimethyl-2,3-dihydro-1H-inden-5-yl)-3,3-dimethylbutanamide;
v) (−)N-(4,6-dimethyl-1-(4-(trifluoromethyl)phenylamino)-2,3-dihydro-1H-inden-5-yl)-3,3-dimethylbutanamide, or
vi) (+)N-(4,6-dimethyl-1-(4-(trifluoromethyl)phenylamino)-2,3-dihydro-1H-inden-5-yl)-3,3-dimethylbutanamide.

36. A composition comprising a pharmaceutically acceptable carrier or diluent, a syrup for pediatric use, and at least one of the following: a pharmaceutically effective amount of a compound of formula I according to claim 1, and a pharmaceutically acceptable salt of said compound of formula I.

37. A tablet comprising a pharmaceutically acceptable carrier or diluent, and at least one of the following: a pharmaceutically effective amount of a compound of formula I according to claim 1, and a pharmaceutically acceptable salt of said compound of formula I.

38. The tablet of claim 37, where the tablet is chewable.

* * * * *